(12) United States Patent
Meade et al.

(10) Patent No.: US 9,744,061 B2
(45) Date of Patent: *Aug. 29, 2017

(54) INTESTINAL SLEEVE

(71) Applicant: GI Dynamics, Inc., Boston, MA (US)

(72) Inventors: John C. Meade, Mendon, MA (US);
Andy H. Levine, Newton, MA (US);
David A. Melanson, Hudson, NH (US);
John F. Cvinar, West Chester, PA (US)

(73) Assignee: GI Dynamics, Inc., Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/962,610

(22) Filed: Dec. 8, 2015

(65) Prior Publication Data

US 2016/0089257 A1 Mar. 31, 2016

Related U.S. Application Data

(60) Continuation of application No. 14/305,518, filed on Jun. 16, 2014, now Pat. No. 9,237,944, which is a
(Continued)

(51) Int. Cl.
*A61F 2/04* (2013.01)
*A61B 17/04* (2006.01)
(Continued)

(52) U.S. Cl.
CPC ........ *A61F 5/0076* (2013.01); *A61B 17/0401* (2013.01); *A61B 17/0482* (2013.01); *A61F 2/04* (2013.01); *A61F 2/848* (2013.01); *A61F 2/91* (2013.01); *A61F 2/915* (2013.01); *A61B 17/12* (2013.01); *A61B 2017/0419* (2013.01); *A61B 2017/06052* (2013.01); *A61F 2/95* (2013.01);
(Continued)

(58) Field of Classification Search
CPC .................................. A61F 2/04; A61B 17/04
USPC .............................................. 623/23.65–23.7
See application file for complete search history.

(56) References Cited

U.S. PATENT DOCUMENTS 1,899,781 A 2/1933 Twiss
2,464,933 A 3/1949 Kaslow
(Continued)

FOREIGN PATENT DOCUMENTS

DE 33 26 061 A1 2/1984
EP 0 480 667 B1 4/1992
(Continued)

OTHER PUBLICATIONS

Bethge, N., et al., "Human tissue responses to metal stents implanted in vivo for the palliation of malignant stenoses," Gastrointestinal Endoscopy 43(6):596-602 (1996).
(Continued)

*Primary Examiner* — Suzette J Gherbi
(74) *Attorney, Agent, or Firm* — Clark & Elbing LLP

(57) ABSTRACT

A gastrointestinal implant device is anchored in the duodenum and extends beyond the ligament of Treitz. All food exiting the stomach is funneled through the device. The gastrointestinal device includes an anchor for attaching the device to the duodenum and an unsupported flexible sleeve. The anchor can include a stent and/or a wave anchor and is collapsible for catheter-based delivery and removal.

19 Claims, 46 Drawing Sheets

Related U.S. Application Data continuation of application No. 13/170,785, filed on Jun. 28, 2011, now Pat. No. 8,834,405, which is a continuation of application No. 12/684,309, filed on Jan. 8, 2010, now Pat. No. 7,981,163, which is a continuation-in-part of application No. 11/493,487, filed on Jul. 26, 2006, now Pat. No. 7,682,330, which is a division of application No. 10/858,851, filed on Jun. 1, 2004, now Pat. No. 7,476,256.

(60) Provisional application No. 60/528,084, filed on Dec. 9, 2003, provisional application No. 60/544,527, filed on Feb. 13, 2004.

(51) Int. Cl.
| | | |
|---|---|---|
| *A61F 5/00* | (2006.01) | |
| *A61F 2/91* | (2013.01) | |
| *A61F 2/915* | (2013.01) | |
| *A61B 17/12* | (2006.01) | |
| *A61B 17/06* | (2006.01) | |
| *A61F 2/95* | (2013.01) | |
| *A61F 2/848* | (2013.01) | |

(52) U.S. Cl.
 CPC . *A61F 2002/045* (2013.01); *A61F 2002/8483* (2013.01); *A61F 2002/91541* (2013.01); *A61F 2002/91558* (2013.01); *A61F 2002/9511* (2013.01); *A61F 2220/0008* (2013.01); *A61F 2220/0016* (2013.01); *A61F 2220/0058* (2013.01); *A61F 2220/0066* (2013.01)

(56) References Cited

U.S. PATENT DOCUMENTS

| | | |
|---|---|---|
| 3,516,408 A | 6/1970 | Montani |
| 3,780,740 A | 12/1973 | Rhea |
| 4,133,315 A | 1/1979 | Berman et al. |
| 4,134,405 A | 1/1979 | Smit |
| 4,246,893 A | 1/1981 | Berson |
| 4,265,694 A | 5/1981 | Boretos et al. |
| 4,270,542 A | 6/1981 | Plumley |
| 4,271,827 A | 6/1981 | Angelchik |
| 4,279,251 A | 7/1981 | Rüsch |
| 4,315,509 A | 2/1982 | Smit |
| 4,341,218 A | 7/1982 | Ü |
| 4,403,604 A | 9/1983 | Wilkinson et al. |
| 4,416,267 A | 11/1983 | Garren et al. |
| 4,501,264 A | 2/1985 | Rockey |
| 4,580,568 A | 4/1986 | Gianturco |
| 4,607,618 A | 8/1986 | Angelchik |
| 4,617,932 A | 10/1986 | Kornberg |
| 4,641,653 A | 2/1987 | Rockey |
| 4,648,383 A | 3/1987 | Angelchik |
| 4,763,653 A | 8/1988 | Rockey |
| 4,768,507 A | 9/1988 | Fischell et al. |
| 4,787,899 A | 11/1988 | Lazarus |
| 4,823,808 A | 4/1989 | Clegg et al. |
| 4,846,836 A | 7/1989 | Reich |
| 4,878,905 A | 11/1989 | Blass |
| 4,899,747 A | 2/1990 | Garren et al. |
| 4,905,693 A | 3/1990 | Ravo |
| 4,913,141 A | 4/1990 | Hillstead |
| 4,991,594 A | 2/1991 | Angelchik |
| 5,035,706 A | 7/1991 | Gianturco et al. |
| 5,037,387 A | 8/1991 | Quinn et al. |
| 5,041,126 A | 8/1991 | Gianturco |
| 5,057,091 A | 10/1991 | Andersen |
| 5,059,166 A | 10/1991 | Fischell et al. |
| 5,104,399 A | 4/1992 | Lazarus |
| 5,123,917 A | 6/1992 | Lee |
| 5,135,516 A | 8/1992 | Sahatjian et al. |
| 5,139,478 A | 8/1992 | Koninckx et al. |
| 5,152,756 A | 10/1992 | Quinn et al. |
| 5,152,782 A | 10/1992 | Kowligi et al. |
| 5,176,617 A | 1/1993 | Fischell et al. |
| 5,190,561 A | 3/1993 | Graber |
| 5,207,695 A | 5/1993 | Trout, III |
| 5,226,429 A | 7/1993 | Kuzmak |
| 5,234,454 A | 8/1993 | Bangs |
| 5,236,423 A | 8/1993 | Mix et al. |
| 5,246,456 A | 9/1993 | Wilkinson |
| 5,254,133 A | 10/1993 | Seid |
| 5,279,553 A | 1/1994 | Winkler et al. |
| 5,282,824 A | 2/1994 | Gianturco |
| 5,290,294 A | 3/1994 | Cox et al. |
| 5,306,300 A | 4/1994 | Berry |
| 5,314,444 A | 5/1994 | Gianturco |
| 5,314,472 A | 5/1994 | Fontaine |
| 5,314,473 A | 5/1994 | Godin |
| 5,318,530 A | 6/1994 | Nelson, Jr. |
| 5,322,501 A | 6/1994 | Mahmud-Durrani |
| 5,330,500 A | 7/1994 | Song |
| 5,364,353 A | 11/1994 | Corfitsen et al. |
| 5,387,235 A | 2/1995 | Chuter |
| 5,389,090 A | 2/1995 | Fischell et al. |
| 5,401,241 A | 3/1995 | Delany |
| 5,405,378 A | 4/1995 | Strecker |
| 5,417,697 A | 5/1995 | Wilk et al. |
| 5,443,498 A | 8/1995 | Fontaine |
| 5,456,713 A | 10/1995 | Chuter |
| 5,458,605 A | 10/1995 | Klemm |
| 5,458,615 A | 10/1995 | Klemm |
| 5,476,506 A | 12/1995 | Lunn |
| 5,480,423 A | 1/1996 | Ravenscroft et al. |
| 5,492,530 A | 2/1996 | Fischell et al. |
| 5,507,767 A | 4/1996 | Maeda et al. |
| 5,507,771 A | 4/1996 | Gianturco |
| 5,522,880 A | 6/1996 | Barone et al. |
| 5,562,697 A | 10/1996 | Christiansen |
| 5,562,728 A | 10/1996 | Lazarus et al. |
| 5,569,219 A | 10/1996 | Hakki et al. |
| 5,571,173 A | 11/1996 | Parodi |
| 5,605,530 A | 2/1997 | Fischell et al. |
| 5,607,442 A | 3/1997 | Fischell et al. |
| 5,611,787 A | 3/1997 | Demeter et al. |
| 5,620,763 A | 4/1997 | House et al. |
| 5,624,430 A | 4/1997 | Eton et al. |
| 5,630,797 A | 5/1997 | Diedrich et al. |
| 5,634,928 A | 6/1997 | Fischell et al. |
| 5,639,274 A | 6/1997 | Fischell et al. |
| 5,643,312 A | 7/1997 | Fischell et al. |
| 5,662,585 A | 9/1997 | Willis et al. |
| 5,662,713 A | 9/1997 | Andersen et al. |
| 5,665,064 A | 9/1997 | Bodicky et al. |
| 5,669,932 A | 9/1997 | Fischell et al. |
| 5,683,451 A | 11/1997 | Lenker et al. |
| 5,690,642 A | 11/1997 | Osborne et al. |
| 5,693,084 A | 12/1997 | Chuter |
| 5,695,516 A | 12/1997 | Fischell et al. |
| 5,697,971 A | 12/1997 | Fischell et al. |
| 5,713,948 A | 2/1998 | Uflacker |
| 5,715,832 A | 2/1998 | Koblish et al. |
| 5,718,973 A | 2/1998 | Lewis et al. |
| 5,720,776 A | 2/1998 | Chuter et al. |
| 5,722,984 A | 3/1998 | Fischell et al. |
| 5,730,698 A | 3/1998 | Fischell et al. |
| 5,733,325 A | 3/1998 | Robinson et al. |
| 5,735,859 A | 4/1998 | Fischell et al. |
| 5,735,892 A | 4/1998 | Myers et al. |
| 5,741,292 A | 4/1998 | Mendius |
| 5,743,874 A | 4/1998 | Fischell et al. |
| 5,746,692 A | 5/1998 | Bacich et al. |
| 5,749,825 A | 5/1998 | Fischell et al. |
| 5,749,848 A | 5/1998 | Jang et al. |
| 5,755,777 A | 5/1998 | Chuter |
| 5,759,174 A | 6/1998 | Fischell et al. |
| 5,769,887 A | 6/1998 | Brown et al. |
| 5,772,668 A | 6/1998 | Summers et al. |
| 5,776,186 A | 7/1998 | Uflacker |
| 5,792,144 A | 8/1998 | Fischell et al. |
| 5,792,172 A | 8/1998 | Fischell et al. |
| 5,800,381 A | 9/1998 | Ognier |

(56) References Cited

U.S. PATENT DOCUMENTS

| | | |
|---|---|---|
| 5,800,456 A | 9/1998 | Maeda et al. |
| 5,800,526 A | 9/1998 | Anderson et al. |
| 5,820,584 A | 10/1998 | Crabb |
| 5,824,041 A | 10/1998 | Lenker et al. |
| 5,824,058 A | 10/1998 | Ravenscroft et al. |
| 5,824,071 A | 10/1998 | Nelson et al. |
| 5,830,229 A | 11/1998 | Konya et al. |
| 5,833,707 A | 11/1998 | McIntyre et al. |
| 5,840,009 A | 11/1998 | Fischell et al. |
| 5,843,164 A | 12/1998 | Frantzen et al. |
| 5,855,601 A | 1/1999 | Bessler et al. |
| 5,876,445 A | 3/1999 | Andersen et al. |
| 5,879,282 A | 3/1999 | Fischell et al. |
| 5,879,370 A | 3/1999 | Fischell et al. |
| 5,895,391 A | 4/1999 | Farnholtz |
| 5,910,145 A | 6/1999 | Fischell et al. |
| 5,913,895 A | 6/1999 | Burpee et al. |
| 5,919,225 A | 7/1999 | Lau et al. |
| 5,919,233 A | 7/1999 | Knopf et al. |
| 5,925,063 A | 7/1999 | Khosravi |
| 5,925,076 A | 7/1999 | Inoue |
| 5,935,161 A | 8/1999 | Robinson et al. |
| 5,962,620 A | 10/1999 | Reich et al. |
| 5,963,620 A | 10/1999 | Frankel et al. |
| 5,964,771 A | 10/1999 | Beyar et al. |
| 5,976,153 A | 11/1999 | Fischell et al. |
| 5,984,964 A | 11/1999 | Roberts et al. |
| 5,989,280 A | 11/1999 | Euteneuer et al. |
| 6,013,019 A | 1/2000 | Fischell et al. |
| 6,013,085 A | 1/2000 | Howard |
| 6,025,044 A | 2/2000 | Campbell et al. |
| 6,027,508 A | 2/2000 | Ren et al. |
| 6,027,526 A | 2/2000 | Limon et al. |
| 6,035,856 A | 3/2000 | LaFontaine et al. |
| 6,074,673 A | 6/2000 | Guillen |
| 6,077,297 A | 6/2000 | Robinson et al. |
| 6,086,604 A | 7/2000 | Fischell et al. |
| 6,099,552 A | 8/2000 | Adams |
| 6,102,887 A | 8/2000 | Altman |
| 6,113,607 A | 9/2000 | Lau et al. |
| 6,120,533 A | 9/2000 | Fischell |
| 6,120,534 A | 9/2000 | Ruiz |
| 6,121,341 A | 9/2000 | Sawhney et al. |
| 6,132,471 A | 10/2000 | Johlin, Jr. |
| 6,139,572 A | 10/2000 | Campbell et al. |
| 6,146,323 A | 11/2000 | Fischell |
| 6,152,956 A | 11/2000 | Pierce |
| 6,179,868 B1 | 1/2001 | Burpee et al. |
| 6,187,016 B1 | 2/2001 | Hedges et al. |
| 6,190,403 B1 | 2/2001 | Fischell et al. |
| 6,200,336 B1 | 3/2001 | Pavcnik et al. |
| 6,221,043 B1 | 4/2001 | Fischell et al. |
| 6,221,102 B1 | 4/2001 | Baker et al. |
| 6,241,738 B1 | 6/2001 | Dereume |
| 6,241,757 B1 | 6/2001 | An et al. |
| 6,245,097 B1 | 6/2001 | Inoue |
| 6,251,064 B1 | 6/2001 | Silverman et al. |
| 6,251,132 B1 | 6/2001 | Ravenscroft et al. |
| 6,254,629 B1 | 7/2001 | Inoue |
| 6,270,521 B1 | 8/2001 | Fischell et al. |
| 6,273,917 B1 | 8/2001 | Inoue |
| 6,287,335 B1 | 9/2001 | Drasler et al. |
| 6,293,960 B1 | 9/2001 | Ken |
| 6,302,891 B1 | 10/2001 | Nadal |
| 6,302,917 B1 | 10/2001 | Dua et al. |
| 6,315,708 B1 | 11/2001 | Salmon et al. |
| 6,322,538 B1 | 11/2001 | Elbert et al. |
| 6,331,190 B1 | 12/2001 | Shokoohi et al. |
| 6,332,877 B1 | 12/2001 | Michels |
| 6,355,056 B1 | 3/2002 | Pinheiro |
| 6,356,782 B1 | 3/2002 | Sirimanne et al. |
| 6,358,275 B1 | 3/2002 | McIlroy et al. |
| 6,375,660 B1 | 4/2002 | Fischell et al. |
| 6,383,214 B1 | 5/2002 | Banas et al. |
| 6,387,114 B2 | 5/2002 | Adams |
| 6,387,977 B1 | 5/2002 | Sawhney et al. |
| 6,401,718 B1 | 6/2002 | Johnson et al. |
| 6,402,779 B1 | 6/2002 | Colone et al. |
| 6,406,792 B1 | 6/2002 | Briquet et al. |
| 6,428,558 B1 | 8/2002 | Jones et al. |
| 6,450,989 B2 | 9/2002 | Dubrul et al. |
| 6,458,074 B1 | 10/2002 | Matsui et al. |
| 6,468,298 B1 | 10/2002 | Pelton |
| 6,485,409 B1 | 11/2002 | Voloshin et al. |
| 6,485,515 B2 | 11/2002 | Strecker |
| 6,508,833 B2 | 1/2003 | Pavcnik et al. |
| 6,514,282 B1 | 2/2003 | Inoue |
| 6,520,985 B1 | 2/2003 | Burpee et al. |
| 6,520,986 B2 | 2/2003 | Martin et al. |
| 6,524,268 B2 | 2/2003 | Hayner et al. |
| 6,524,335 B1 | 2/2003 | Hartley et al. |
| 6,524,336 B1 | 2/2003 | Papazolgou et al. |
| 6,530,951 B1 | 3/2003 | Bates et al. |
| 6,537,247 B2 | 3/2003 | Shannon |
| 6,540,775 B1 | 4/2003 | Fischell et al. |
| 6,540,789 B1 | 4/2003 | Silverman et al. |
| 6,544,291 B2 | 4/2003 | Taylor |
| 6,547,817 B1 | 4/2003 | Fischell et al. |
| 6,558,400 B2 | 5/2003 | Deem et al. |
| 6,558,429 B2 | 5/2003 | Taylor |
| 6,565,597 B1 | 5/2003 | Fearnot et al. |
| 6,569,181 B1 | 5/2003 | Burns |
| 6,572,646 B1 | 6/2003 | Boylan et al. |
| 6,582,460 B1 | 6/2003 | Cryer |
| 6,585,756 B1 | 7/2003 | Strecker |
| 6,589,213 B2 | 7/2003 | Reydel |
| 6,589,275 B1 | 7/2003 | Ivancev et al. |
| 6,613,072 B2 | 9/2003 | Lau et al. |
| 6,623,518 B2 | 9/2003 | Thompson et al. |
| 6,635,069 B1 | 10/2003 | Teoh et al. |
| 6,635,079 B2 | 10/2003 | Unsworth et al. |
| 6,645,239 B1 | 11/2003 | Park et al. |
| 6,652,555 B1 | 11/2003 | VanTassel et al. |
| 6,656,194 B1 | 12/2003 | Gannoe et al. |
| 6,656,212 B2 | 12/2003 | Ravenscroft et al. |
| 6,669,722 B2 | 12/2003 | Chen et al. |
| 6,673,339 B1 | 1/2004 | Atala et al. |
| 6,675,809 B2 | 1/2004 | Stack et al. |
| 6,676,692 B2 | 1/2004 | Rabkin et al. |
| 6,695,875 B2 | 2/2004 | Stelter et al. |
| 6,699,263 B2 | 3/2004 | Cope |
| 6,699,278 B2 | 3/2004 | Fischell et al. |
| 6,706,061 B1 | 3/2004 | Fischell et al. |
| 6,716,240 B2 | 4/2004 | Fischell et al. |
| 6,736,840 B2 | 5/2004 | Fischell et al. |
| 6,740,121 B2 | 5/2004 | Geitz |
| 6,755,869 B2 | 6/2004 | Geitz |
| 6,761,733 B2 | 7/2004 | Chobotov et al. |
| 6,764,518 B2 | 7/2004 | Godin |
| 6,773,440 B2 | 8/2004 | Gannoe et al. |
| 6,776,791 B1 | 8/2004 | Stallings et al. |
| 6,802,868 B2 | 10/2004 | Silverman et al. |
| 6,821,291 B2 | 11/2004 | Bolea et al. |
| 6,845,776 B2 | 1/2005 | Stack et al. |
| 6,849,087 B1 | 2/2005 | Chuter |
| 6,855,159 B1 | 2/2005 | Tanner et al. |
| 6,860,899 B1 | 3/2005 | Rivelli, Jr. |
| 6,860,901 B1 | 3/2005 | Baker et al. |
| 6,918,871 B2 | 7/2005 | Schulze |
| 6,926,658 B2 | 8/2005 | Farnan |
| 6,936,065 B2 | 8/2005 | Khan et al. |
| 6,960,233 B1 | 11/2005 | Berg et al. |
| 6,989,024 B2 | 1/2006 | Hebert et al. |
| 7,011,654 B2 | 3/2006 | Dubrul et al. |
| 7,011,671 B2 | 3/2006 | Welch |
| 7,011,673 B2 | 3/2006 | Fischell et al. |
| 7,025,791 B2 | 4/2006 | Levine et al. |
| 7,033,384 B2 | 4/2006 | Gannoe et al. |
| 7,037,327 B2 | 5/2006 | Salmon et al. |
| 7,037,344 B2 | 5/2006 | Kagan et al. |
| 7,054,690 B2 | 5/2006 | Imran |
| 7,066,951 B2 | 6/2006 | Chobotov |
| 7,081,132 B2 | 7/2006 | Cook et al. |
| 7,087,088 B2 | 8/2006 | Berg et al. |

(56) References Cited

U.S. PATENT DOCUMENTS

| | | |
|---|---|---|
| 7,111,627 B2 | 9/2006 | Stack et al. |
| 7,121,283 B2 | 10/2006 | Stack et al. |
| 7,122,058 B2 | 10/2006 | Levine et al. |
| 7,146,984 B2 | 12/2006 | Stack et al. |
| 7,147,865 B2 | 12/2006 | Fishman et al. |
| 7,152,607 B2 | 12/2006 | Stack et al. |
| 7,160,312 B2 | 1/2007 | Saadat |
| 7,175,660 B2 | 2/2007 | Cartledge et al. |
| 7,211,114 B2 | 5/2007 | Bessler et al. |
| 7,220,237 B2 | 5/2007 | Gannoe et al. |
| 7,220,284 B2 | 5/2007 | Kagan et al. |
| 7,229,428 B2 | 6/2007 | Gannoe et al. |
| 7,267,694 B2 | 9/2007 | Levine et al. |
| 7,314,489 B2 * | 1/2008 | McKenna ............ A61F 5/0076 604/523 |
| 7,316,716 B2 | 1/2008 | Egan |
| 7,329,285 B2 | 2/2008 | Levine et al. |
| 7,335,224 B2 | 2/2008 | Øhlenschlæger |
| 7,338,518 B2 | 3/2008 | Chobotov |
| 7,338,520 B2 | 3/2008 | Bailey et al. |
| 7,347,875 B2 | 3/2008 | Levine et al. |
| 7,354,454 B2 | 4/2008 | Stack et al. |
| 7,476,256 B2 * | 1/2009 | Meade ................ A61B 17/0401 623/23.64 |
| 7,488,344 B2 | 2/2009 | Hartley et al. |
| 7,507,218 B2 | 3/2009 | Aliski et al. |
| 7,513,914 B2 | 4/2009 | Schurr |
| 7,608,114 B2 | 10/2009 | Levine et al. |
| 7,611,528 B2 | 11/2009 | Goodson, IV et al. |
| 7,621,886 B2 | 11/2009 | Burnett |
| 7,678,068 B2 | 3/2010 | Levine et al. |
| 7,682,330 B2 | 3/2010 | Meade et al. |
| 7,695,446 B2 | 4/2010 | Levine et al. |
| 7,758,535 B2 | 7/2010 | Levine et al. |
| 7,766,861 B2 | 8/2010 | Levine et al. |
| 7,766,973 B2 | 8/2010 | Levine et al. |
| 7,785,361 B2 | 8/2010 | Nikolchev et al. |
| 7,794,487 B2 | 9/2010 | Majercak et al. |
| 7,803,177 B2 | 9/2010 | Hartley et al. |
| 7,815,589 B2 * | 10/2010 | Meade ................ A61B 17/0401 604/8 |
| 7,815,671 B2 | 10/2010 | Wright et al. |
| 7,819,836 B2 | 10/2010 | Levine et al. |
| 7,837,643 B2 | 11/2010 | Levine et al. |
| 7,862,609 B2 | 1/2011 | Butaric et al. |
| 7,881,797 B2 | 2/2011 | Griffin et al. |
| 7,892,214 B2 | 2/2011 | Kagan et al. |
| 7,935,073 B2 | 5/2011 | Levine et al. |
| 7,981,163 B2 | 7/2011 | Meade et al. |
| 8,092,510 B2 | 1/2012 | Metcalf et al. |
| 8,096,966 B2 | 1/2012 | Levine et al. |
| 8,109,895 B2 | 2/2012 | Williams et al. |
| 8,137,301 B2 * | 3/2012 | Levine ............... A61B 17/0401 604/8 |
| 8,142,490 B2 | 3/2012 | Rice et al. |
| 8,162,871 B2 | 4/2012 | Levine et al. |
| 8,303,669 B2 | 11/2012 | Meade et al. |
| 8,317,859 B2 | 11/2012 | Snow et al. |
| 8,333,797 B2 | 12/2012 | Goodson, IV et al. |
| 8,486,137 B2 | 7/2013 | Suri et al. |
| 8,486,153 B2 * | 7/2013 | Levine ............... A61B 17/0401 623/23.65 |
| 8,568,472 B2 | 10/2013 | Marchand et al. |
| 8,579,954 B2 | 11/2013 | Licata |
| 8,579,961 B2 | 11/2013 | Casey, II et al. |
| 8,628,583 B2 | 1/2014 | Meade et al. |
| 8,834,405 B2 | 9/2014 | Meade et al. |
| 8,870,806 B2 | 10/2014 | Levine et al. |
| 9,084,669 B2 | 7/2015 | Meade et al. |
| 9,155,608 B2 | 10/2015 | Blaeser |
| 9,155,609 B2 | 10/2015 | Levine et al. |
| 9,237,944 B2 * | 1/2016 | Meade ................ A61B 17/0401 |
| 9,278,020 B2 | 3/2016 | Levine et al. |
| 2001/0020190 A1 | 9/2001 | Taylor |
| 2002/0022853 A1 | 2/2002 | Swanson et al. |
| 2002/0032487 A1 | 3/2002 | Dua et al. |
| 2002/0065545 A1 | 5/2002 | Leonhardt et al. |
| 2002/0091439 A1 | 7/2002 | Baker et al. |
| 2002/0099439 A1 | 7/2002 | Schwartz et al. |
| 2002/0107565 A1 | 8/2002 | Greenhalgh |
| 2002/0120277 A1 | 8/2002 | Hauschild et al. |
| 2002/0143387 A1 | 10/2002 | Soetikno et al. |
| 2002/0147489 A1 | 10/2002 | Hong et al. |
| 2002/0151953 A1 | 10/2002 | Chobotov et al. |
| 2002/0155100 A1 | 10/2002 | Kieffer et al. |
| 2002/0177890 A1 | 11/2002 | Lenker |
| 2002/0183768 A1 | 12/2002 | Deem et al. |
| 2002/0183786 A1 | 12/2002 | Girton |
| 2002/0188344 A1 | 12/2002 | Bolea et al. |
| 2002/0193828 A1 | 12/2002 | Griffin et al. |
| 2003/0009236 A1 | 1/2003 | Godin |
| 2003/0032941 A1 | 2/2003 | Boyle et al. |
| 2003/0040804 A1 | 2/2003 | Stack et al. |
| 2003/0040808 A1 | 2/2003 | Stack et al. |
| 2003/0050684 A1 | 3/2003 | Abrams et al. |
| 2003/0055492 A1 | 3/2003 | Shaolian et al. |
| 2003/0069539 A1 | 4/2003 | Gandhi et al. |
| 2003/0074051 A1 | 4/2003 | Freislinger-Luehrs |
| 2003/0109892 A1 | 6/2003 | Deem et al. |
| 2003/0109931 A1 | 6/2003 | Geitz |
| 2003/0109935 A1 | 6/2003 | Geitz |
| 2003/0120265 A1 | 6/2003 | Deem et al. |
| 2003/0149467 A1 | 8/2003 | Linder et al. |
| 2003/0153927 A1 | 8/2003 | DiPoto et al. |
| 2003/0154986 A1 | 8/2003 | Fariss et al. |
| 2003/0191476 A1 | 10/2003 | Smit |
| 2003/0199989 A1 | 10/2003 | Stack et al. |
| 2003/0199990 A1 | 10/2003 | Stack et al. |
| 2003/0199991 A1 | 10/2003 | Stack et al. |
| 2003/0208260 A1 | 11/2003 | Lau et al. |
| 2003/0216749 A1 | 11/2003 | Ishikawa et al. |
| 2003/0225445 A1 | 12/2003 | Derus et al. |
| 2003/0233140 A1 | 12/2003 | Hartley et al. |
| 2004/0019388 A1 | 1/2004 | Starkebaum |
| 2004/0024386 A1 | 2/2004 | Deem et al. |
| 2004/0037865 A1 | 2/2004 | Miller |
| 2004/0039452 A1 | 2/2004 | Bessler |
| 2004/0044357 A1 | 3/2004 | Gannoe et al. |
| 2004/0082963 A1 | 4/2004 | Gannoe et al. |
| 2004/0092892 A1 | 5/2004 | Kagan et al. |
| 2004/0092974 A1 | 5/2004 | Gannoe et al. |
| 2004/0093063 A1 | 5/2004 | Wright et al. |
| 2004/0093065 A1 | 5/2004 | Yachia et al. |
| 2004/0098079 A1 | 5/2004 | Hartley et al. |
| 2004/0107004 A1 | 6/2004 | Levine et al. |
| 2004/0117004 A1 | 6/2004 | Osborne et al. |
| 2004/0117031 A1 | 6/2004 | Stack et al. |
| 2004/0122452 A1 | 6/2004 | Deem et al. |
| 2004/0122453 A1 | 6/2004 | Deem et al. |
| 2004/0122470 A1 | 6/2004 | Deem et al. |
| 2004/0133147 A1 | 7/2004 | Woo |
| 2004/0136971 A1 | 7/2004 | Scharp et al. |
| 2004/0138525 A1 | 7/2004 | Saadat et al. |
| 2004/0138529 A1 | 7/2004 | Wiltshire et al. |
| 2004/0138760 A1 | 7/2004 | Schurr |
| 2004/0138761 A1 | 7/2004 | Stack et al. |
| 2004/0143342 A1 | 7/2004 | Stack et al. |
| 2004/0148034 A1 | 7/2004 | Kagan et al. |
| 2004/0151740 A1 | 8/2004 | Aoki et al. |
| 2004/0153167 A1 | 8/2004 | Stack et al. |
| 2004/0158229 A1 | 8/2004 | Quinn |
| 2004/0158331 A1 | 8/2004 | Stack et al. |
| 2004/0172063 A1 | 9/2004 | Li et al. |
| 2004/0172088 A1 | 9/2004 | Knudson et al. |
| 2004/0172141 A1 | 9/2004 | Stack et al. |
| 2004/0172142 A1 * | 9/2004 | Stack ........................ A61F 2/04 623/23.65 |
| 2004/0172143 A1 | 9/2004 | Geitz |
| 2004/0181242 A1 | 9/2004 | Stack et al. |
| 2004/0193093 A1 | 9/2004 | Desmond, III |
| 2004/0193261 A1 | 9/2004 | Berreklouw |
| 2004/0210243 A1 | 10/2004 | Gannoe et al. |
| 2004/0220682 A1 | 11/2004 | Levine et al. |

(56) References Cited

U.S. PATENT DOCUMENTS

| | | |
|---|---|---|
| 2004/0236363 A1 | 11/2004 | Kieturakis et al. |
| 2004/0236401 A1 | 11/2004 | Shin et al. |
| 2004/0249362 A1 | 12/2004 | Levine et al. |
| 2005/0004681 A1 | 1/2005 | Stack et al. |
| 2005/0033331 A1 | 2/2005 | Burnett et al. |
| 2005/0043601 A1 | 2/2005 | Kilcoyne et al. |
| 2005/0043817 A1 | 2/2005 | McKenna et al. |
| 2005/0049718 A1 | 3/2005 | Dann et al. |
| 2005/0055039 A1 | 3/2005 | Burnett et al. |
| 2005/0060017 A1 | 3/2005 | Fischell et al. |
| 2005/0075622 A1 | 4/2005 | Levine et al. |
| 2005/0080395 A1 | 4/2005 | Levine et al. |
| 2005/0080431 A1 | 4/2005 | Levine et al. |
| 2005/0080480 A1 | 4/2005 | Bolea et al. |
| 2005/0080491 A1 | 4/2005 | Levine et al. |
| 2005/0085787 A1 | 4/2005 | Laufer |
| 2005/0085923 A1 | 4/2005 | Levine et al. |
| 2005/0090873 A1 | 4/2005 | Imran |
| 2005/0096725 A1 | 5/2005 | Pomeranz et al. |
| 2005/0096750 A1 | 5/2005 | Kagan et al. |
| 2005/0107862 A1 | 5/2005 | Ohlenschlaeger |
| 2005/0111072 A1 | 5/2005 | Miyagaki et al. |
| 2005/0125020 A1 | 6/2005 | Meade et al. |
| 2005/0125075 A1 | 6/2005 | Meade et al. |
| 2005/0149114 A1 | 7/2005 | Cartledge et al. |
| 2005/0171556 A1 | 8/2005 | Murphy |
| 2005/0182481 A1 | 8/2005 | Schlick et al. |
| 2005/0182483 A1 | 8/2005 | Osborne et al. |
| 2005/0192614 A1 | 9/2005 | Binmoeller |
| 2005/0216040 A1 | 9/2005 | Gertner et al. |
| 2005/0216042 A1 | 9/2005 | Gertner |
| 2005/0221072 A1 | 10/2005 | Dubrow et al. |
| 2005/0228415 A1 | 10/2005 | Gertner |
| 2005/0228504 A1 | 10/2005 | Demarais |
| 2005/0240279 A1 | 10/2005 | Kagan et al. |
| 2005/0256587 A1 | 11/2005 | Egan |
| 2005/0267405 A1 | 12/2005 | Shah |
| 2005/0267499 A1 | 12/2005 | Stack et al. |
| 2005/0267533 A1 | 12/2005 | Gertner |
| 2005/0273060 A1 | 12/2005 | Levy et al. |
| 2005/0283107 A1 | 12/2005 | Kalanovic et al. |
| 2006/0009858 A1 | 1/2006 | Levine et al. |
| 2006/0064120 A1 | 3/2006 | Levine et al. |
| 2006/0106332 A1 | 5/2006 | Knudson et al. |
| 2006/0142836 A1 | 6/2006 | Hartley et al. |
| 2006/0155312 A1 | 7/2006 | Levine et al. |
| 2006/0161139 A1 | 7/2006 | Levine et al. |
| 2006/0161172 A1 | 7/2006 | Levine et al. |
| 2006/0161187 A1 | 7/2006 | Levine et al. |
| 2006/0161265 A1 | 7/2006 | Levine et al. |
| 2006/0212042 A1 | 9/2006 | Lamport et al. |
| 2006/0265082 A1 | 11/2006 | Meade et al. |
| 2006/0271166 A1 | 11/2006 | Thill et al. |
| 2006/0271175 A1 | 11/2006 | Woolfson et al. |
| 2006/0287734 A1 | 12/2006 | Stack et al. |
| 2007/0005147 A1 | 1/2007 | Levine et al. |
| 2007/0010794 A1 | 1/2007 | Dann et al. |
| 2007/0010864 A1 | 1/2007 | Dann et al. |
| 2007/0026042 A1 | 2/2007 | Narayanan |
| 2007/0027548 A1 | 2/2007 | Levine et al. |
| 2007/0032879 A1 | 2/2007 | Levine et al. |
| 2007/0049801 A1 | 3/2007 | Lamport et al. |
| 2007/0083258 A1 | 4/2007 | Falotico et al. |
| 2007/0083271 A1 | 4/2007 | Levine et al. |
| 2007/0173787 A1 | 7/2007 | Huang et al. |
| 2007/0276432 A1 | 11/2007 | Stack et al. |
| 2007/0282453 A1 | 12/2007 | Weitzner et al. |
| 2007/0282454 A1 | 12/2007 | Krueger et al. |
| 2007/0293885 A1 | 12/2007 | Binmoeller |
| 2008/0058772 A1 | 3/2008 | Robertson et al. |
| 2008/0065136 A1 | 3/2008 | Young |
| 2008/0071383 A1 | 3/2008 | Levine et al. |
| 2008/0097466 A1 | 4/2008 | Levine et al. |
| 2008/0103604 A1 | 5/2008 | Levine et al. |
| 2008/0172072 A1 | 7/2008 | Pool |
| 2008/0208239 A1 | 8/2008 | Annunziata |
| 2008/0208240 A1 | 8/2008 | Paz |
| 2008/0208357 A1 | 8/2008 | Melanson et al. |
| 2008/0221556 A1 | 9/2008 | Johnson et al. |
| 2008/0221575 A1 | 9/2008 | Betts |
| 2008/0221597 A1 | 9/2008 | Wallace |
| 2008/0221702 A1 | 9/2008 | Wallace |
| 2008/0223476 A1 | 9/2008 | Stinson |
| 2008/0234834 A1 | 9/2008 | Meade et al. |
| 2008/0293885 A1 | 11/2008 | Morimoto et al. |
| 2009/0012544 A1 | 1/2009 | Thompson |
| 2009/0012553 A1 | 1/2009 | Swain et al. |
| 2009/0024077 A1 | 1/2009 | Zeiner et al. |
| 2009/0062717 A1 | 3/2009 | Laufer |
| 2009/0240340 A1 | 9/2009 | Levine et al. |
| 2009/0248171 A1 | 10/2009 | Levine et al. |
| 2009/0281563 A1 | 11/2009 | Newell et al. |
| 2010/0114130 A1 | 5/2010 | Meade et al. |
| 2010/0256775 A1 | 10/2010 | Belhe et al. |
| 2010/0256776 A1 | 10/2010 | Levine et al. |
| 2010/0331756 A1 | 12/2010 | Meade et al. |
| 2011/0106273 A1 | 5/2011 | Belhe |
| 2011/0245752 A1 | 10/2011 | Levine et al. |
| 2011/0257580 A1 | 10/2011 | Meade et al. |
| 2011/0264234 A1 | 10/2011 | Baker |
| 2011/0276091 A1 | 11/2011 | Melanson et al. |
| 2012/0179086 A1 | 7/2012 | Shank et al. |
| 2012/0184893 A1 | 7/2012 | Thompson |
| 2012/0184967 A1 | 7/2012 | Levine et al. |
| 2012/0209370 A1 | 8/2012 | Thill et al. |
| 2012/0215152 A1 | 8/2012 | Levine et al. |
| 2013/0012862 A1 | 1/2013 | Meade et al. |
| 2013/0331759 A1 | 12/2013 | Neisz |
| 2014/0100512 A1 | 4/2014 | Meade |
| 2014/0194805 A1 | 7/2014 | Levine et al. |
| 2014/0303543 A1 | 10/2014 | Meade |
| 2014/0350694 A1 | 11/2014 | Bchan |
| 2015/0238305 A1 | 8/2015 | Meade et al. |
| 2016/0058544 A1 | 3/2016 | Levine et al. |

FOREIGN PATENT DOCUMENTS

| | | |
|---|---|---|
| EP | 0278937 B1 | 10/1993 |
| EP | 0 423 916 | 4/1994 |
| EP | 0 686 379 A2 | 12/1995 |
| EP | 0 506 918 B1 | 1/1996 |
| EP | 0754017 B1 | 1/1997 |
| EP | 0843538 B1 | 5/1998 |
| EP | 0 857 471 A2 | 8/1998 |
| EP | 0935977 A2 | 8/1999 |
| EP | 0935977 A3 | 8/1999 |
| EP | 1 481 649 A1 | 12/2004 |
| EP | 1 504 778 A3 | 2/2005 |
| EP | 1 504 778 A2 | 3/2005 |
| EP | 1 772 115 | 4/2007 |
| JP | 04212348 | 8/1992 |
| JP | 05-305092 A | 11/1993 |
| JP | 08-052165 A | 2/1996 |
| JP | 2000-126304 | 5/2000 |
| JP | 2002-503114 A | 1/2002 |
| JP | 2002-531169 A | 9/2002 |
| WO | WO 92/06734 A1 | 4/1992 |
| WO | WO 95/05132 | 2/1995 |
| WO | WO 96/18361 | 6/1996 |
| WO | WO 97/03624 A1 | 2/1997 |
| WO | WO 98/08456 | 3/1998 |
| WO | WO 98/22045 | 5/1998 |
| WO | WO 99/23953 | 5/1999 |
| WO | WO 99/44536 | 9/1999 |
| WO | WO 00/12027 | 3/2000 |
| WO | WO 00/28922 A1 | 5/2000 |
| WO | WO 00/32137 | 6/2000 |
| WO | WO 00/42945 A1 | 7/2000 |
| WO | WO 00/42949 | 7/2000 |
| WO | WO 00/59405 A1 | 10/2000 |
| WO | WO 01/12256 A1 | 2/2001 |
| WO | WO 01/35861 A1 | 5/2001 |
| WO | WO 01/45485 A2 | 6/2001 |
| WO | WO 02/081019 A1 | 10/2002 |

(56) References Cited

FOREIGN PATENT DOCUMENTS

| | | |
|---|---|---|
| WO | WO 02/096327 A2 | 12/2002 |
| WO | WO 03/017882 A2 | 3/2003 |
| WO | WO 03/086246 A1 | 10/2003 |
| WO | WO 03/086247 A1 | 10/2003 |
| WO | WO 03/086360 A1 | 10/2003 |
| WO | WO 03/094785 A1 | 11/2003 |
| WO | WO 04/000169 A1 | 12/2003 |
| WO | WO 2004/004542 A2 | 1/2004 |
| WO | WO 2004/004542 A3 | 1/2004 |
| WO | WO 2004/014237 A1 | 2/2004 |
| WO | WO 2004/019765 A2 | 3/2004 |
| WO | WO 2004/019765 A3 | 3/2004 |
| WO | WO 2004/021894 A1 | 3/2004 |
| WO | WO 2004/037064 A2 | 5/2004 |
| WO | WO 2004/037064 A3 | 5/2004 |
| WO | WO 2004/049982 A2 | 6/2004 |
| WO | WO 2004/064680 A1 | 8/2004 |
| WO | WO 2004/064682 A1 | 8/2004 |
| WO | WO 2004/064685 A1 | 8/2004 |
| WO | WO 2004/069331 A2 | 8/2004 |
| WO | WO 2004/069332 A1 | 8/2004 |
| WO | WO 2004/073782 A1 | 9/2004 |
| WO | WO 2004/080336 | 9/2004 |
| WO | WO 2004/087014 A2 | 10/2004 |
| WO | WO 2004/087233 A2 | 10/2004 |
| WO | WO 2004/093639 A2 | 11/2004 |
| WO | WO 2004/093639 A3 | 11/2004 |
| WO | WO 2005/011533 A1 | 2/2005 |
| WO | WO 2005/060869 A1 | 7/2005 |
| WO | WO 2005/060882 A1 | 7/2005 |
| WO | WO 2005/082296 A1 | 9/2005 |
| WO | WO 2005/110280 A2 | 11/2005 |
| WO | WO 2005/117716 A2 | 12/2005 |
| WO | WO 2005/118049 A1 | 12/2005 |
| WO | WO 2005/120363 | 12/2005 |
| WO | WO 2006/016894 A1 | 2/2006 |
| WO | WO 2006/034062 A1 | 3/2006 |
| WO | WO 2006/078781 A1 | 7/2006 |
| WO | WO 2006/078927 A1 | 7/2006 |
| WO | WO 2006/088578 A1 | 8/2006 |
| WO | WO 2006/102012 A1 | 9/2006 |
| WO | WO 2006/133311 A2 | 12/2006 |

OTHER PUBLICATIONS

Binkert, C. A., et al., "Benign and Malignant Stenoses of the Stomach and Duodenum: Treatment with Self-expanding Metallic Endoprostheses," Radiology 199(2):335-338 (1996).

Choostent™, Covered Esophageal Stent, Instructions, Retrieved from the Internet (http://mitech.co.kr/uploads/images/282/use guide esophachoo_english.pdf) on Jul. 26, 2005.

Cwikiel, W., et al., "Self-expanding Stent in the Treatment of Benign Esophageal Strictures: Experimental Study in Pigs and Presentation of Clinical Cases," Radiology 187(3):667-671 (1993).

Dolan, K. et al., "Treating Diabetes in the Morbidly Obese by Laproscopic Gastric Band," Obesity Surgery, vol. 13, pp. 439-443 (2003).

Dormann, A.J. et al., "Self-expanding metallic stents for continous dilatation of benign stenosis in gastrointestinal tract—first results of long-term follow-up in interim stent application in pyloric and colonic obstructions," Z Gastroenteral 39:957-960 (2001).

Feretis, C., et al., "Palliation of Malignant Gastric Outlet Obstruction with Self-Expanding Metal Stents," Endoscopy 28:225-228 (1996).

Final Office Action for U.S. Appl. No. 12/880,631, dated Apr. 24, 2012 "Methods and Apparatus for Anchoring Within the Gastrointestinal Tract."

Hwang, J.C., et al., "Covered Retrievable Tracheobronchial Hinged Stent: An Experimental Study in Dogs," *J. Vasc. Interv. Radiol.*, 12(12):1429-1436 (Dec. 2001).

Irie, T., et al., "Relocatable Gianturco Expandable Metallic Stents[1]," *Radiology*, 178:575-578 (1991).

Keet, A.D, *The Pyloric Sphincteric Cylinder in Health and Disease*, Springer-Verlag, New York, Chapter 11, p. 44, http://med.plig.org/11, printed from the Internet on Nov. 6, 2009.

Lee, B.H., et al., "New Self-Expandable Spiral Metallic Stent: Preliminary clinical Evaluation in Malignant Biliary Obstruction," *J. Vasc Interv Radiol.*, 6(4):635-640 (Jul. 8, 1995).

Lee, S.H., "The Role of Oesophageal Stenting in the Non-Surgical Management of Oesophageal Strictures," *British J. Radiology*, 74:891-900 (Oct. 2001).

Non-Final Office Action, dated Dec. 16, 2013 for U.S. Appl. No. 13/098,750 "Methods of Treatment Using a Bariatric Sleeve."

Non-Final Office Action, dated Jan. 8, 2014 for U.S. Appl. No. 13/401,258 "Bariatric Sleeve."

Notice of Allowance for U.S. Appl. No. 13/098,750, mailed on Aug. 22, 2014, entitled: Methods of Treatment Using a Bariatric Sleeve.

Notice of Allowance for U.S. Appl. No. 13/170,785, mailed on Jul. 8, 2014, entitled: Intestinal Sleeve.

Notice of Allowance for U.S. Appl. No. 12/454,878, Date Mailed: Nov. 14, 2011 "Bariatric Sleeve."

Notice of Allowance for U.S. Appl. No. 12/454,915, Date Mailed: Nov. 22, 2011 "Bariatric Sleeve."

Notice of Allowance for U.S. Appl. No. 12/880,631, dated Jul. 3, 2012 "Methods and Apparatus for Anchoring Within the Gastrointestinal Tract."

Notice of Allowance for U.S. Appl. No. 14/102,065, entitled "Methods and Apparatus for Anchoring Within the Gastrointestinal Tract", mailed Mar. 25, 2015.

Notice of Allowance of U.S. Appl. No. 11/302,946 dated Dec. 29, 2009 "Methods of Treatment Using a Bariatric Sleeve."

Notice of Allowance, U.S. Appl. No. 13/098,750, dated Jun. 23, 2014 "Intestinal Sleeve".

Office Action dated Jun. 7, 2013 for U.S. Appl. No. 13/618,036 "Methods and Apparatus for Anchoring Within the Gastrointestinal Tract."

Office Action dated May 6, 2011; U.S. Appl. No. 12/454,878 "Bariatric Sleeve."

Office Action dated May 6, 2011; U.S. Appl. No. 12/454,915 "Bariatric Sleeve."

Office Action for U.S. Appl. No. 13/618,036, dated Mar. 4, 2013 "Methods and Apparatus for Anchoring Within the Gastrointestinal Tract."

Office Action for U.S. Appl. No. 11/978,327, Mail Date: Sep. 29, 2010 "Methods of Treatment Using a Bariatric Sleeve".

Office Action for U.S. Appl. No. 14/102,065, entitled "Methods and Apparatus for Anchoring Within the Gastrointestinal Tract", mailed Nov. 18, 2014.

Office Action of U.S. Appl. No. 11/978,327 dated Nov. 20, 2009 "Methods of Treatment Using a Bariatric Sleeve."

Office Action, U.S. Appl. No. 12/880,631, dated Dec. 1, 2011 "Methods and Apparatus for Anchoring Within the Gastrointestinal Tract."

Park, B.P. et al., Malignant Obstruction of Gastric Outlet and Duodenum: Palliation with Flexible Covered Metallic Stents, Radiology 219(3):679-683 (2001).

Parodi, J.C., M.D., "Endovascular Repair of Abdominal Aortic Aneurysms," Advances in Vascular Surgery, vol. 1, pp. 85-105 (1993).

Pories, W.J., "Why Does the Gastric Bypass Control Type 2 Diabetes Mellitus?" Obesity Surgery, 2:303-313 (1992).

Pories, W.J., et al., "Etiology of Type II Diabetes Mellitus: Role of the Foregut," World J. Surg., 25:527-531 (2001).

Rubino, F. and J. Marescaux, "Effect of Duodenal-Jejunal Exclusion in a Non-obese Animal Model of Type 2 Diabetes, A New Perspective for an Old Disease," Annals of Surgery 239(1):1-11, Jan. 2004.

Rubino, F., et al., "Potential of Surgery for Curing Type 2 Diabetes Mellitus," Annals of Surgery 236(5): 554-559 (2002).

Sandha, G. S. and Marcon, N. E., "Expandable Metal Stents for Benign Esophageal Obstruction," Gastrointestinal Endoscopy Clinics of North America 9:(3)437-446 (1999).

Search Report issued in European Patent Application No. 11169684. 5, Date of Search: Sep. 23, 2011, 6 pages "Bariatric Sleeve."

(56) References Cited

OTHER PUBLICATIONS

Shim, C.S., et al., "Fixation of a Modified Covered Esophageal Stent: Its Clinical Usefulness for Preventing Stent Migration," *Endoscopy*, 33(10):843-848 (Oct. 2001).

Song, H.Y., et al., "Benign and Malignant Esophageal Strictures: Treatment with a Polyurethane-Covered Retrievable Expandable Metallic Stent[1]," *Radiology*, 203(3):747-752 (Jun. 1997).

Song, H.Y., et al., "Covered Retrievable Expandable Nitinol Stents in Patients with Benign Esophageal Strictures: Initial Experience[1]," *Radiology*, 217:551-557 (Nov. 2000).

Song, H.Y., et al., "Tracheobronchial Strictures: Treatment with a Polyurethane-Covered Retrievable Expandable Nitinol Stent—Initial Experience," *Radiology*, 213:905-912 (Dec. 1999).

Supplemental Notice of Allowability for U.S. Appl. No. 13/170,785, mailed on Aug. 15, 2014, entitled: Intestinal Sleeve.

Supplemental Notice of Allowance for U.S. Appl. No. 14/102,065, entitled "Methods and Apparatus for Anchoring Within the Gastrointestinal Tract", dated Jun. 19, 2015.

Yates III, M. R., et al., "Palliation of Malignant Gastric and Small Intestinal Strictures With Self-Expandable Metal Stents," Endoscopy 30:266-272 (1998).

Yoon, C.J., et al., "Removal of Retrievable Esophageal and Gastrointestinal Stents: Experience in 113 Patients," *American J. of Roentgenology*, 183:1437-1444 (Nov. 2004).

Notice of Allowance for U.S. Appl. No. 14/515,956, entitled "Methods of Treatment Using a Bariatric Sleeve", dated Oct. 27, 2015.

Non-Final Office Action for U.S. Appl. No. 14/515,956, entitled "Methods of Treatment Using a Bariatric Sleeve", dated Apr. 10, 2015.

Notice of Allowance for U.S. Appl. No. 14/305,518, entitled "Intestinal Sleeve", dated Sep. 9, 2015.

\* cited by examiner

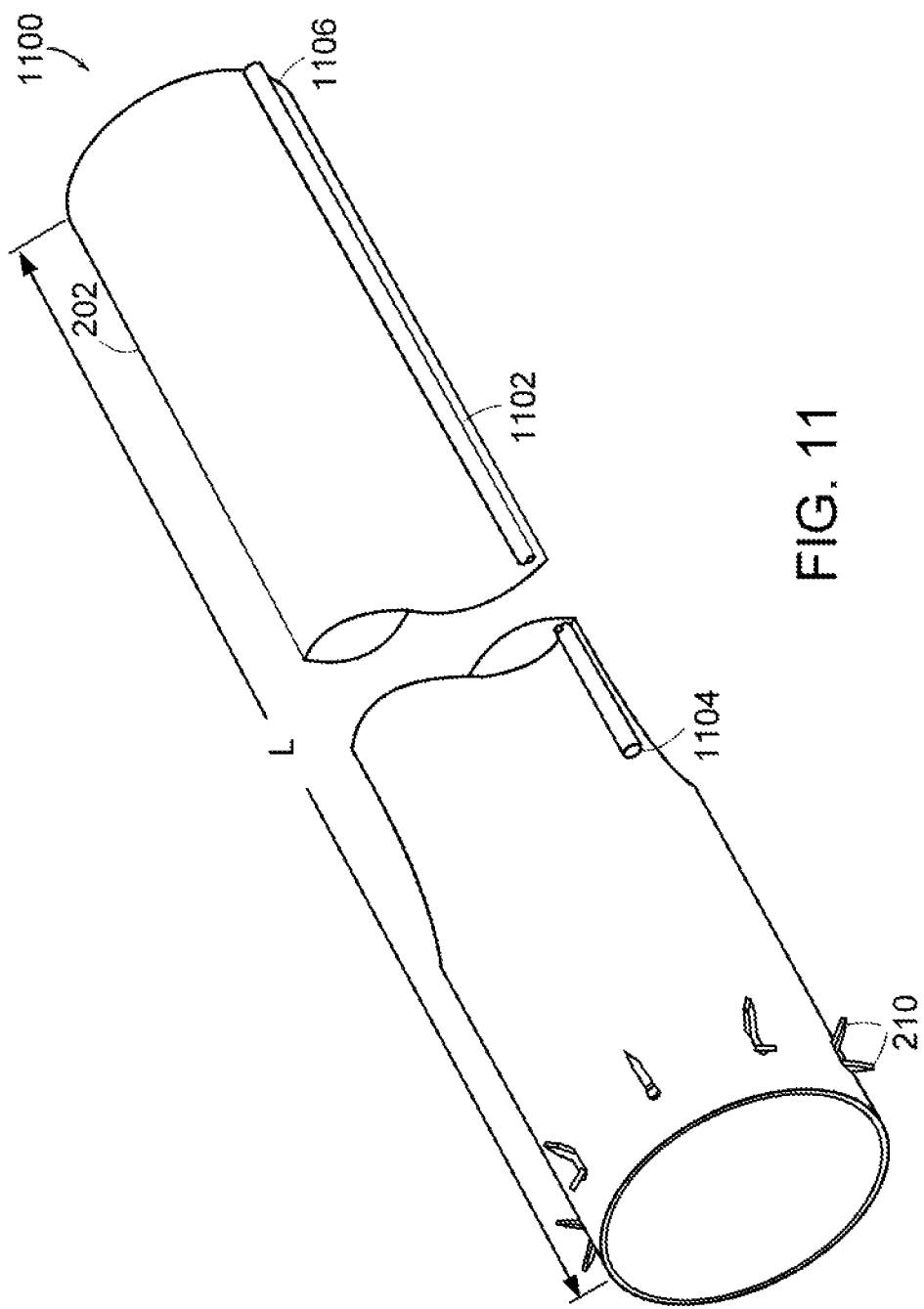

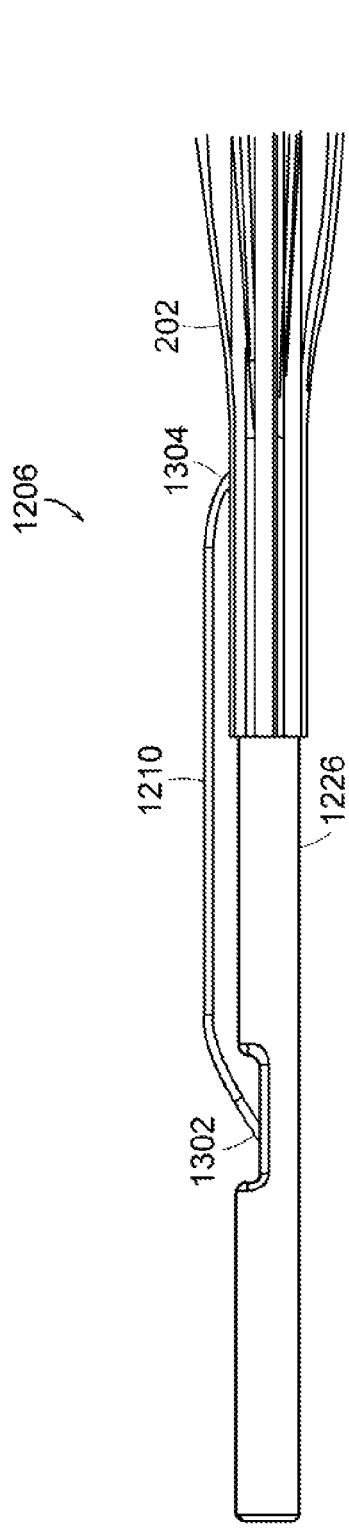
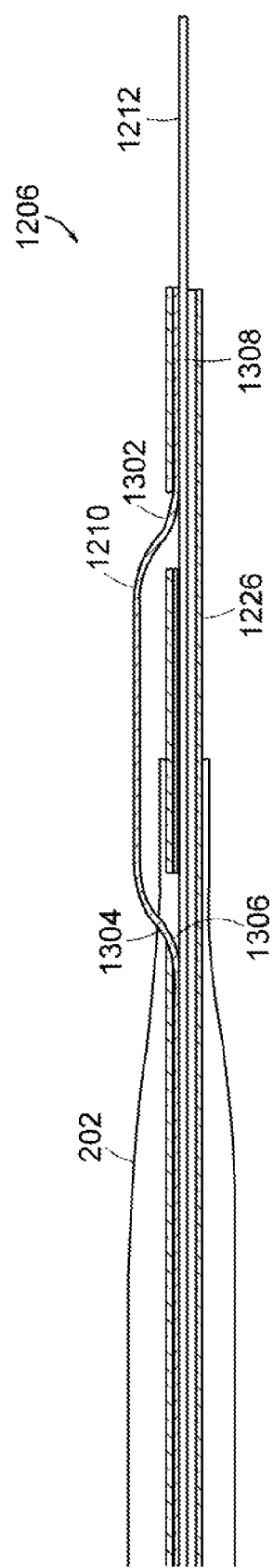
FIG. 14A
FIG. 14B

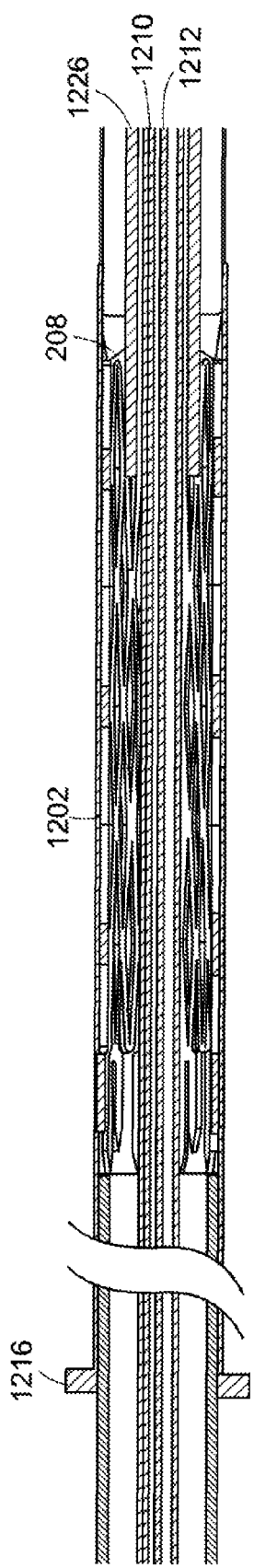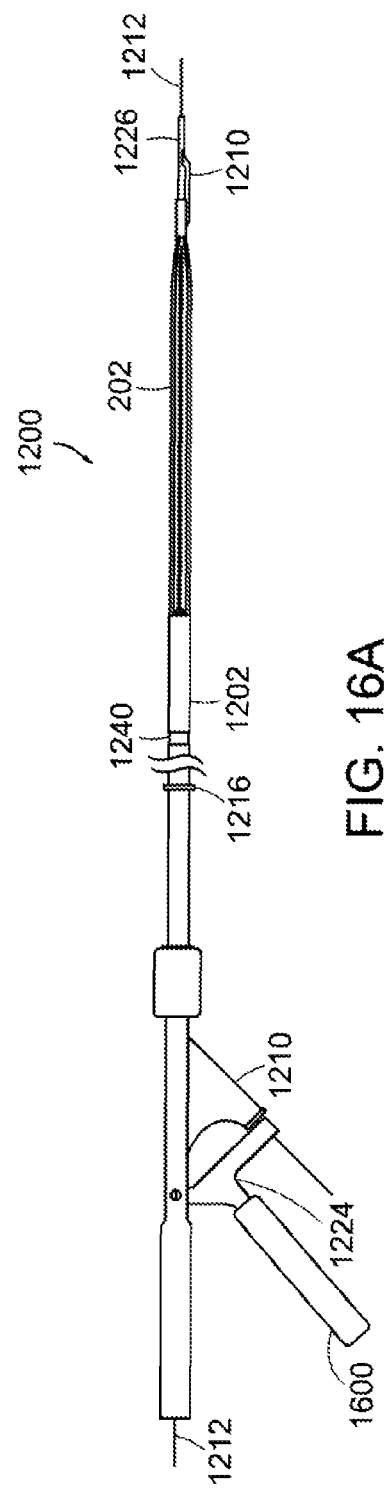

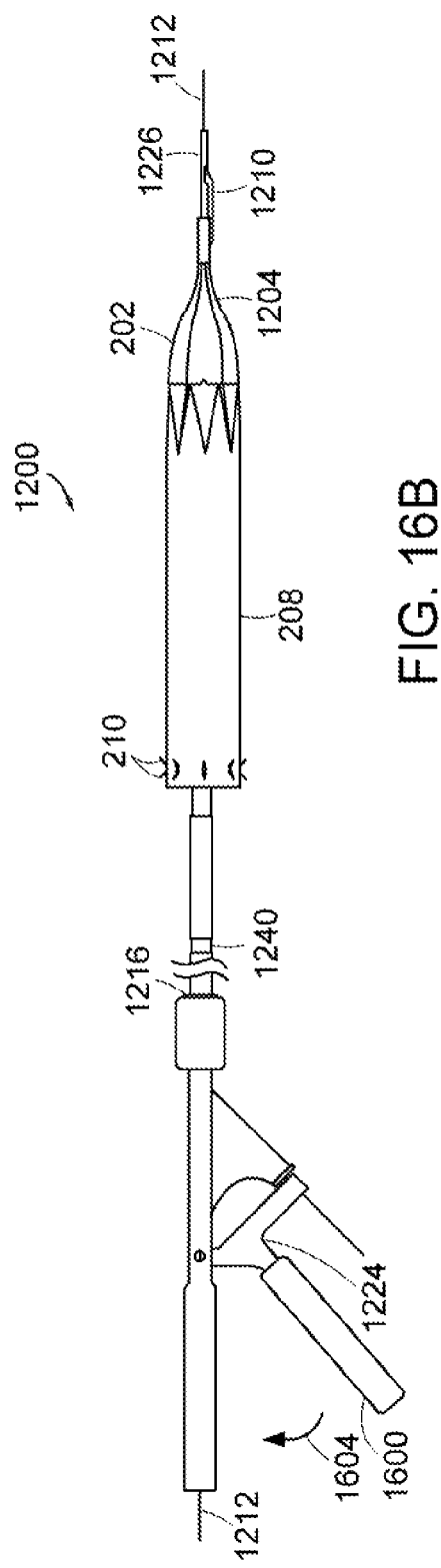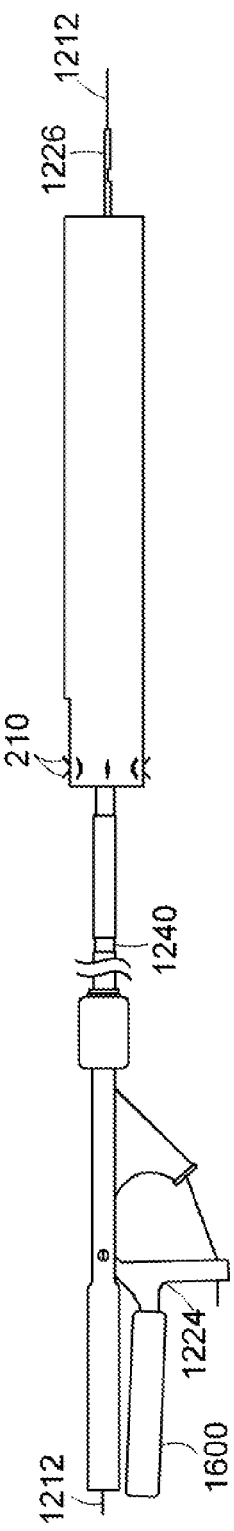
FIG. 16B
FIG. 16C

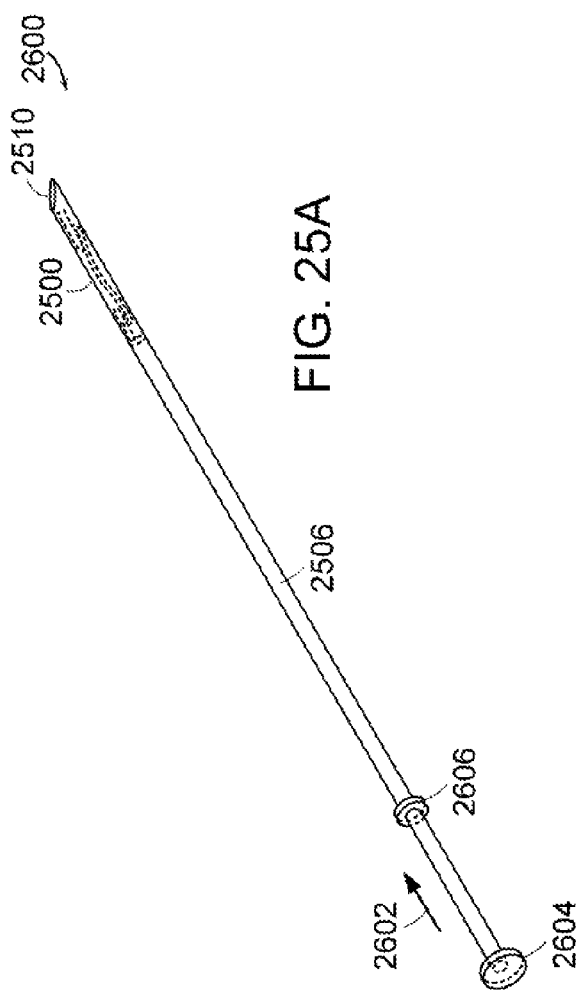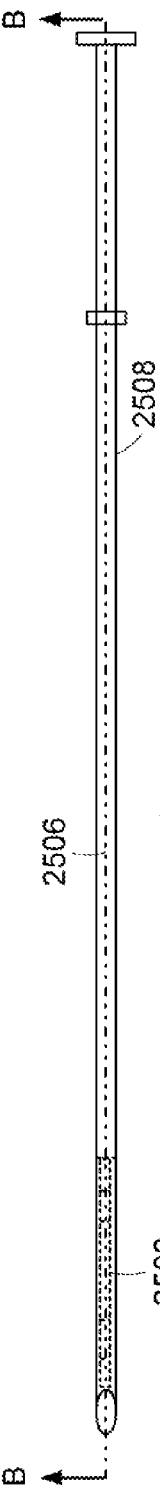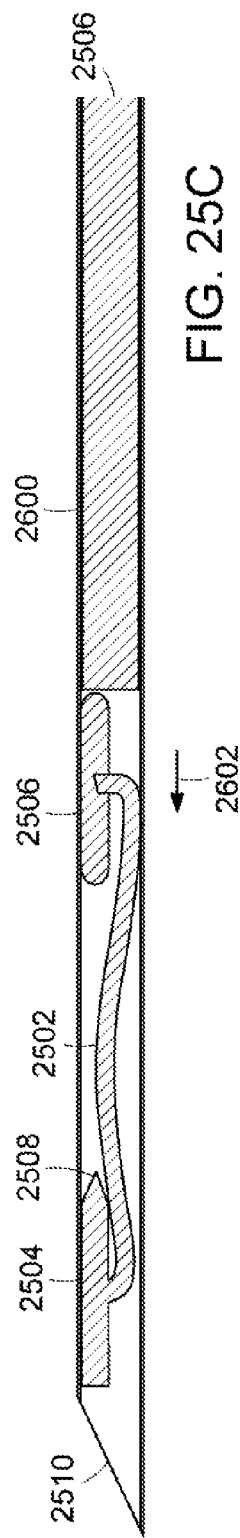

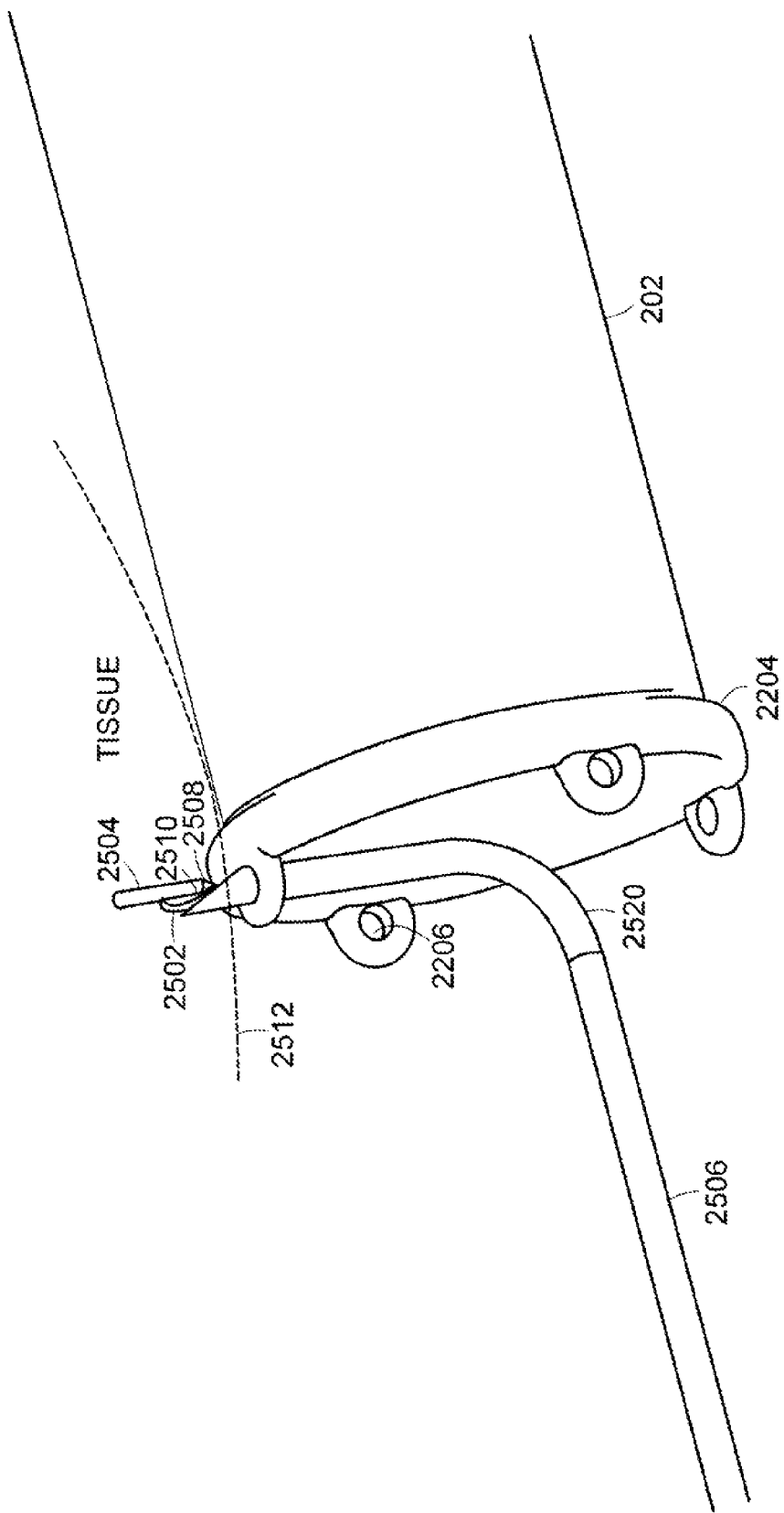

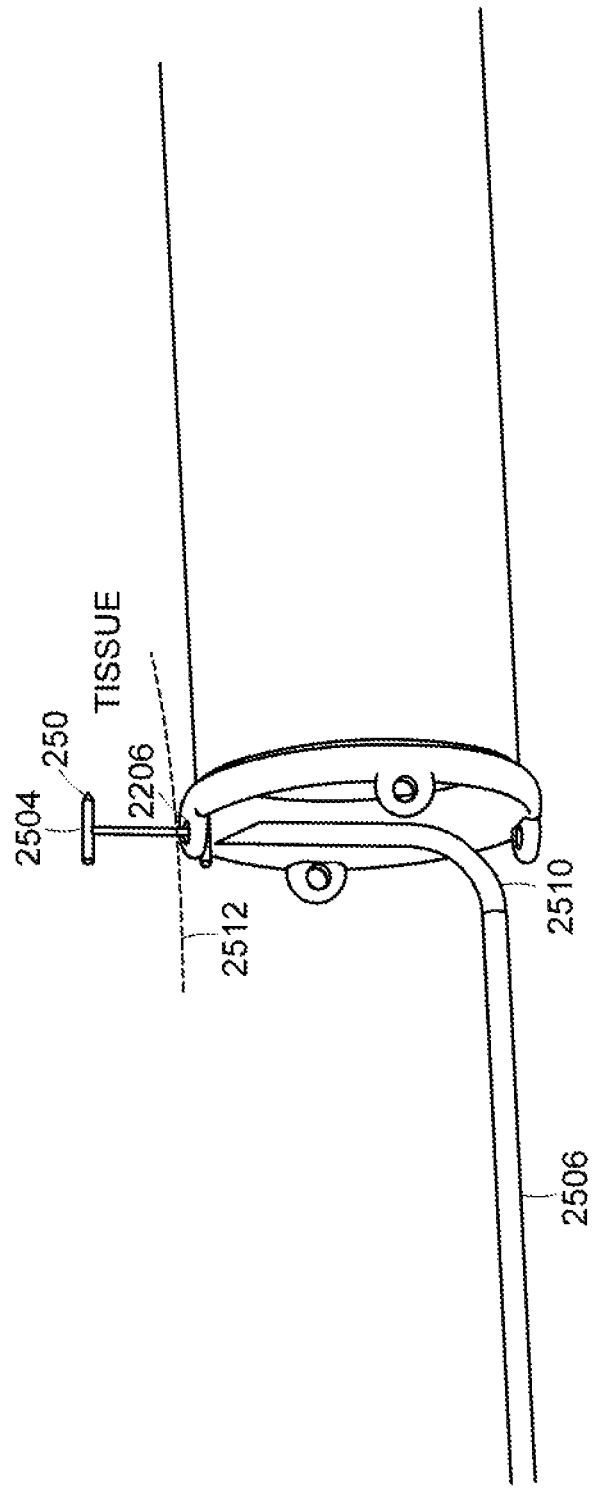

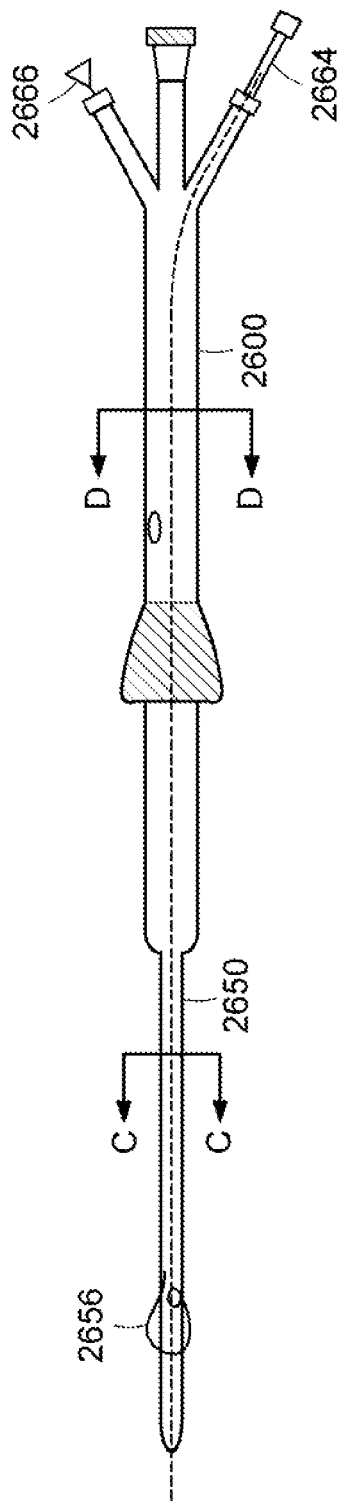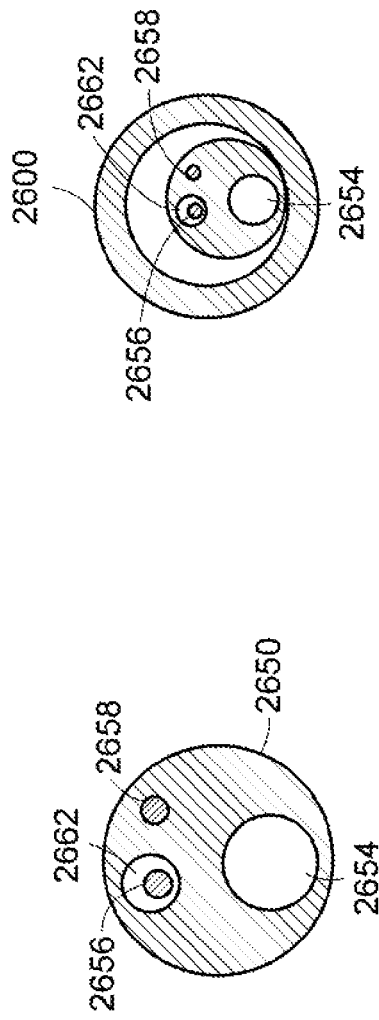
FIG. 26A
FIG. 26B
FIG. 26C

INTESTINAL SLEEVE

RELATED APPLICATIONS

This application is a continuation of U.S. application Ser. No. 14/305,518, filed Jun. 16, 2014, which is a continuation of U.S. application Ser. No. 13/170,785, filed Jun. 28, 2011, issued as U.S. Pat. No. 8,834,405, filed Sep. 16, 2014, which is a continuation of U.S. application Ser. No. 12/684,309, filed Jan. 8, 2010, issued as U.S. Pat. No. 7,981,163 on Jul. 19, 2011, which is a continuation of U.S. application Ser. No. 11/493,487, filed Jul. 26, 2006, issued as U.S. Pat. No. 7,682,330 on Mar. 23, 2010, which is a divisional of U.S. application Ser. No. 10/858,851, filed Jun. 1, 2004, issued as U.S. Pat. No. 7,476,256 on Jan. 13, 2009, which claims the benefit of U.S. Provisional Application No. 60/528,084, filed Dec. 9, 2003 and U.S. Provisional Application No. 60/544,527, filed Feb. 13, 2004. The entire teachings of the above applications are incorporated herein by reference.

BACKGROUND OF THE INVENTION

According to the Center for Disease Control (CDC), over sixty percent of the United States population is overweight, and almost twenty percent are obese. This translates into 38.8 million adults in the United States with a Body Mass Index (BMI) of 30 or above. The BMI is defined as a person's weight (in kilograms) divided by height (in meters), squared. To be considered clinically, morbidly obese, one must meet one of three criteria: BMI over 35, 100 lbs. overweight or 100% above ideal body weight. There is also a category for the super-obese for those weighing over 350 lbs.

Obesity is an overwhelming health problem. Because of the enormous strain associated with carrying this excess weight, organs are affected, as are the nervous and circulatory systems. In 2000, the National Institute of Diabetes, Digestive and Kidney Diseases (NIDDK) estimated that there were 280,000 deaths directly related to obesity. The NIDDK further estimated that the direct cost of healthcare in the US associated with obesity is $51 billion. In addition, Americans spend $33 billion per year on weight loss products. In spite of this economic cost and consumer commitment, the prevalence of obesity continues to rise at alarming rates. From 1991 to 2000, obesity in the US grew by 61%. Not exclusively a US problem, worldwide obesity ranges are also increasing dramatically.

One of the principle costs to the healthcare system stems from the co-morbidities associated with obesity. Type-2 diabetes has climbed to 7.3% of the population. Of those persons with Type-2 diabetes, almost half are clinically obese, and two thirds are approaching obese. Other co-morbidities include hypertension, coronary artery disease, hypercholesteremia, sleep apnea and pulmonary hypertension.

Although the physiology and psychology of obesity are complex, the medical consensus is that the cause is quite simple—an over intake of calories combined with a reduction in energy expenditures seen in modern society. While the treatment seems quite intuitive, the institution of a cure is a complex issue that has so far vexed the best efforts of medical science. Dieting is not an adequate long-term solution for most people. Once an individual has slipped past the BMI of 30, significant changes in lifestyle are the only solution.

There have been many attempts in the past to surgically modify patients' anatomies to attack the consumption problem by reducing the desire to eat. Stomach saplings, or gastroplasties, to reduce the volumetric size of the stomach, therein achieving faster satiety, were performed in the 1980's and early 1990's. Although able to achieve early weight loss, sustained reduction was not obtained. The reasons are not all known, but are believed related to several factors. One of which is that the stomach stretches over time increasing volume while psychological drivers motivate patients to find creative approaches to literally eat around the smaller pouch.

There are currently two surgical procedures that successfully produce long-term weight loss; the Roux-en-Y gastric bypass and the biliopancreatic diversion with duodenal switch (BPD). Both procedures reduce the size of the stomach plus shorten the effective-length of intestine available for nutrient absorption. Reduction of the stomach size reduces stomach capacity and the ability of the patient to take in food. Bypassing the duodenum makes it more difficult to digest fats, high sugar and carbohydrate rich foods. One objective of the surgery is to provide feedback to the patient by producing a dumping syndrome if they do eat these food products. Dumping occurs when carbohydrates directly enter the jejunum without being first conditioned in the duodenum. The result is that a large quantity of fluid is discharged into the food from the intestinal lining. The total effect makes the patient feel light-headed and results in severe diarrhea. For reasons that have not been determined the procedure also has an immediate therapeutic effect on diabetes.

Although the physiology seems simple, the exact mechanism of action in these procedures is not understood. Current theory is that negative feedback is provided from both regurgitation into the esophagus and dumping when large volumes of the wrong foods are eaten. Eventually, patients learn that to avoid both these issues they must be compliant with the dietary restrictions imposed by their modified anatomy. In the BPD procedure, large lengths of jejunum are bypassed resulting in malabsorption and therefore, reduced caloric uptake. In fact, the stomach is not reduced in size as much in the BPD procedure so that the patient is able to consume sufficient quantities of food to compensate for the reduced absorption. This procedure is reserved for the most morbidly obese as there are several serious side effects of prolonged malabsorption.

Unfortunately, these procedures carry a heavy toll. The morbidity rate for surgical procedures is alarmingly high with 11% requiring surgical intervention for correction. Early small bowel obstruction occurs at a rate of between 2-6% in these surgeries and mortality rates are reported to be approximately 0.5-1.5%. While surgery seems to be an effective answer, the current invasive procedures are not acceptable with these complication rates. Laparoscopic techniques applied to these surgeries provide fewer surgical complications but continue to expose these very ill patients to high operative risk in addition to requiring an enormous level of skill by the surgeon. Devices to reduce absorption in the small intestines have been proposed (See U.S. Pat. No. 5,820,584 (Crabb), U.S. Pat. No. 5,306,300 (Berry) and U.S. Pat. No. 4,315,509 (Smit)). However, these devices have not been successfully implemented.

SUMMARY OF THE INVENTION

The present invention provides a method and apparatus for the application of a barrier sleeve in the digestive tract to limit absorption of food products in specific parts of the digestive tract and to provide negative feedback to patients with morbid obesity enabling them to modify their heating habits. The sleeve may also be used for other treatments such as Type-2 diabetes.

A gastrointestinal implant device includes an unsupported flexible sleeve and an anchor coupled to a proximal portion of the sleeve. The flexible sleeve is open at both ends, and adapted to extend into the duodenum to limit absorption of nutrients in the duodenum. The anchor is adapted to be retained within the duodenum, particularly in the duodenal bulb just distal to the pylorus.

The anchor may be collapsible for ease of insertion and/or removal in a minimally. For example, the anchor may be inserted and/or removed endoluminally using a catheter-based procedure. The collapsible anchor is also well adapted for insertion into the duodenum, being capable of collapsing and/or flexing in response to natural movements of the local anatomy. The anchor can be covered by a proximal portion of the sleeve, and in some embodiments is sandwiched between a first inner layer and a second outer layer of the sleeve. The sleeve is of a length that chyme exiting the stomach funneled through the proximal end of the sleeve exits the sleeve through the distal end. The length of the sleeve can be varied. In some embodiments, the sleeve extends below the ligament of Treitz. In preferred embodiments, the sleeve material has a coefficient of friction of less than about 0.2. The sleeve may be formed of a biocompatible, low-friction material such as a fluoropolymer. In some embodiments, the sleeve is formed from PolyTetraFluoro-Ethylene (PTFE), expanded PTFE (ePTFE), or polyolefin (e.g., as a low density polyethylene film). Additionally, the sleeve may be coated or impregnated with a second material, such as polyurethane or silicone to reduce permeability. Still further, the distal end of the sleeve may be directionally textured.

The anchor can be attached to the surrounding anatomy using mechanical fasteners, such as sutures, surgical staples. In some embodiments, the mechanical fasteners can be dissolvable, dissolving after a predetermined time and allowing the device to pass naturally. In other embodiments, the anchor is attached to the surrounding anatomy using an interference fit provided by the relative size of the anchor in relation to the surrounding anatomy. Alternatively or in addition, the anchor can be attached to the surrounding anatomy using chemical fasteners, such as surgical adhesives.

Mechanical fasteners include barbs that extend from the exterior surface of the anchor for anchoring the proximal portion of the sleeve to the muscular tissue of the surrounding anatomy. The barbs may be bi-directional for anchoring the proximal portion of the flexible sleeve to the duodenum. Alternative anchors coupled to a proximal portion of the sleeve include a ring, a stent formed by a network of struts, or a wire formed as a wave.

An anti-buckling device may also be coupled to the sleeve and extend from below the anchor to the distal end of the flexible sleeve to reduce twisting and buckling of the sleeve. The sleeve allows enzymes secreted in the duodenum to pass through the duodenum outside the sleeve.

The gastrointestinal implant device can be inserted endoluminally in combination with a delivery catheter and can be similarly removed in combination with a removal device. More generally, the device can be implanted through a natural body lumen, such as per-orally and/or per-anally. Alternatively or in addition, the device can be implanted percutaneously. In one embodiment, the delivery apparatus includes a catheter for passage through the intestines and a spherically-shaped element coupled to the distal end of the catheter. In some embodiments, the spherically-shaped element can be remotely releasable.

In another aspect, a gastrointestinal implant device includes an unsupported flexible sleeve and a wave anchor coupled to a proximal portion of the sleeve. The wave anchor includes a compliant, radial spring shaped into an annular wave pattern about a central axis, providing an outward radial force, while allowing substantial flexure about its perimeter. Such flexure is advantageous as it allows for minimally-invasive delivery and ensures that the device will substantially conform to the surrounding anatomical structure when implanted. The annular wave element can be formed from one or more elongated resilient members and defines a lumen along its central axis formed between two open ends. When implanted, the central axis of the anchor is substantially aligned with the central axis of the duodenum, allowing chyme to pass through the device. Additionally, the compliant wave anchor minimizes trauma to the tissue by providing sufficient flexibility and compliance, while minimizing the likelihood of tissue erosion and providing a solid anchoring point to the tissue.

The anchor can be removably attached within the body using any of the methods described herein for securing an anchor, including the use of barbs attached to, and/or formed on the anchor itself. When implanted, the anchor enables a sleeve, or barrier to be securely implanted within the duodenum, preferably providing a fluid seal at the proximal end. To enhance a fluid seal, the proximal end of the sleeve can be contoured along a leading edge of the wave anchor. In this manner, substantially no unsupported sleeve remains proximal to the wave anchor. Thus, chyme is allowed to flow substantially unimpeded into the sleeve without becoming entrapped at the anchor.

The gastrointestinal implant device can be used in a method for treating intestinal bowel disease. An unsupported flexible sleeve is anchored within the duodenum. The sleeve is open at both ends and may be impregnated with a drug that reduces inflammation.

The gastrointestinal implant device can be used as a method for treating obesity. An unsupported flexible sleeve is anchored within the duodenum. The sleeve is open at both ends and enhanced with anti-hunger hormones.

The gastrointestinal implant device can be used as a method for treating Type-2 diabetes. A proximal portion of an unsupported flexible sleeve, open at both ends, is coupled to a collapsible anchor. The anchor includes barbs for insertion into tissue as the anchor expands to anchor the proximal portion of the sleeve in the duodenum. The flexible sleeve is extended at least into the duodenum to limit the digestion and/or absorption of nutrients.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 11 illustrates the gastrointestinal device shown in FIG. 1 including an anti-buckling mechanism;

FIG. 14A is an expanded perspective view of the dead-bolt mechanism shown in FIG. 12;

FIG. 14B is a sectional view of the dead-bolt mechanism shown in FIG. 13A illustrating the sleeve retention wire threaded through the sleeve;

FIG. 15 is sectional view of a portion of the catheter system illustrating the collapsed anchor stored inside the outer sheath;

FIG. 16A is a plan view of the catheter system illustrating the collapsed anchor stored inside the outer sheath of the gastrointestinal implant device;

FIG. 16B is a plan view of the catheter system illustrating the gastrointestinal implant device after release of the anchor from the outer sheath;

FIG. 16C is a plan view of the catheter system illustrating the expanded gastrointestinal implant device after the sleeve retention wire has been released;

FIG. 25A is a perspective view of a delivery system for delivering the anchor after the gastrointestinal implant device has been placed in the duodenum;

FIG. 25B is a plan view of the delivery system shown in FIG. 25A;

FIG. 25C is a cross-sectional view of the distal end of the catheter as taken along line B-B of FIG. 25A;

FIG. 25D is a perspective view of the gastrointestinal implant device illustrating the anchor engaged with the tissue;

FIG. 25E is an isometric view illustrating the barb engaging the tissue after delivery;

FIG. 26A is a plan view of the delivery system including a snare wire for holding the distal end of the sleeve in position;

FIG. 26B is a cross-sectional view taken along line CC of FIG. 26A through the inner sheath;

FIG. 26C is a cross-sectional view taken along line DD of FIG. 26A through the outer sheath showing the inner sheath within the outer sheath;

DETAILED DESCRIPTION OF THE INVENTION

Figure 1:
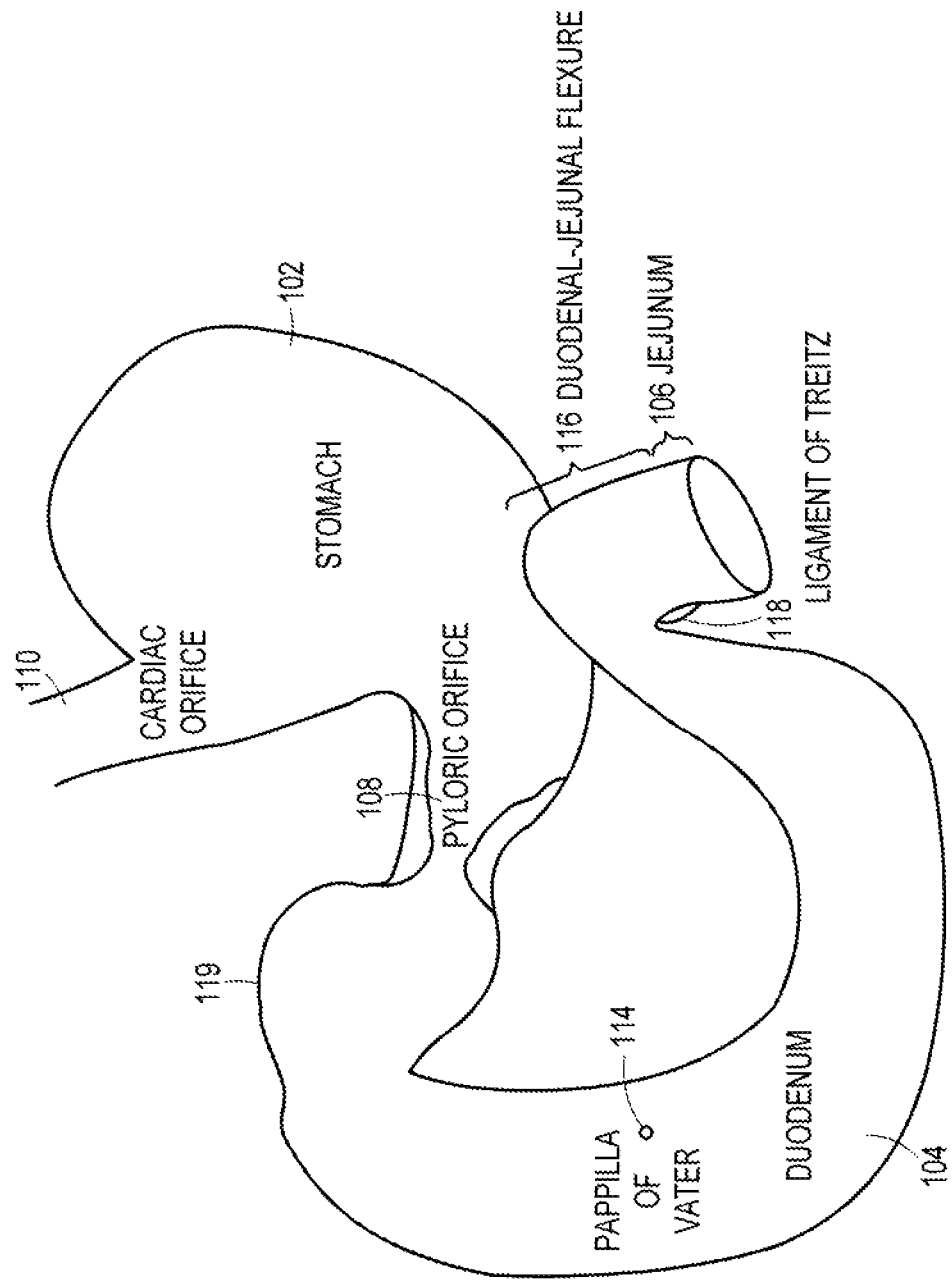
FIG. 1 is a sectional view of a portion of the digestive tract in a body.

A description of preferred embodiments of the invention follows. FIG. 1 is a sectional view of a portion of the digestive tract in a body. Food to be digested enters the stomach 102 through the cardiac orifice 110 from the esophagus. Chyme, a semi-fluid, homogeneous creamy or gruel-like material produced by gastric digestion in the stomach exits the stomach through the pyloric orifice (pylorus) 108 and enters the small intestine 112. The pylorus 108 is a distal aperture of the stomach 102 surrounded by a strong band of circular muscle. The small intestine, about nine feet in length, is a convoluted tube, extending from the pylorus 108 to the ileo-caecal valve where it terminates in the large intestine. The small intestine has three sections, the duodenum 104, jejunum 106 and the ileum (not shown). The first eight to ten inch section of the small intestine 112, the duodenum 104, is the shortest, widest and most fixed part of the small intestine 112.

The duodenum 104 has four sections: superior, descending, transverse and ascending which typically form a U-shape. The superior section is about two inches long and ends at the neck of the gall bladder. The superior section also defines a feature referred to as the duodenal bulb 119 that begins just distal to the pylorus 108 and extends for about 1 to 1.5 inches in an adult human. The duodenal bulb 119 defines a lumen therein that is slightly larger than the distal duodenum 104. Advantageously, the duodenal bulb 119 exhibits less motion than the pylorus 108 and even distal portions of the duodenum 104. Notably, the motion is substantially limited to contractions without having a significant linear component (i.e., no movement along the central axis of the intestine). However, the tissue thins as one moves away from the pylorus 108.

The descending section of the duodenum 104 is about three to four inches long and includes a nipple shaped structure (papilla of Vater) 114 through which pancreatic juice from the pancreas and bile produced by the liver and stored by the gall bladder enter the duodenum from the pancreatic and bile ducts. The pancreatic juice contains enzymes essential to protein digestion and bile dissolves the products of fat digestion. The ascending section is about two inches long and forms the duodenal-jejunal flexure 116 where it joins the jejunum 106, the next section of the small intestine. The duodenal-jejunal flexure 116 is fixed to the ligament of Treitz 118 (musculus supensionus duodeni). The juices secreted in the duodenum break the partially digested food down into particles small enough to be absorbed by the body. The digestive system is described in Gray's Anatomy ("Anatomy of the Human Body," by Henry Gray) and "Human Physiology," Vander, $3^{rd}$ ed, McGraw Hill, 1980, the contents of which are incorporated herein by reference in their entirety.

Figure 2:
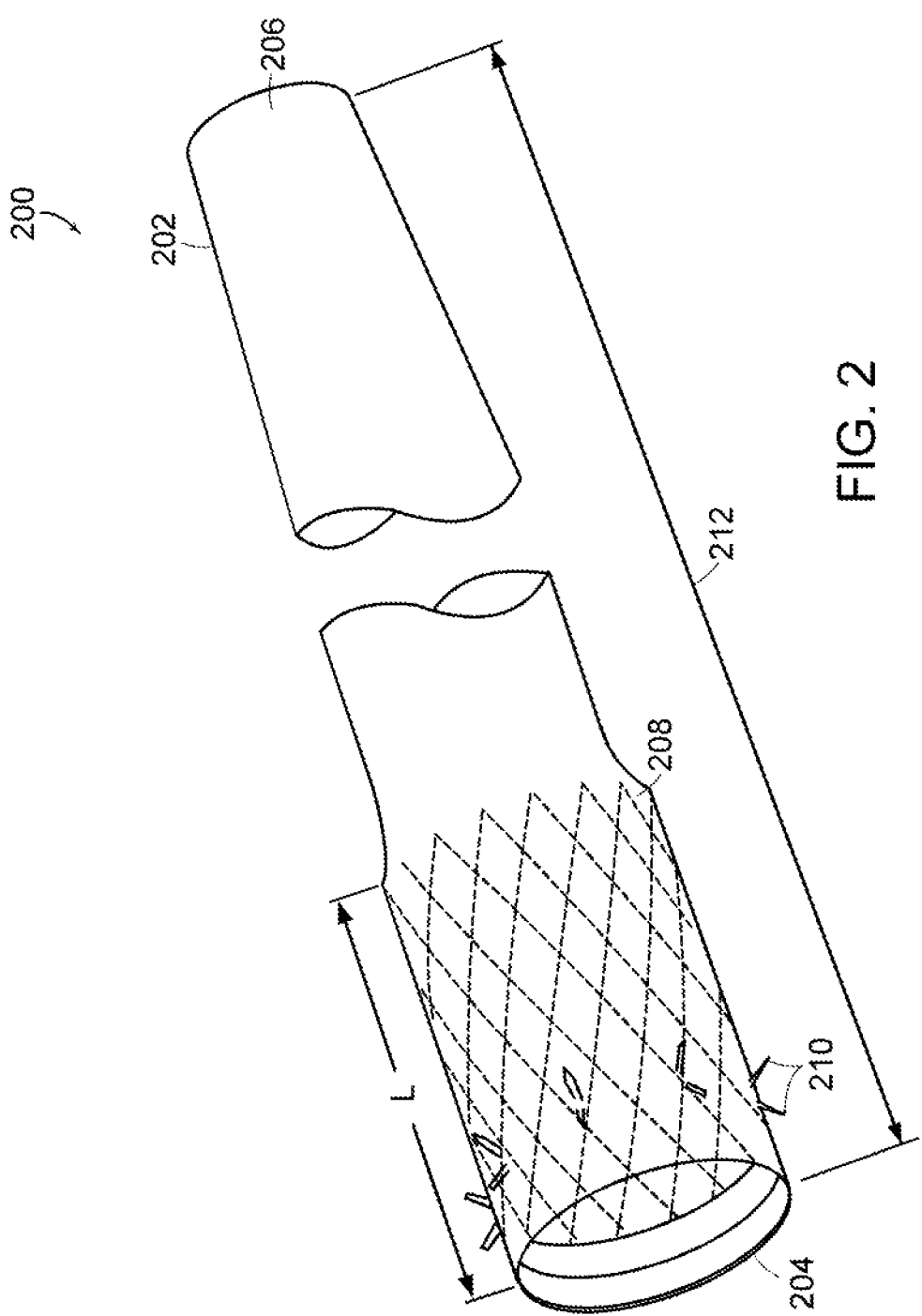
FIG. 2 is a perspective view of a gastrointestinal implant device according to the principles of the present invention.

FIG. 2 is a perspective view of a gastrointestinal implant device 200 according to the principles of the present invention. The gastrointestinal implant device 200 includes an elongated, open-ended, unsupported flexible sleeve or tube 202 having a first proximal opening 204 and a second distal opening 206. Within the sleeve 202 is a passageway that extends from the first proximal opening 204 to the second distal opening 206 for transporting the chyme exiting the stomach 102 (FIG. 1). The surface of the passageway (the interior surface of the implant device 200) is smooth to enable the chyme to easily pass through. The exterior surface of the implant device 200 is smooth to prevent tissue in-growth and to be non-irritating to the bowel.

Within the implant device 200 at the proximal end including the first proximal opening 204 is a collapsible self-expanding anchor 208. The anchor 208 includes a plurality of opposed barbs 210 for anchoring the implant device 200 to the muscular tissue of the duodenum 104. The diameter of the anchor 208 is dependent on the diameter of the duodenum 104 (FIG. 1) about 1.0" to 2.5" based on human anatomy variations. In one embodiment, the length 'l' of the anchor 208 is selected to reside within the bulbous duodenum 119.

Anchoring in the bulbous duodenum 119 offers several advantages over other areas in of gastrointestinal tract. First, the duodenal bulb 119 is proportionally sized to capture an anchor—that is it provides a cavity having a relatively large diameter bounded by anatomies having smaller diameters in both the proximal and distal directions. Thus, the duodenal bulb 119 is naturally configured to retain a suitably-shaped anchor.

Additionally, the duodenal bulb 119 is relatively less active than the either the pylorus or distal portions of the duodenum. The duodenal bulb 119 at least in part acts as a holding area for chyme received from the stomach. Thus, the duodenal bulb 119 provides a more stable anchoring platform as there is less movement there. Movement of the surrounding tissue can act to dislodge an anchor over time. Still further, as the tissue of at least the proximal portion of the duodenal bulb 119 is thicker than the tissue of the distal duodenum. Thus, the duodenal bulb 119 provides a better anchoring platform as it is adapted to regain longer fasteners (e.g., longer barbs).

The sleeve material is thin and conformable so that it collapses in the intestine to a small volume to minimize bowel irritability. It has a low coefficient of friction (less than about 0.20) so that chyme slides easily through it and the bowel slides easily around it. It is of low permeability to fluids so that the chyme does not touch the bowel wall and the digestive enzymes do not significantly breakdown the chyme. It is biologically inert and non-irritating to the tissues. One class of materials includes fluoropolymers. In some embodiments, the sleeve is formed from expanded PTFE with a wall thickness of about 0.006 inches and an internodal distance of 20 microns. This material is hydrophobic but is slightly porous. However, these very small pores may plug over time. The porosity may be reduced by coating the material on the inside, outside or in the pores with dilute solutions of silicone or polyurethane. Another material is polyethylene with a wall thickness of less than 0.001 inches. Other materials include Cast PolyTetraFluoroEthylene (PTFE, e.g., TEFLON), Cast PTFE with Fluorinated Ethylene Propylene (FEP) or PerFluoroAlkoxy (PFA) coating to minimize pin holes, Extruded FEP and Extruded PFA. These materials are solid and substantially non-porous in contrast to ePTFE which is porous, but these materials are also considered to be fluoropolymers. The wall thickness is preferably less than about 0.001 inches. Rubber-like materials typically have friction coefficients of about 1-4, significantly stickier than these materials. However, in alternate embodiments other materials having similar characteristics can be used.

In some embodiments, the sleeve is formed using a combination of two or more materials. For example, the sleeve can be formed using a combination of ePTFE and FEP. Such a combination can be formed by layering the two materials together and generally provides a low coefficient of friction while being substantially non-permeable.

The sleeve 202 includes two layers of material at least at the proximal end. A first outer layer covers the exterior of the anchor 208. The second inner layer covers the interior surface of the anchor 208. The barbs 210 protrude from the exterior surface of the anchor 208 through the first outer layer of the sleeve 202. The holes in the first outer layer through which the barbs 210 protrude can be filled with an impervious material such as silicone or urethane to limit mixing of digestive juices with the chyme flowing through the passageway. The diameter of the sleeve 202 is selected such that the first outer layer of the sleeve 202 fits over the anchor 208.

The sleeve length 212 is variable and can range from about one foot to about five feet. The typical length of the sleeve 202 is about 2 to 4 feet measured from the anchor (barbs 210) in the bulbous duodenum 119 to below the ligament of Treitz 118 (FIG. 1). The length 212 of the sleeve 202 is selected to bypass the duodenum 104 (FIG. 1) and a portion of the jejunum 106. The length can optionally be increased to further decrease absorption by bypassing a longer section of the jejunum 106 (FIG. 1). Thus, the length 212 of the sleeve 202 is variable and may be dependent on the patient's Body Mass Index (BMI). The procedure is a less invasive alternative to surgery for the treatment of obesity and morbid obesity and also provides a new treatment approach for Type-2 diabetes.

The covered anchor 208 can be collapsed into a sheath having a diameter less than about 12 mm or less to enable endoluminal and/or catheter-based delivery. Covering the exterior surface of the anchor 208 with the first outer layer of the sleeve 202 permits catheter-based removal of the implant device 200 by preventing tissue in-growth on the exterior surface of the anchor 208.

Additionally, markings can be added to the exterior surface of the sleeve 202 to detect the position and orientation of the sleeve on a fluoroscopic image and whether the sleeve is twisted. For example, a radiopaque stripe can be painted down the length of the device 200 using tantulum impregnated ink, or tantulum bands can be bonded to a surface of the device, such as the interior surface. If the sleeve 202 is twisted, the sleeve 202 can be untwisted by inserting a balloon into the proximal end of the device thereby sealing it, and then injecting water into the sleeve 202 at low pressure. More generally, a radiopaque marking can also be used to facilitate placement and/or removal of the device.

Figure 3A:
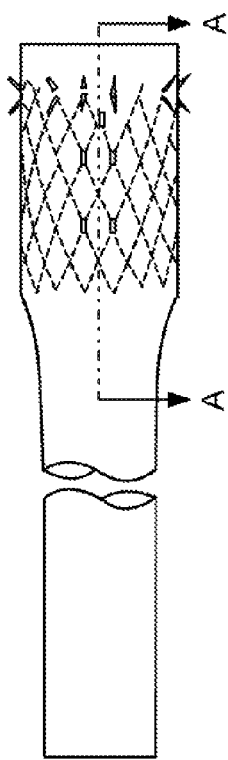
FIG. 3A is a plan view of the proximal portion of the gastrointestinal implant device shown in FIG. 2.
Figure 3B:
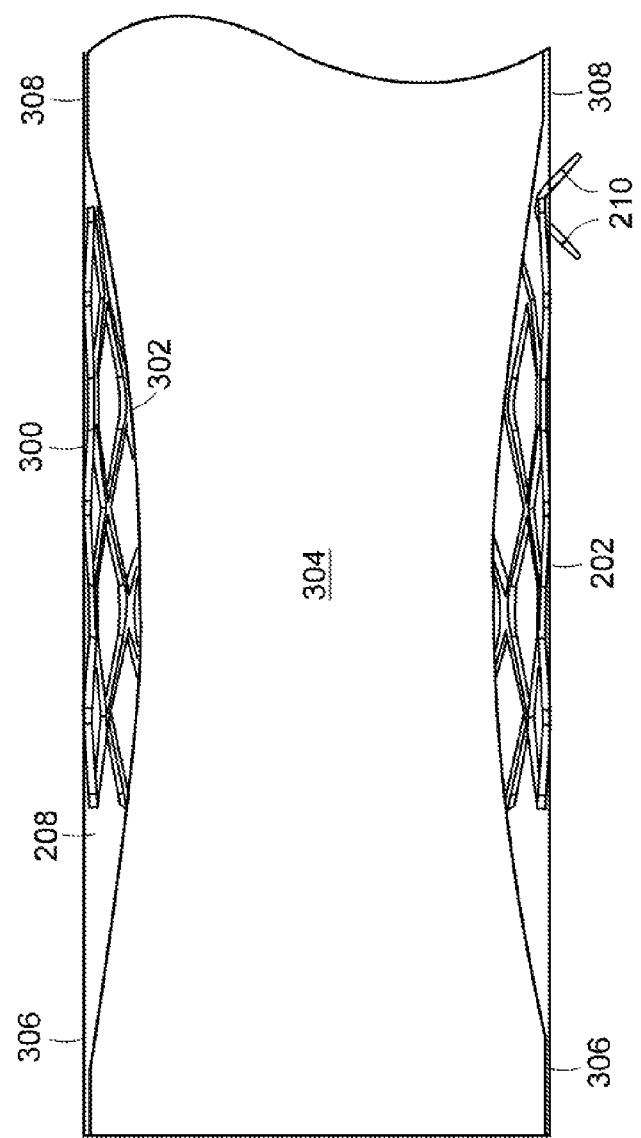
FIG. 3B is a cross-sectional view as taken along line A-A of FIG. 3A showing the anchor and first inner layer and second outer layer of the sleeve shown in FIG. 2.

FIG. 3A is a plan view of the proximal portion of the gastrointestinal implant device 200 shown in FIG. 2. FIG. 3B is a cross-sectional view as taken along line AA of FIG. 3A showing the anchor 208 and the first outer layer 300 and the second inner layer 302 of the sleeve 202 shown in FIG. 2. As described in conjunction with FIG. 2, the sleeve 202 includes a first outer layer 300 and a second inner layer 302. The first outer layer 300 is bonded to the second inner layer 300 at positions 306 below the distal end of the anchor 208 and at positions 308, above the proximal end of the anchor 208. A passageway 304 inside the second inner layer 302 of the sleeve 202 allows passage of chyme through the sleeve 202. The anchor 208 is sandwiched between the first outer layer 300 and the second inner layer 302 at the proximal end of the sleeve 202 and is free to move at the distal end within the first outer layer 300 and the second inner layer 302 of the sleeve 202. The covered exterior surface of the anchor 208 prevents tissue growth that could otherwise hinder removal of the implant device 200. The covered interior surface of the anchor 208 provides a smooth passageway for chyme to bypass the duodenum 104.

Figure 4:
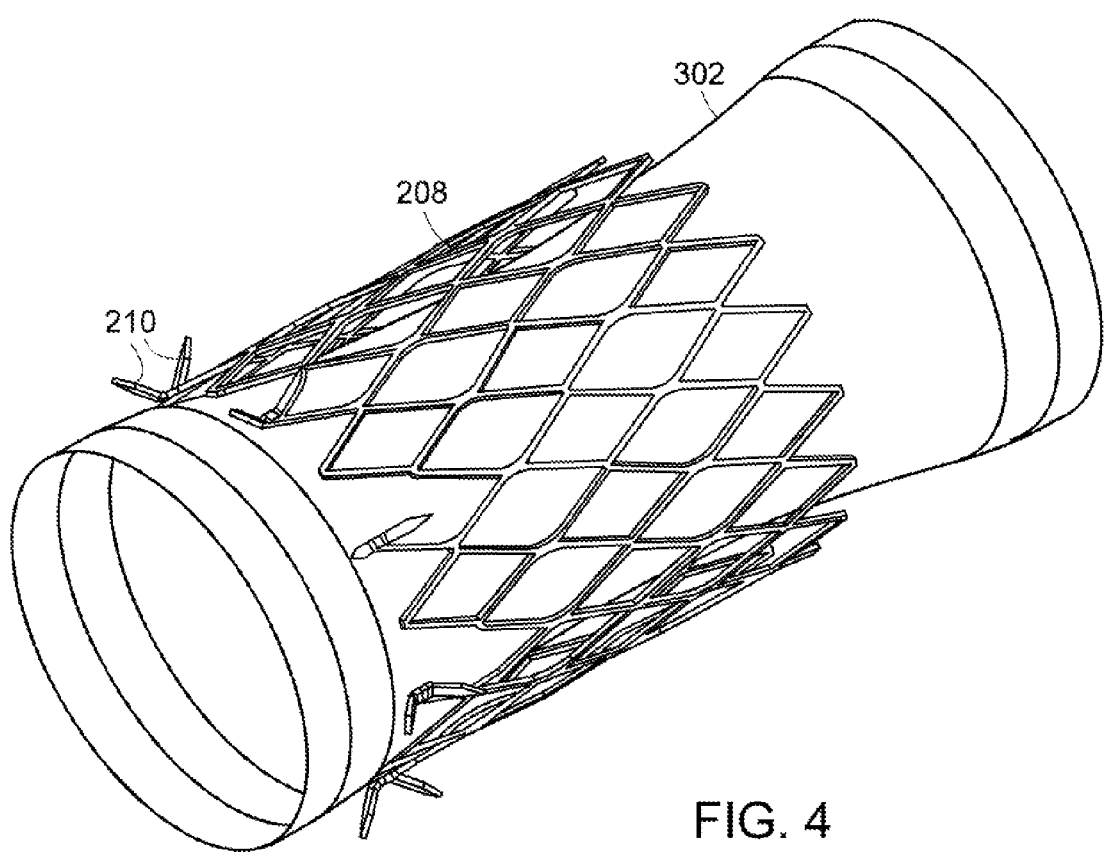
FIG. 4 is a perspective view of the gastrointestinal implant device with the second outer layer of the sleeve removed.

FIG. 4 is a perspective view of the gastrointestinal implant device 200 with the first outer layer 300 of the sleeve 202 removed. The interconnecting struts which form the mesh (a network of struts) with diamond spaced openings are sufficiently flexible to allow the anchor to be collapsed inside a delivery catheter and have sufficient elasticity to engage the interior walls of the covered region of the intestine once the catheter is withdrawn. The force needed to provide a fluid seal is provided when the anchor 208 is compressed from its full diameter (e.g., an anchor having a relaxed diameter of about 1.75 inches and an implanted diameter of about 1.5 inches).

Figure 5:
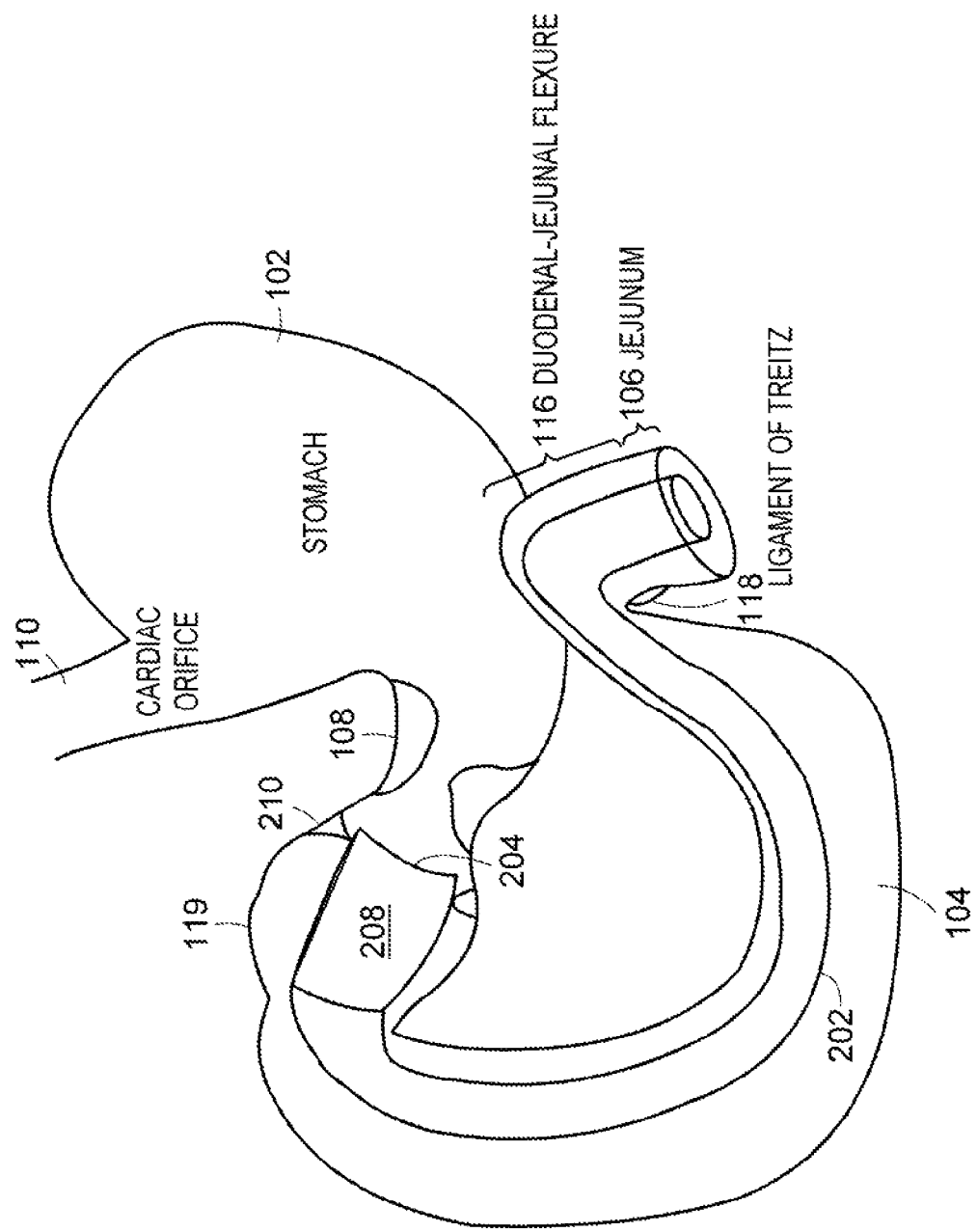
FIG. 5 is a sectional view of a body showing the gastrointestinal implant device implanted in the digestive system.

FIG. 5 is a sectional view of a body showing the gastrointestinal implant device 200 implanted in the digestive system. The first proximal end 204 of the implant device 200 is anchored to the duodenum 104. The barbs 210 grip onto the muscular tissue to anchor the implant device 200 in place so that the implant device 200 can not be dragged into the stomach 102 or down into the intestines with movement of the stomach 102 and the intestines.

The sleeve 202 can extend over the ligament of Treitz 118 beyond the proximal jejunum 106. Extending the sleeve 202 below the ligament of Treitz 118 reduces the likelihood that the sleeve 202 will move back through the duodenum 104 toward the stomach 102.

After the gastrointestinal implant device 200 has been placed in the body and anchored in the duodenum 104, chyme leaving the stomach passes through passageway 304 (FIG. 3B) inside the sleeve 202 and bypasses the duodenum 104 and proximal jejunum 106. By directing the chyme through the sleeve 202 the digestion and the absorption process in the duodenum 104 is interrupted. By interrupting mixing of the chyme with juices in the duodenum 104, partially digested food material is not broken down into particles small enough to be absorbed by the body. Further, there is no mixing of bile with the chyme until the chyme reaches the jejunum 106. The absorption of fats and carbohydrates is reduced by delaying the mixing of bile with the chyme.

The sleeve 202 provides weight loss mechanisms by providing negative feedback, reduced fat digestion and reduced desire for food. The reduced fat digestion occurs because the sleeve 202 delays the mixing of bile and pancreatic juices with chyme from the stomach until after the chyme leaves the sleeve 202. The reduced desire for food may occur because the sleeve 202 blocks hormonal release from the duodenum 104. Additionally, providing poorly digested food to distal portions of the intestine, such as to the ileum, can trigger hormones that reduce appetite.

The sleeve 202 is non-compliant and drapes away from the intestinal walls thereby permitting the pancreatic juice to flow unimpeded into the duodenum 104 through the papilla of Vater 114. The normal peristalsis of the bowel is used to propel the chyme, bile, and pancreatic juices through the intestines.

Figure 6:
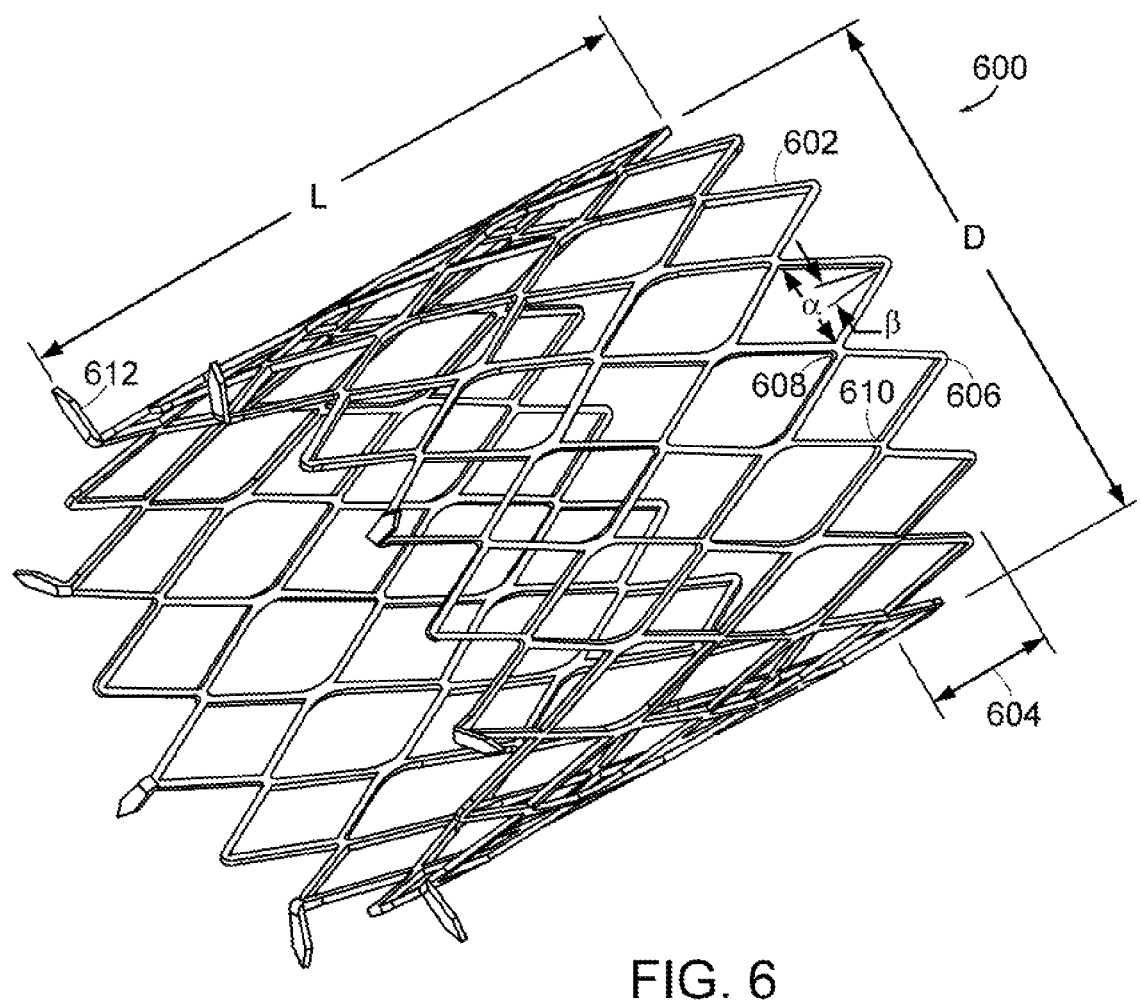
FIG. 6 is a perspective view of a collapsible self-expanding anchor in the gastrointestinal implant device.

FIG. 6 is a perspective view of a collapsible self-expanding anchor 600 in the gastrointestinal implant device 200 shown in FIG. 2 when expanded. The anchor 600 is non-woven, collapsible and self-expanding, allowing catheter-based insertion and removal of the implant device 200. The anchor 600 includes a plurality of flat struts 602 forming an open space pattern to ease collapsing while ensuring self-expansion. The open space pattern allows for collapsing into a catheter for endoluminal delivery and removal. The struts 602 may be manufactured from a resilient metal such as a heat-treated spring steel, or from an alloy such as NiTi alloy commonly referred to as Nitinol. Other alloys include nickel-cobalt-chromium-molybdenum alloys possessing a unique combination of ultrahigh tensile strength, such as MP35N, available from Asahi Intecc Co., Ltd. of Newport Beach, Calif.

In the embodiment shown, the anchor has a length L of about 1.5 inches and has a diameter D of about 1.5 inches. The struts 602 are flat, about 0.010 inches wide and about 0.004 to 0.010 inches thick. The anchor can be formed from a tube of material by laser cutting followed by expansion and heat setting, or other methods well known to those skilled in the art.

In an alternate embodiment, the struts 602 can be formed separately and the strut intersections can be welded or attached by other means well known to those skilled in the art. Visually the struts form sections 604 around the circumference of the anchor. Each section has a series of triangles with each triangle defined by one distal strut connection 606 and two proximal strut connections 608, 610. The ratio of the collapsed diameter to the expanded diameter of the anchor is roughly 1:4.

When expanded, the angle α between divergent strut sections is about 45-50 degrees and the diameter of the anchor is about 1.5 inches. When compressed, the angle β between divergent strut sections is about 5-6 degrees to reduce the diameter of the anchor to about 0.5 inches for catheter-based delivery and removal. The elasticity of the struts permits this compression. When the radial compression is released, the elasticity of the struts causes the anchor to expand to diameter D. The anchor assumes its desired diameter as the elastic restoring forces seek their minimum stress.

In some embodiments, the ends of the struts at the proximal end of the anchor 600 can be elongated and shaped to provide barbs 612 to anchor to the muscular tissue of the duodenum 104.

Figure 7:
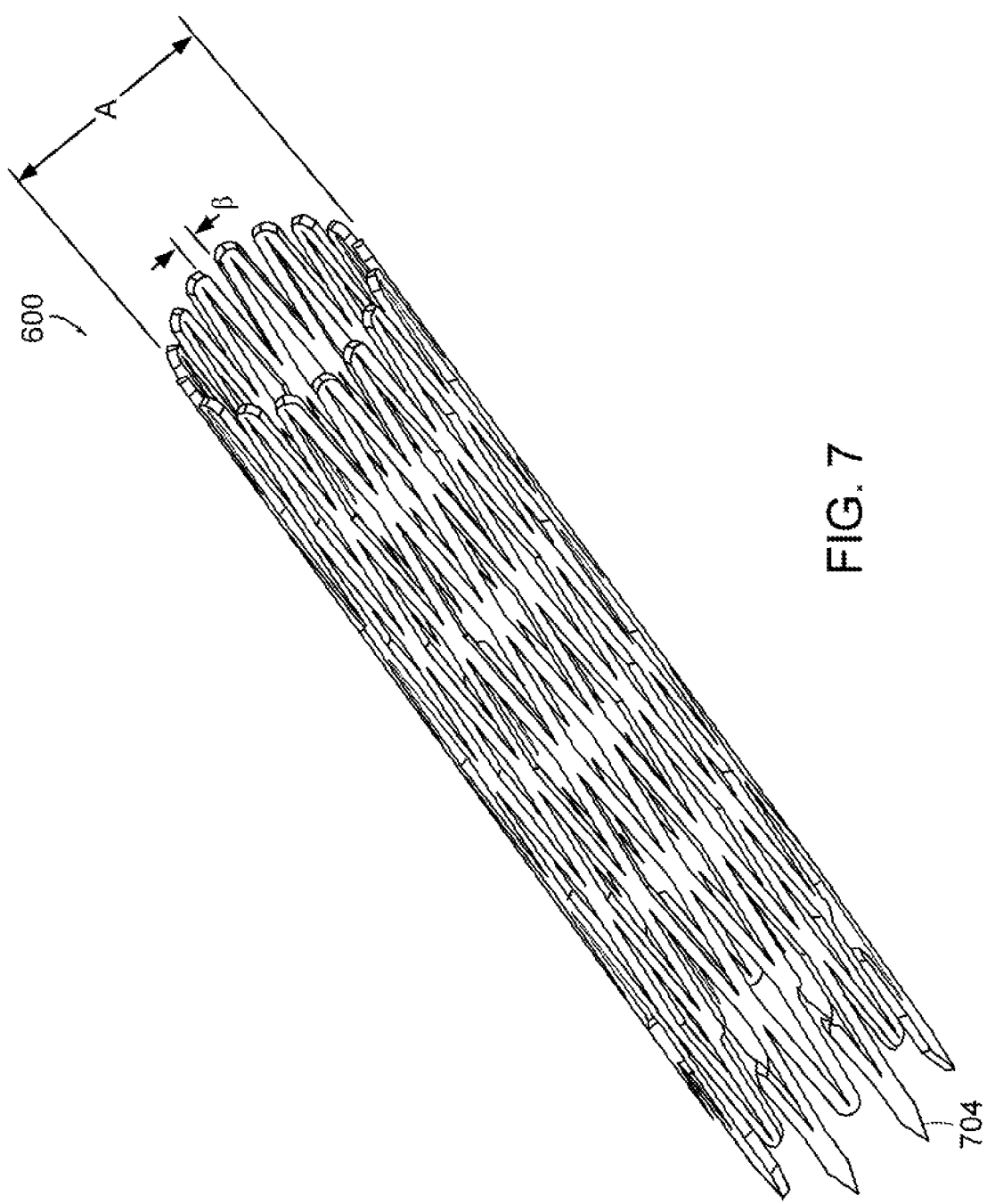
FIG. 7 is a perspective view of the anchor shown in FIG. 6 when compressed.

FIG. 7 is a perspective view of the anchor 600 shown in FIG. 6 when compressed. The anchor 600 is compressed until the angle β between divergent strut sections is about 5-6 degrees to reduce the diameter D of the anchor 600 to about 0.5 inches for catheter-based delivery and removal. The barbs 704 at the proximal end of the anchor are elongated. The barbs 704 can be shaped to anchor the anchor to the muscular tissue of the duodenum 104.

Figure 8:
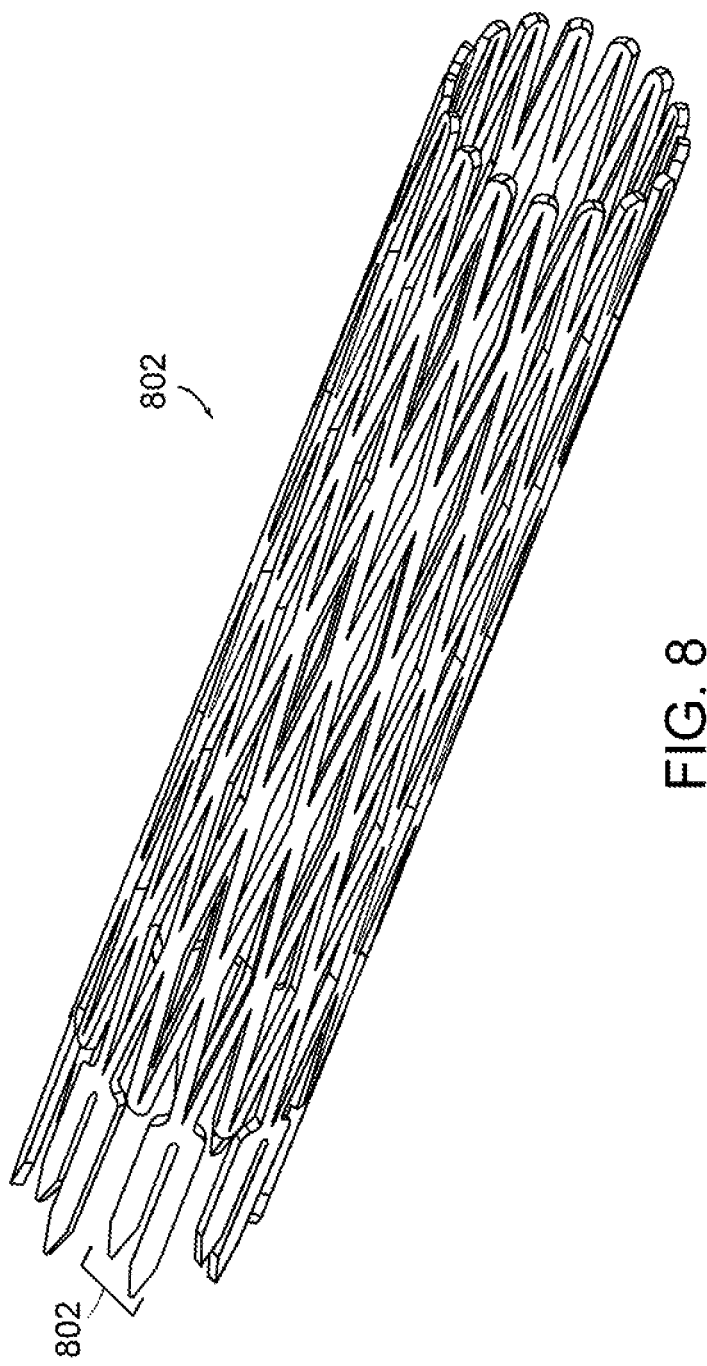
FIG. 8 is a perspective view of another embodiment of a anchor when compressed.

FIG. 8 is a perspective view of another embodiment of a anchor 800 when compressed. Pairs of barbs 802 at the proximal end of the anchor 800 are elongated and can be shaped to provide opposed barbs to anchor the anchor 800 in the muscular tissue of the duodenum 104.

Figure 9:
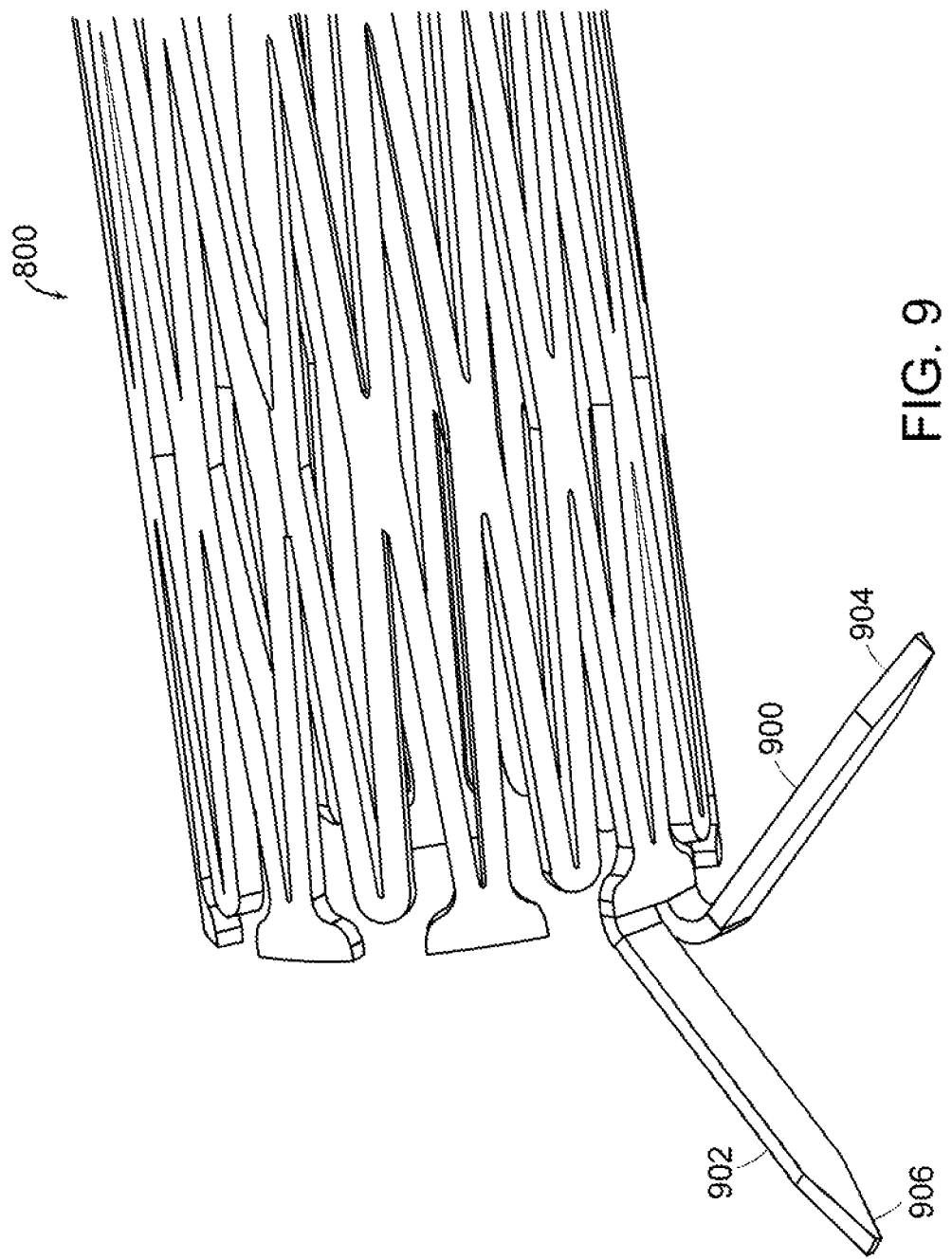
FIG. 9 is a perspective view of the anchor shown in FIG. 8 with the strut ends bent to provide opposed barbs.

FIG. 9 is a perspective view of the compressed anchor 800 shown in FIG. 8 with the strut ends 902, 900 bent to provide opposed barbs 904, 906. The barbs 904,906 engage the muscular tissue of the duodenum 104 to anchor the gastrointestinal implant device in the muscular tissue of the duodenum 104. As shown in FIG. 2, the strut ends 900, 902 protrude outward from the outer surface of the anchor 800 in opposite directions. They may be perpendicular to each other. The barbs 904, 906 at the ends of the respective opposed strut ends 900, 902 dig into the surrounding muscular tissue to secure the anchor. The barbs 904, 906 at the end of the protruding opposed strut ends 900, 902 prevent movement of the anchor 800 in either direction; that is, they prevent movement of the anchor 800 into the stomach 102 and prevent movement of the anchor 800 down through the duodenum 104.

Figure 10:
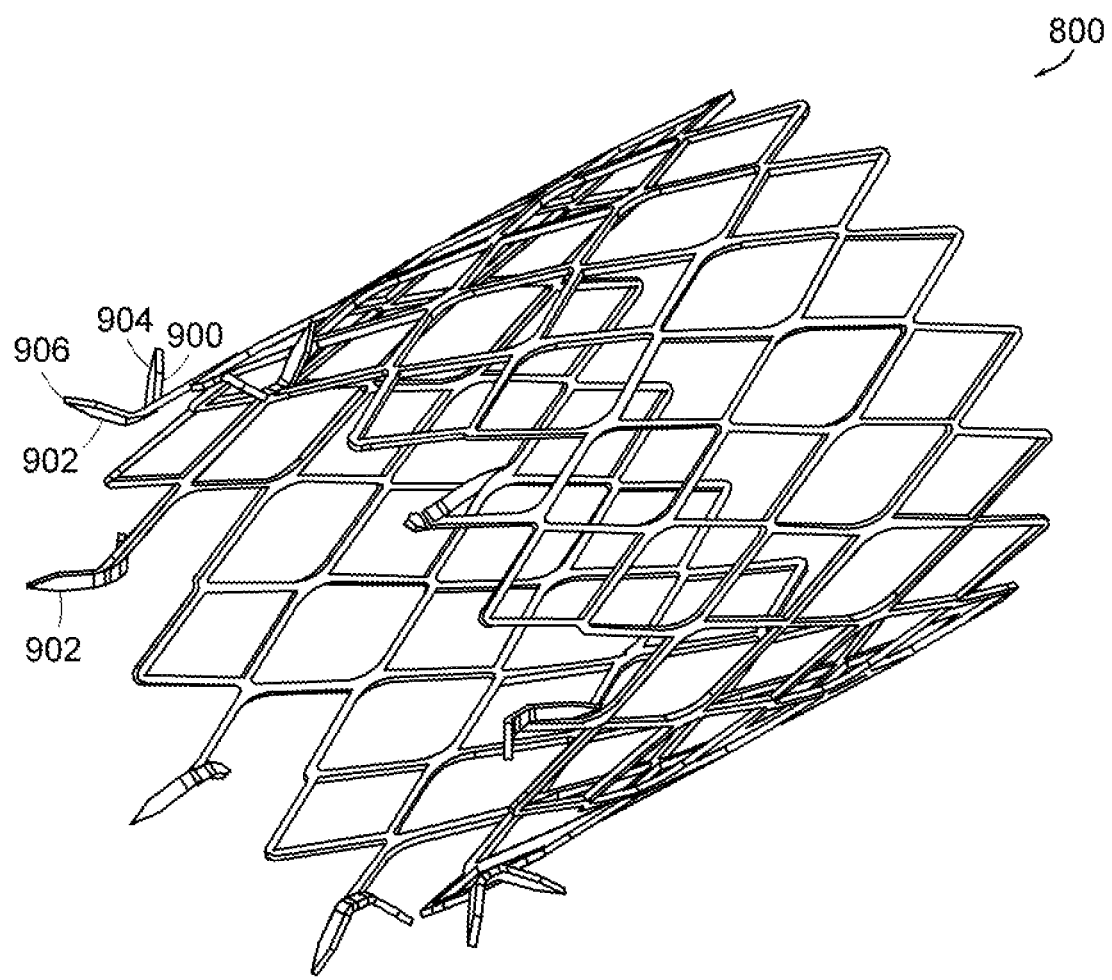
FIG. 10 is a perspective view of the anchor shown in FIG. 8 when expanded.

FIG. 10 is a perspective view of the anchor 800 shown in FIG. 8 when expanded. As discussed in conjunction with FIG. 9, the opposed strut ends 904, 906 engage the muscular tissue of the duodenum 104 while the anchor 800 is expanded. In the engaged position, the barbs 904, 906 spread radially outward from the longitudinal axis of the anchor 800 such that the tips of the barbs come into contact and engage the tissue.

FIG. 11 illustrates the gastrointestinal device 1100 shown in FIG. 1 including an anti-buckling mechanism 1102. A flexible, anti-rotation, anti-buckling mechanism 1102 is attached to the sleeve 202 and extends from below the distal end of the anchor along the length L of the sleeve to the distal end of the sleeve 202. In the embodiment shown, the anti-buckling mechanism 1102 is a guidewire device attached to the exterior surface of the outer layer of the flexible sleeve. Guidewire devices are well known to those skilled in the art. A first proximal end of the guidewire device 1104 is attached below the anchor and a second distal end of the guidewire device 1106 is attached to the distal end of the flexible sleeve. The diameter of the guidewire ranges from about 0.010 to about 0.016 inches.

Figure 12:
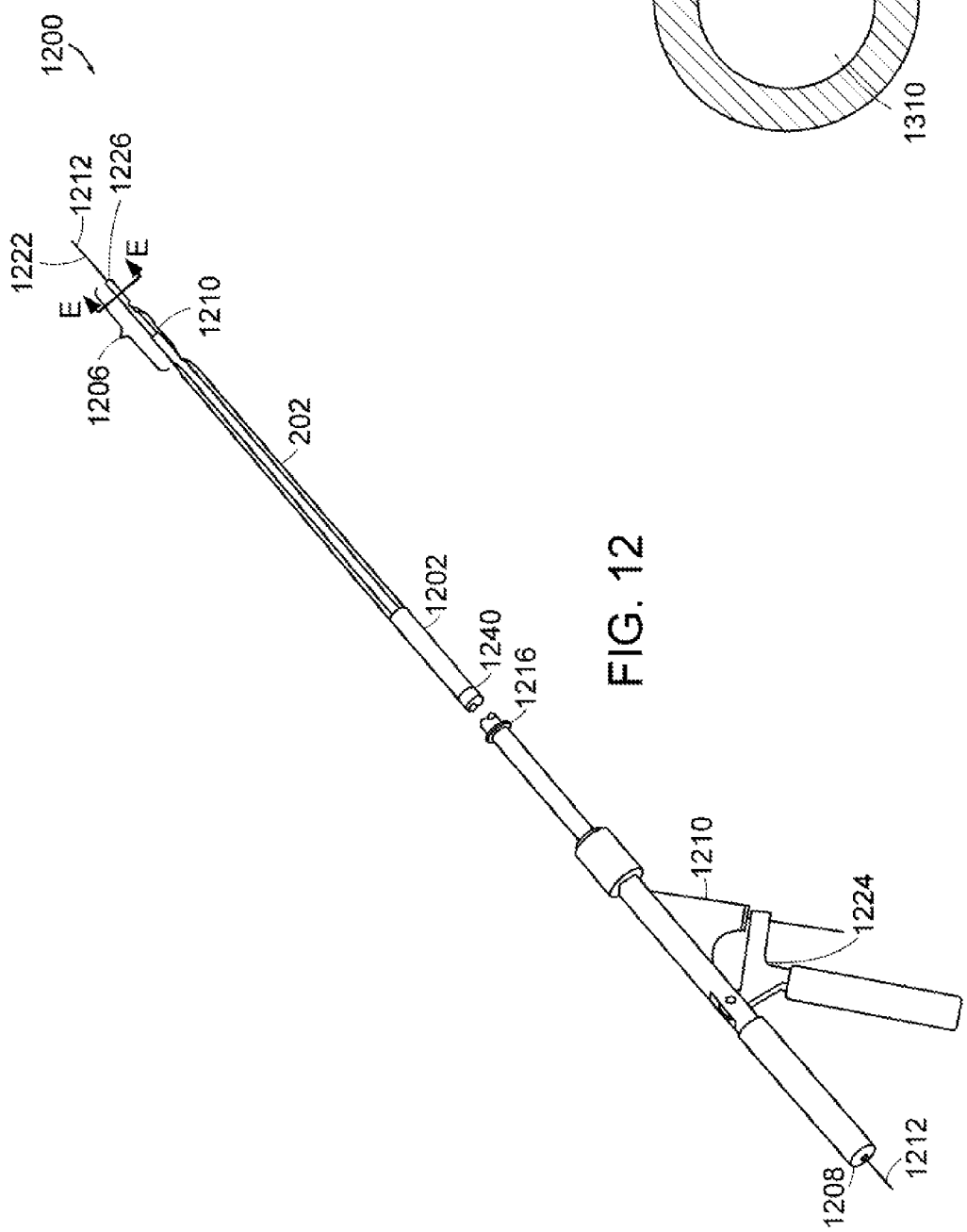
FIG. 12 is a perspective view of a catheter system for delivery of the gastrointestinal implant device.

The gastrointestinal implant device 200 is designed for catheter-based placement (e.g., endoluminal). FIG. 12 is a perspective view of a portion of a catheter system 1200 for delivery of the gastrointestinal implant device. The catheter system follows a guide wire 1212 through a natural lumen such as the esophagus and the stomach 102 and through the pylorus 108 itself. The guide wire 1212 enters a first inner lumen at the proximal end 1208 of the catheter system 1200 and exits the first inner lumen at the distal end 1222 of the catheter system 1200.

The catheter system 1200 includes an outer sheath 1202 for storing the anchor 208 in collapsed form, a flange 1216 to pull back the outer sheath 1202 and a sleeve retention wire mechanism 1224 for releasing a sleeve retention wire 1210 from the proximal end of the flexible sleeve 202 after the anchor has been released from the outer sheath 1202.

As described in conjunction with FIG. 2, the distal portion of the gastrointestinal implant device includes an unsupported flexible sleeve 202 which can negotiate the duodenum and the jejunum. A sleeve retention wire 1210 travels through a second inner lumen and exits the second inner lumen to secure the distal end of the sleeve 202 to an inner sheath 1226. The sleeve retention wire 1210 is coupled to the sleeve retention wire release mechanism 1224 for releasing the sleeve retention wire 1210 after the gastrointestinal implant device has been positioned in the duodenum 104. The release mechanism 1224 will be described later in conjunction with FIG. 16B.

The sleeve 202 is secured temporarily outside the inner sheath 1226 allowing for proper positioning of the gastrointestinal implant device and then for release. As shown, the sleeve 202 is secured by the sleeve retention wire 1210 using a dead-bolt mechanism 1206. Non-stick coatings such as Teflon on the sleeve retention wire 1210 are preferred to make release easier to accommodate tortuous anatomical pathways. The sleeve retention wire 1210 extends through the second inner lumen from the release mechanism 1224 of the catheter system 1200 to the dead-bolt mechanism 1206. The dead-bolt mechanism 1206 is described later in conjunction with FIG. 14A.

The sleeve retention wire 1210 holds the sleeve in position. The distal end of the folded sleeve is released by the release mechanism 1224 by pulling the sleeve retention wire 1210 backward from the proximal end 1208 of the catheter.

As described in conjunction with FIG. 2, the proximal portion of the gastrointestinal device includes a covered anchor. The anchor in the gastrointestinal implant device is collapsed and stored in the outer lumen within the outer sheath 1202 between the flange 1216 and the proximal end 1208 of the outer sheath 1202. The anchor is supported in a collapsed form by the outer sheath 1202. The catheter 1200 is inserted into the digestive system through the esophagus through the pyloric section of the stomach. The proximal end of the outer sheath 1202 is positioned in the duodenum through the use of positioning ring 1240. After the outer sheath 1202 has been positioned, the anchor is retracted from the outer lumen of the catheter by pulling flange 1216 toward the proximal end of the catheter system 1200. Upon release, the anchor self-expands by its own elastic restoring force to engage the anchor portion with the surrounding muscular tissue of the duodenum.

Figure 13:
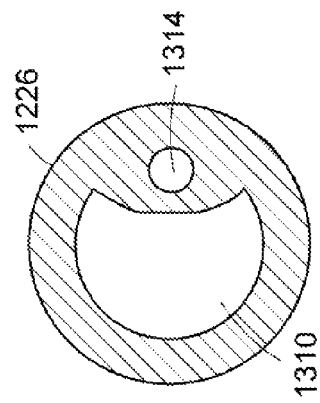
FIG. 13 is a cross-sectional view of the inner shaft taken along line E-E of FIG. 12.

FIG. 13 is a cross-sectional view of the inner shaft 1226 taken along line E-E of FIG. 12. The sleeve retention wire 1210 passes through a second inner lumen 1314 in the inner sheath 1226. The sleeve retention wire 1210 exits the second inner lumen 1314 and is threaded through folds of the sleeve 202 at 1302 in FIG. 14A. The sleeve retention wire 1210 re-enters the second inner lumen 1314 at 1302 (FIG. 14A). The guidewire 1212 passes through the first inner lumen 1310.

FIG. 14A is an expanded perspective view of the dead-bolt mechanism 1206 shown in FIG. 12. The sleeve 202 has been folded for delivery. The sleeve 202 is wrapped around the inner sheath 1226 and bunched above the inner sheath 1226. The sleeve 202 is held in folded position around the inner sheath 1226 by threading the sleeve retention wire 1210 through the folds of the sleeve 202. The sleeve retention wire 1210 exits the second inner lumen 1314 through an opening 1304 and pierces through folds of the sleeve 202 at 1304. Threading the sleeve retention wire 1210 through the folds of the sleeve 202 results in a plurality of small holes at the distal end of the sleeve 202. The holes are reinforced with silicone or urethane to avoid tears in the material. The sleeve retention wire 1210 re-enters the second inner lumen through a second hole 1302 and advances a sufficient distance within the second inner lumen toward the distal end of the second inner lumen to resist pulling out of the second inner lumen.

FIG. 14B is a sectional view of the dead-bolt mechanism 1206 shown in FIG. 14A illustrating the sleeve retention wire 1210 threaded through the sleeve 202. The sleeve retention wire 1210 exits the second inner lumen at 1306 and pierces through folds in the sleeve 202 at 104. The sleeve retention wire 1210 re-enters the second inner lumen at 1302.

FIG. 15 is a sectional view of a portion of the catheter system shown in FIG. 12 illustrating the collapsed anchor 208 stored inside the outer sheath 1202. The anchor 208 is pre-compressed and held in a collapsed form inside the outer sheath 1202 of the catheter. The outer sheath 1202 is pulled back by the flange 1216 toward the proximal end of the catheter system 1200 to release the self-expanding anchor 208. The anchor 208 radially expands under its own elastic restoring force. The guidewire 1212 is directed through the first inner lumen and the sleeve retention wire 1210 is directed through the second inner lumen in the inner sheath 1226. The inner sheath 1226 includes a first lumen through which the guidewire 1212 passes and a second lumen through which the sleeve retention wire 1210 passes.

FIGS. 16A-C illustrate a method for delivery of the gastrointestinal implant device. FIG. 16A is a plan view of the catheter system 1200 illustrating the collapsed anchor 208 stored inside the outer sheath 1202 of the gastrointestinal implant device. As described in conjunction with FIG. 12, the anchor 208 is stored inside the outer sheath and the distal end of the sleeve 202 is secured outside the inner sheath 1226 by a sleeve retention wire 1210.

FIG. 16B is a plan view of the catheter system illustrating the gastrointestinal implant device 200 after release of the anchor from the outer sheath. The flange 1216 has been pulled back toward the proximal end of the catheter system 1200 to pull back the outer sheath 1202 from the anchor 208 and the anchor 208 has self-expanded. The sleeve retention wire 1210 holds the distal end of the sleeve 202.

Once in place, the sleeve retention wire 1210 can be removed. As described previously in conjunction with FIG. 12, the sleeve retention 1210 is coupled to locking mechanism 1224. The handle 1600 in the locking mechanism 1224 acts as a pivot device to pull the sleeve retention wire 1210 from the dead-bolt mechanism 1206. The distal end of the gastrointestinal implant device 200 is released by moving handle 1600 in a clockwise direction 1604. As the handle 1600 is moved in direction 1604, the sleeve retention wire 1210 threaded through the folds of the sleeve is pulled back through the second inner lumen 1314 and disengages from the sleeve 202 at the distal end of the gastrointestinal implant device 200. The sleeve retention wire 1206 extends from the distal end of the gastrointestinal implant device 200 through the second inner lumen 1314. The wire is connected to the handle 1600 at the proximal end of the catheter.

FIG. 16C is a plan view of the catheter system 1200 illustrating the expanded gastrointestinal implant device 200 after the sleeve retention wire 1210 has been released. The handle 1600 has been moved in a clockwise direction and the sleeve retention wire 1210 pulled back through the second inner lumen 1314 to release the distal end of the sleeve 202.

Figure 17:
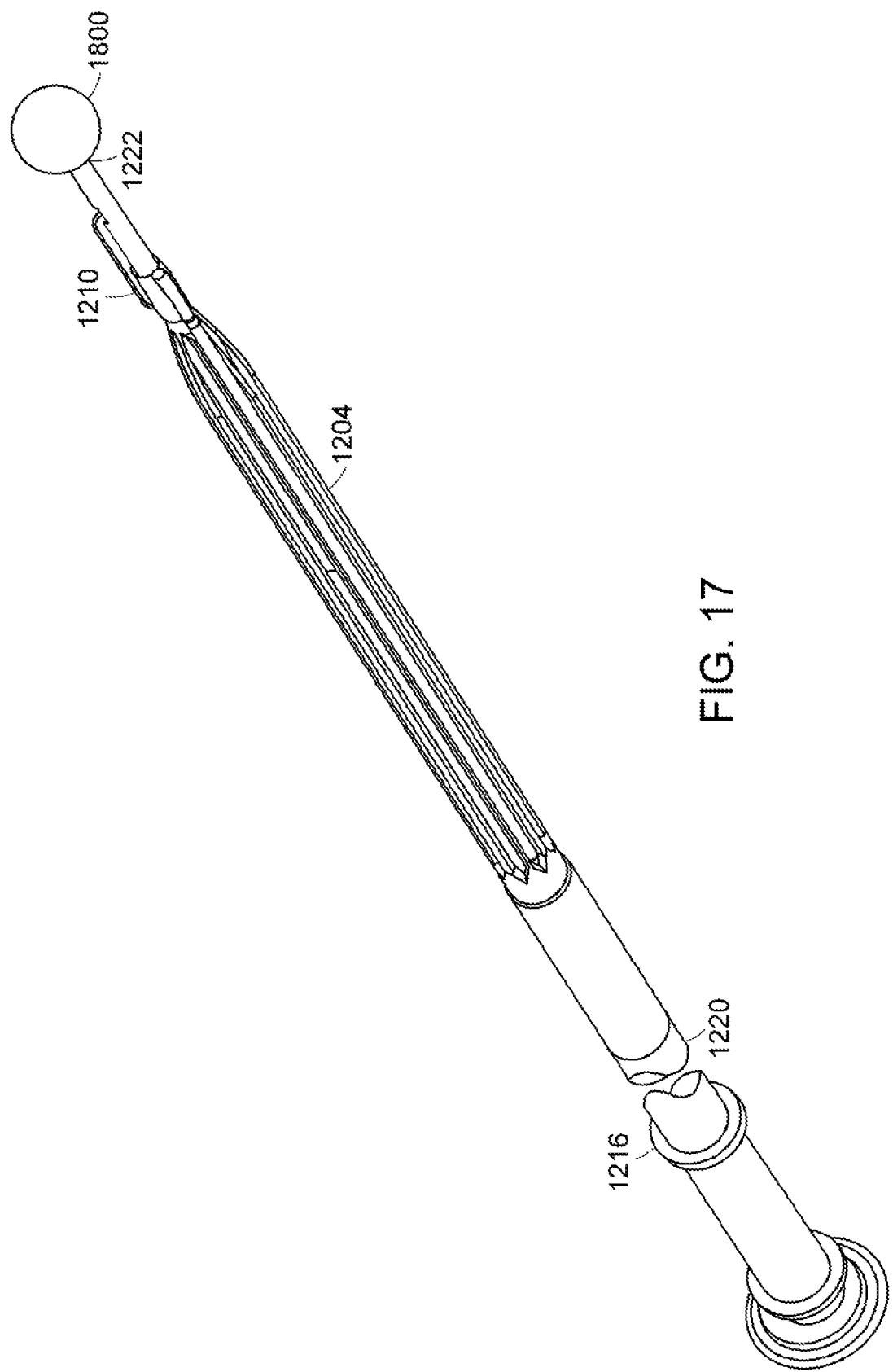
FIG. 17 is a perspective view of another embodiment of the catheter system shown in FIG. 12.

FIG. 17 is a perspective view of another embodiment of the catheter system 1200 shown in FIG. 16. The catheter includes a ball 1800 coupled to the distal end 1222 of the inner sheath 1226 for guiding the catheter through the alimentary canal to beyond the pyloric portion of the stomach 102. The ball 1800 is small enough so that it can be pulled back through the gastrointestinal implant device after the gastrointestinal device 200 has been delivered, the anchor expanded and the sleeve retention wire 1210 has been released. The sleeve 1204 is shown uniformly folded. However, the sleeve 1204 may not necessarily be uniformly folded.

Figure 18:
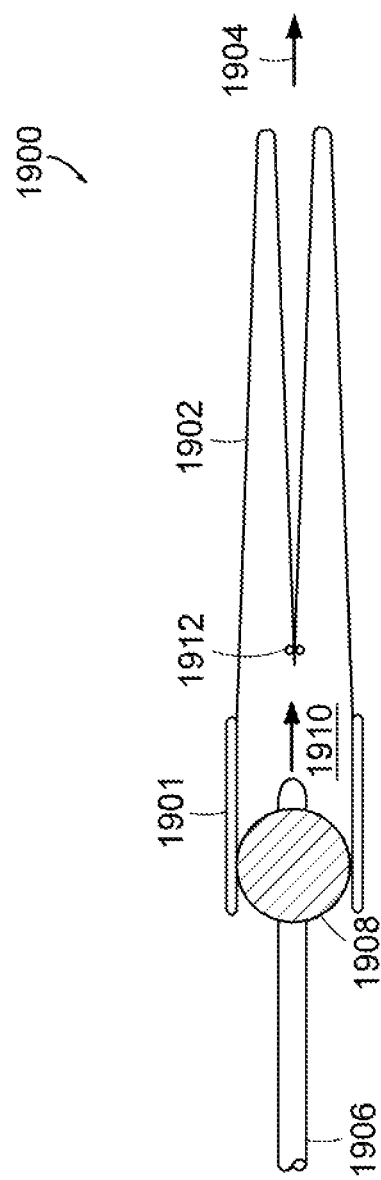
FIG. 18 is a sectional view of an everting catheter system for delivery of a longer length sleeve.

FIG. 18 is a cross-section of an everting catheter system 1900 for delivery of a longer unsupported flexible sleeve 1902. The gastrointestinal implant device 200 is shown with the sleeve anchor 1901 and the attached sleeve 1902 shown as delivered into the anatomy. The delivery catheter previously described is then removed. A balloon catheter 1906 is introduced into the sleeve anchor 1901 and the balloon 1908 inflated to seal the lumen of the anchor 1901. The sleeve 1902 is folded inside itself and an elastic band 1912 is used to seal the end of the sleeve. Fluid is then injected through the balloon catheter shaft 1906 into the sleeve lumen 1910, filling the lumen and pressurizing it. The pressure of the fluid is used to push the inner sleeve distally towards 1904. When the sleeve 1902 has fully deployed distally, the elastic band 1912 falls off of the closed end of the sleeve 1902 and passes distally in the intestine until it is excreted. This mechanism permits deployment of a sleeve that is longer than (e.g., double) the length of the delivered device. This may be needed as it is difficult to access the distal parts of the intestine with guidewires. This everting catheter system 1900 enables delivery of longer sleeves than are possible using only the delivery catheter described in conjunction with FIG. 12.

Figure 19:
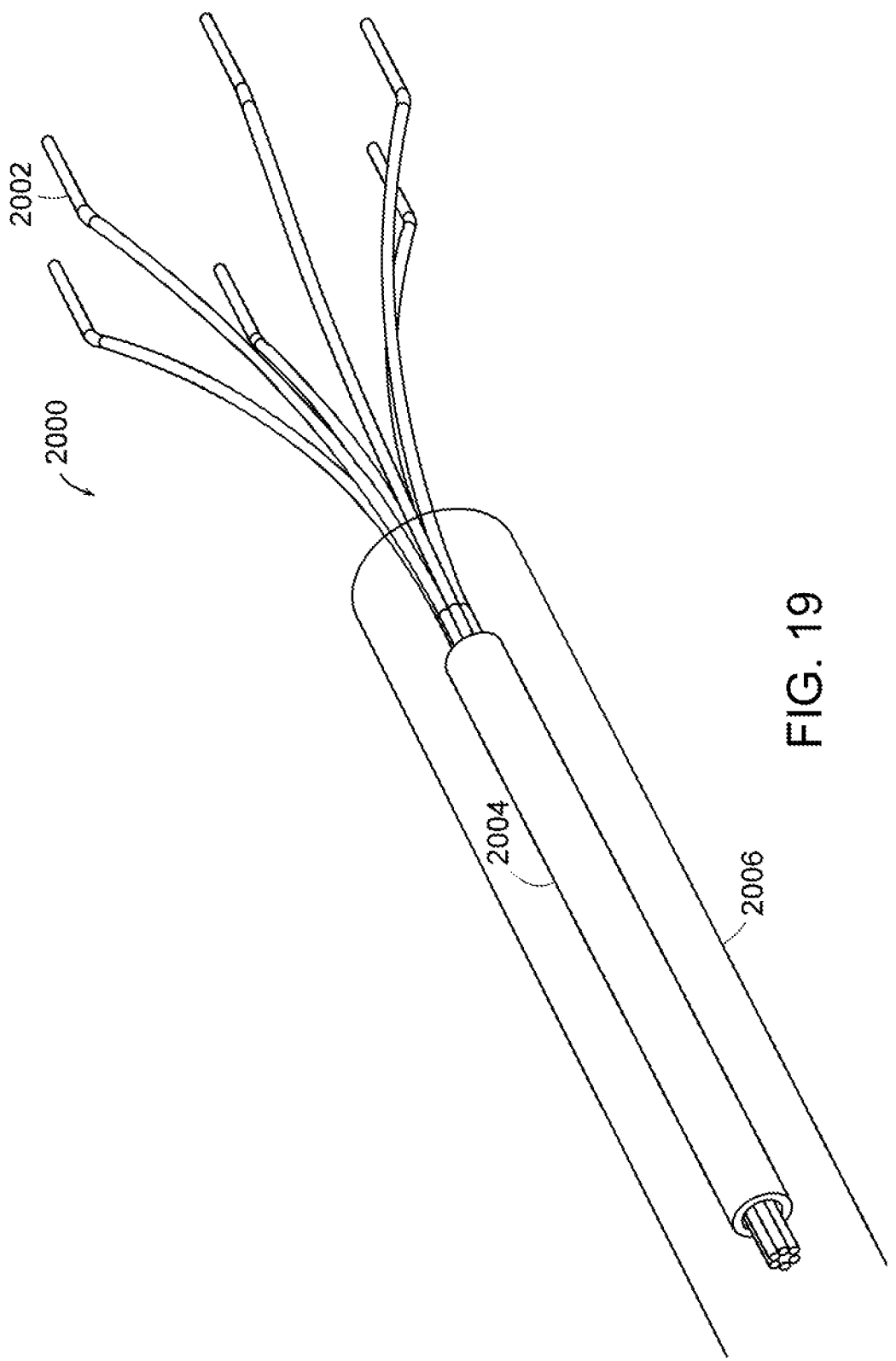
FIG. 19 is a perspective view of a retrieval device for removing the gastrointestinal implant device from the digestive tract.

FIG. 19 is a perspective view of a retrieval device 2000 for removing the gastrointestinal implant device 200 from the digestive tract. As already described, the exterior surface of the anchor 208 can be covered with a material that prevents cellular in-growth allowing the anchor 208 to be easily removed. The retrieval device 2000 includes an inner sheath 2004 and an outer sheath 2006. A plurality of fingers 2002 extend from the proximal end of the inner sheath 2004. The fingers 2002 engage the exterior surface of the gastrointestinal device. As the inner sheath 2004 is moved down over the fingers, the fingers 2002 pull radially inward to reduce the proximal anchor diameter and pull the collapsed device into the outer sheath 2006.

Figure 20:
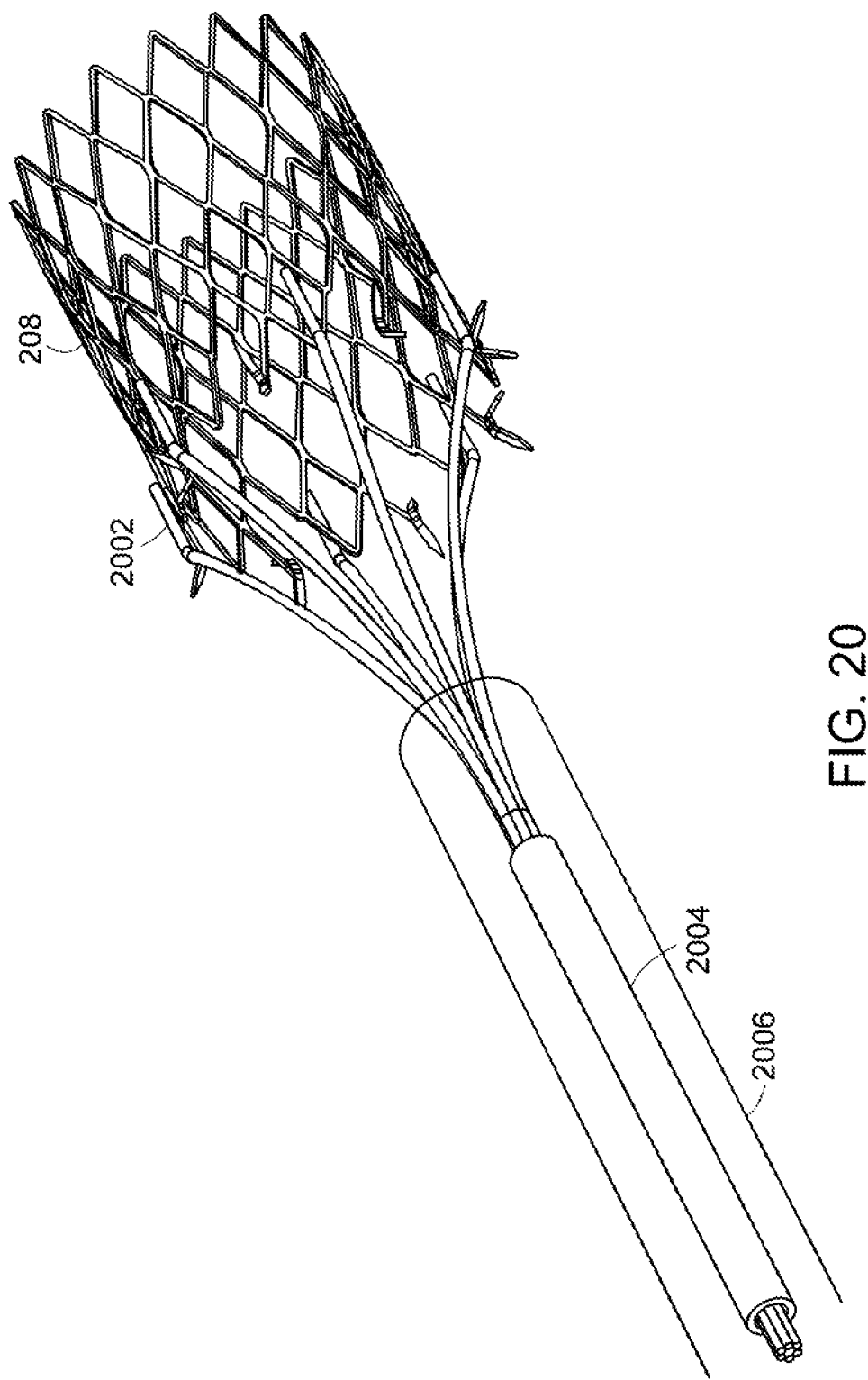
FIG. 20 is a perspective view of the removal device engaged with the anchor.

FIG. 20 is a perspective view of the retrieval device 2000 engaged with the anchor 208. The fingers 2002 of the retrieval device are positioned around the anchor 208. As the inner sheath 2004 is pushed over the fingers 2002, the fingers pull radially inward on the proximal end of the anchor 208 and the proximal end of the anchor 208 is collapsed. After the anchor 208 has been collapsed sufficiently such that the proximal anchor diameter is less than the diameter of the outer sheath 2006, the anchor is drawn into the outer sheath 2006. The entire gastrointestinal implant device can then easily be removed from the patient by pulling retrieval device 2000 through the stomach and the esophagus.

In another embodiment, the anchor 208 can be configured with a drawstring. The drawstring can be selectively woven around the perimeter of the anchor 208 through openings of opportunity in the anchor 208. The openings can be defined by adjacent interconnected struts of the anchor 208. Alternatively, or in addition the drawstring can be selectively woven through dedicated openings, such as eyelets provided on the anchor 208. In some embodiments, the drawstring is woven through openings at the proximal end of the anchor 208. In operation, the drawstring can be pulled in a proximal direction by a retrieval device. The drawstring, when pulled, contracts about the perimeter of the anchor 208, thereby reducing the diameter of the anchor 208. Thus, the drawstring can be used to facilitate removal of an implanted anchor 208 by pulling it away from the surrounding anatomy thereby extracting any barbs from the surrounding muscular tissue.

Figure 21:
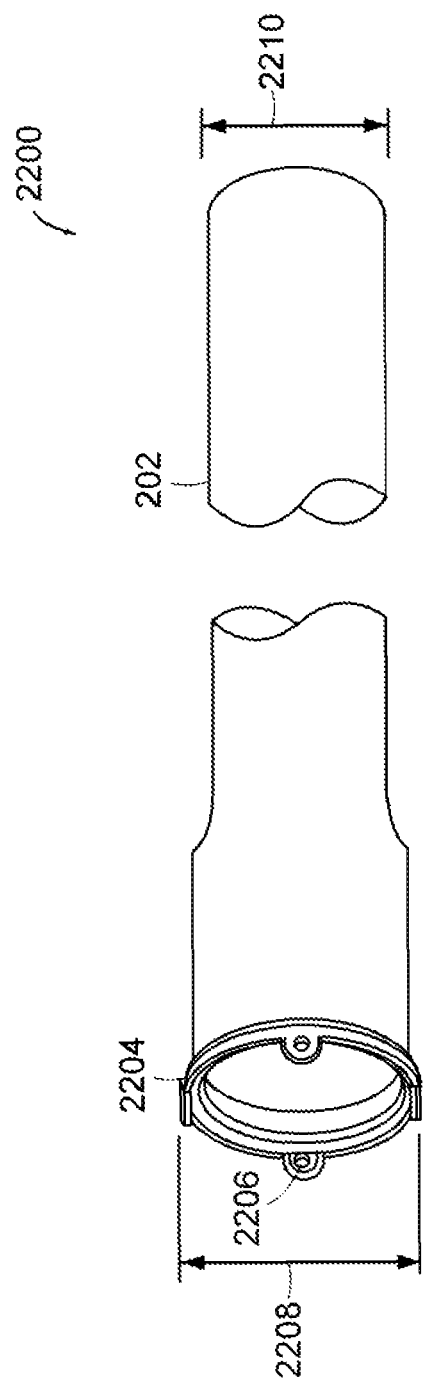
FIG. 21 is a perspective view of another embodiment of a gastrointestinal implant device.

FIG. 21 is a perspective view of another embodiment of a gastrointestinal implant device 2200. The gastrointestinal implant device 2200 includes a sleeve 202 and an anchoring ring 2204. The distal end of the anchoring ring 2204 is bonded to the proximal end of the sleeve 202. A plurality of eyelets 2206 are distributed around the circumference of the proximal end of the ring for anchoring the device to the muscular tissue of the duodenum 104 using anchors shown in FIG. 24. The anchoring ring 2204 is made from a flexible, biocompatible material such as silicone allowing the ring 2204 to be collapsed for catheter-based insertion and removal. Preferably, the anchoring ring 2204 does not interfere with the normal opening and closing of the pylorus 108.

Figure 22:
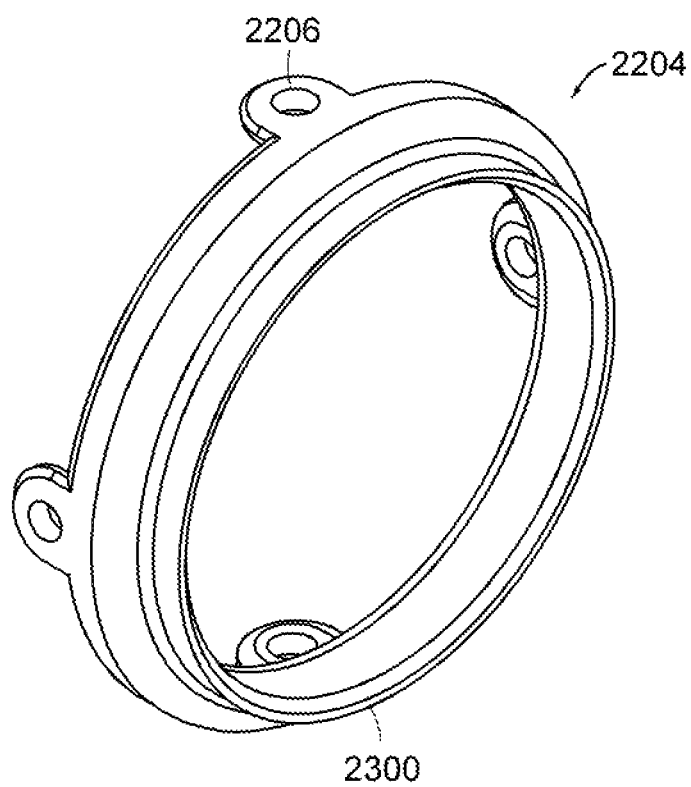
FIG. 22 is a perspective view of the anchoring ring shown in FIG. 21.

FIG. 22 is a perspective view of the anchoring ring 2204 shown in FIG. 21 in the expanded position. The sleeve 202 is bonded to the outer surface 2300 of the proximal end of the anchoring ring 2204 whose diameter is 1 inch or about the same as the diameter of the sleeve 202. The anchoring ring 2204 includes at least four eyelets 2206 to anchor the device 2200 in place. The outer most diameter of the ring 2204 is about one inch. In an alternate embodiment there can be more than four eyelets 2206.

Figure 23:
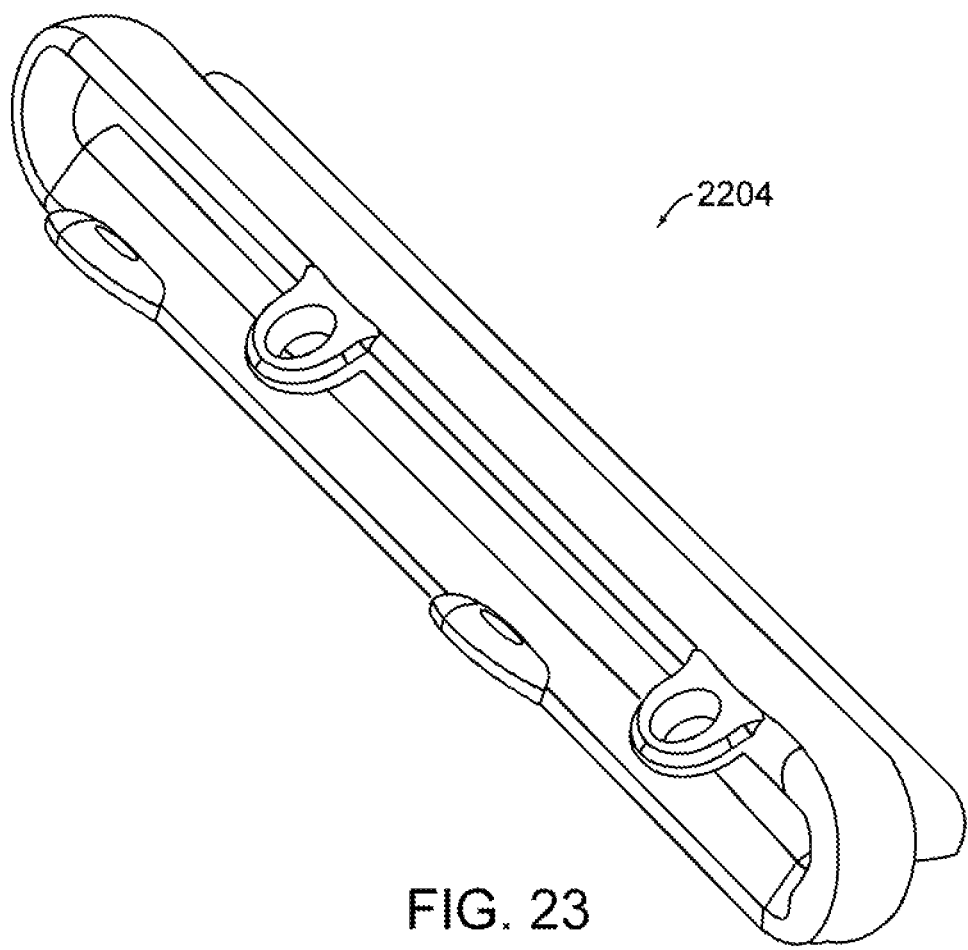
FIG. 23 is a perspective view of the anchoring ring shown in FIG. 21 in a collapsed position for insertion and removal.

FIG. 23 is a perspective view of the anchoring ring 2204 shown in FIG. 21 in a collapsed position for insertion and removal. The circular ring 2204 shown in FIG. 21 has been compressed to an oval shape allowing the anchoring ring to be inserted into the lumen of a catheter for delivery.

Figure 24:
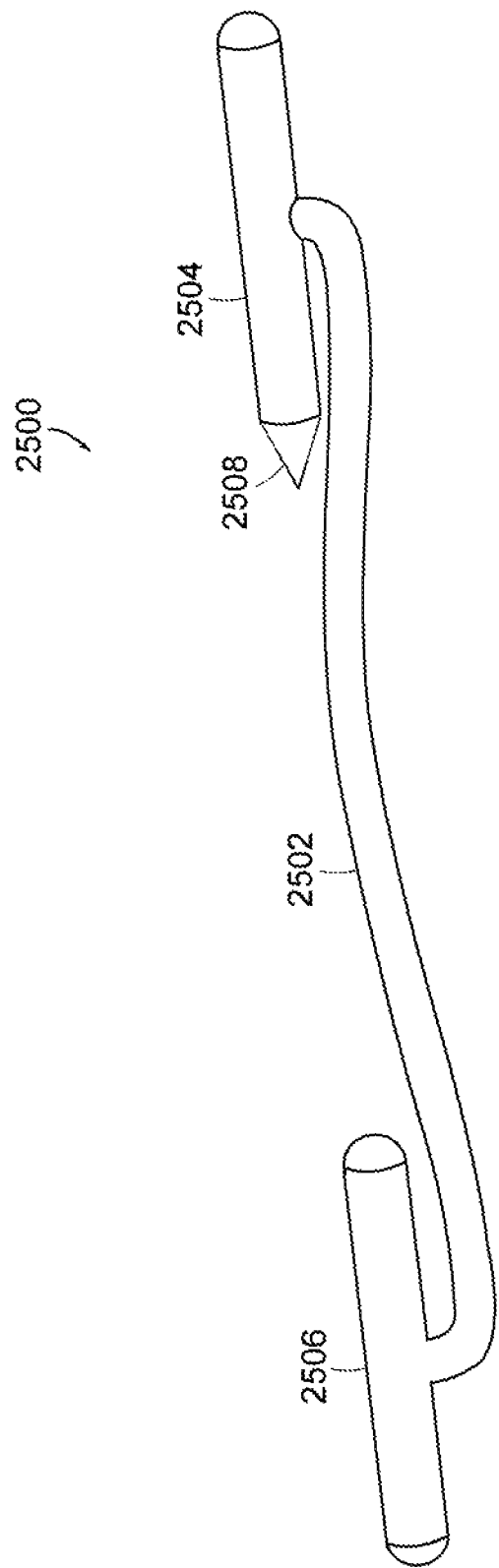
FIG. 24 is a perspective view of an anchor for anchoring the collapsible ring shown in FIG. 23 to the muscular tissue of the duodenum.

FIG. 24 is a perspective view of an anchor 2500 for anchoring the collapsible ring shown in FIG. 23 to the muscular tissue of the duodenum 104. The anchor 2500 includes an anchor pin 2504 coupled to a second pin 2506 by a flexible shaft 2502. The anchor pin 2504 includes a shaped barb 2508 for locking the anchor 2500 into the tissue. The anchor 2500 is delivered after the collapsible ring has been positioned in the duodenum 104. The anchor 2500 is guided so that the anchor pin 2504 is directed through a respective eyelet 2206 with the barbed portion of the anchor pin 2504 guided toward the tissue. After the barb 2508 has been locked into the tissue, the second pin 2506 sits inside the gastrointestinal implant device while the barbed portion 2508 of the anchor pin 2504 sits inside the muscular tissue of the duodenum 104. For removal of the gastrointestinal implant device from the body, the flexible shaft 2502 of the anchor 2500 is cut.

FIG. 25A is a perspective view of a delivery system 2600 for delivering the anchor 2500 after the gastrointestinal implant device has been placed in the duodenum 104. The anchor 2500 is loaded in the distal end of a catheter having a single lumen tube 2600. The hollow, distal end of the delivery device 2600 is a sharp needle made to penetrate the muscular tissue of the duodenum 104. In an alternate embodiment, the distal end of the delivery device 2600 can be formed in an arc to improve access to the eyelets 2206 through an endoluminal approach. The catheter 2600 includes a pusher 2604 for releasing the anchor 2500. The pusher 2504 is moved in a longitudinal direction 2602 to release the anchor 2500 from the lumen.

FIG. 25B is a plan view of the delivery system 2600 shown in FIG. 25A. FIG. 25C is a cross-sectional view of the distal end of the catheter 2600 as taken along line B-B of FIG. 25B. As described in conjunction with FIG. 24, the anchor 2500 includes pins 2504, 2506 coupled by a flexible shaft 2502. The anchor 2500 is loaded in the lumen at the distal end of the catheter 2600. The anchor pin 2504 is placed in the distal end of the tube 2600 and the second pin 2506 in the proximal end. The barb 2508 on the anchor pin 2504 is pointed toward the proximal end of the tube 2506 to engage with the tissue upon release in the muscle tissue. The catheter 2600 is advanced to the center of the ring positioned in the duodenum 104. The sharp end 2510 is then pushed through an eyelet 2206 and into the surrounding muscular tissue. The pusher 2506 is pushed in longitudinal direction 2602 to release the distal anchor 2506. Once the distal anchor 2506 is released, the delivery system 2600 is pulled back, dragging the proximal part of the anchor out of the delivery device with the flexible shaft going through the eyelet 2206, and the proximal anchor portion resting on the inside of the device. In the embodiment of the ring shown in FIG. 22, four anchors 2506 are delivered to anchor the gastrointestinal implant device through the four eyelets.

FIG. 25D is an isometric view illustrating the sharp end 2510 of the needle inserted through an eyelet 2206 for delivery of the anchor 2500 to the tissue 2512. The distal end of the catheter is formed in an arc 2520 to improve access the eyelets 2206. The sharp end 2510 of the catheter is inserted through the eyelet 2206 into the tissue 2516. The anchor pin 2504 of the anchor has been pushed out from the lumen into the tissue 2512.

FIG. 25E is an isometric view illustrating the barb 2508 engaging the tissue 2512 after delivery. The catheter has been removed from the eyelet 2206 leaving the anchor pin 2504 engaging the tissue 2516.

FIGS. 26A-E illustrate an alternative embodiment of a locking mechanism for holding the distal end of the sleeve 202 in position during delivery of the gastrointestinal implant device 200. The snare wire 2656 is passed through one of the lumens of the catheter 2650 to the distal end. At the distal end, the end of the snare wire 2656 is looped back and attached to or anchored inside the catheter 2650. The folds of the sleeve 202 are advanced through this snare loop. The snare handle 2664 pulls and releases the snare wire 2656 to lock and release the distal end of the sleeve 202. The delivery system 2600 includes a pull tap 2666 for releasing a drawstring holding the anchor in a collapsed position.

FIG. 26B is cross-sectional view taken along line C-C of FIG. 26A through the inner sheath 2650. The inner sheath 2650 has two lumens 2654, 2656 and has a diameter of about 0.078 inches. The first inner lumen 2564 is for passing a guidewire through the inner sheath and is about 0.04 inches in diameter. The second inner lumen 2656 is for passing the snare wire 2656 through the inner sheath 2650 is about 0.02 inches in diameter. The end of the snare wire 2658 is anchored inside the inner sheath 2650.

FIG. 26C is a cross-sectional view taken along line DD of FIG. 26A through the outer sheath 2600 showing the inner sheath 2650 within the outer sheath 2600. The outer sheath 2600 has an inner diameter of about 0.1 inches and an outer diameter of about 0.143 inches. The open space inside the outer sheath 2600 can be used for passing a drawstring through the outer sheath 2600.

Figure 26D:
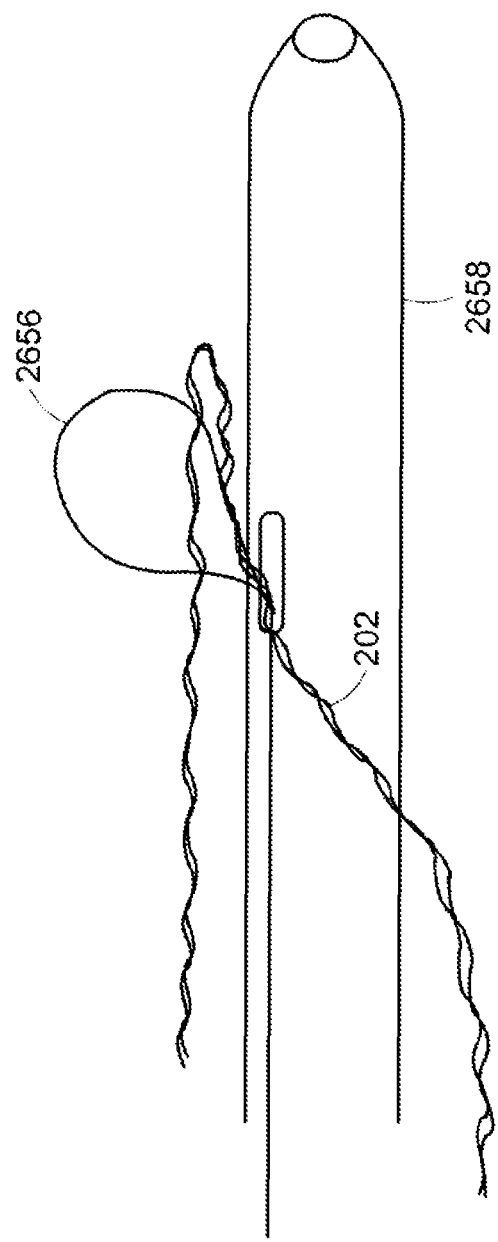
FIG. 26D is a cross-sectional view through the distal portion of the catheter showing the snare capturing the distal end of the sleeve.

FIG. 26D is a cross-sectional view through the distal portion of the catheter showing the snare 2656 capturing the distal end of the sleeve 202. The distal end of the sleeve 202 is captured by the snare wire 2656 by pulling the distal end of the sleeve 202 through a loop formed by the snare wire 2656.

Figure 26E:
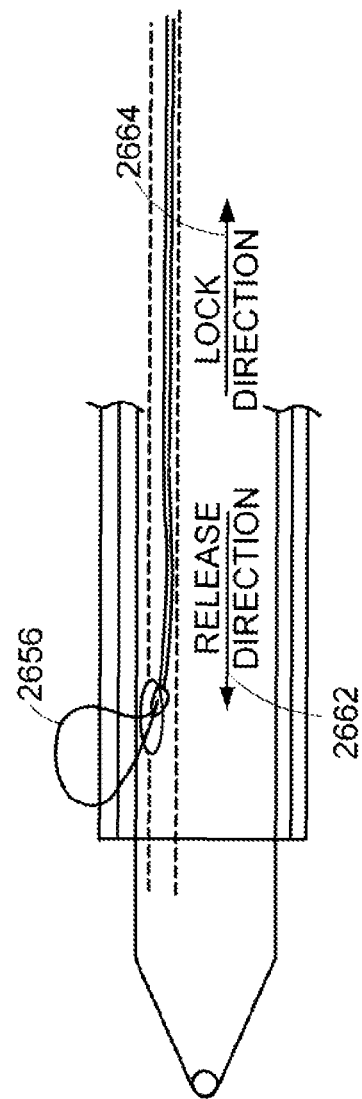
FIG. 26E is a sectional view through the distal portion of the catheter showing the snare locking mechanism.

FIG. 26E is a sectional view through the distal portion of the catheter showing the snare locking mechanism. The distal end of the sleeve 202 is locked by pulling the snare wire 2656 in a longitudinal direction 2664 toward the proximal end of the delivery system to capture the sleeve folds against the inner shaft. After the gastrointestinal implant device 200 is properly positioned in the body, the snare wire 2656 is advanced in a longitudinal direction 2662 toward the distal end of the delivery system. This opens the snare wire 2656 and releases the sleeve 202.

Figure 27:
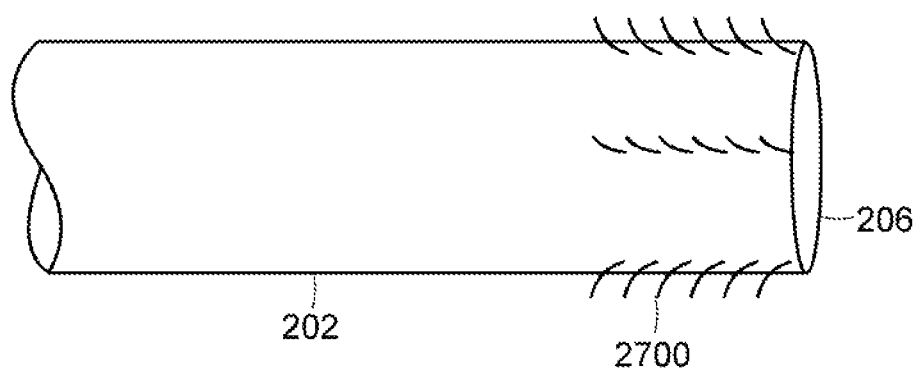
FIG. 27 is a perspective view of the distal portion of the gastrointestinal implant device including texturing at the distal end.

FIG. 27 is a perspective view of the distal portion of an embodiment of the gastrointestinal implant device including texturing 2700. Texturing of the distal end of the sleeve 202 can be added to ensure that the actions of peristalsis do not advance the sleeve 202 proximally, towards the stomach 102, but keep the sleeve 202 pulled taught in the intestine 112. At the distal end of the sleeve 202, texturing 2700 is added with a directional aspect to it. The texturing 2700 can be molded into the sleeve material or added by adhesive or thermal bonding methods. The texturing material contains fibril shapes that are directed proximally so that any peristaltic waves that travel proximally, will have less force on the sleeve than distal peristaltic waves.

The gastrointestinal implant device offers a new alternative where other means of weight loss and efforts at behavior modification have failed. Because the gastrointestinal implant device is introduced through a small diameter catheter (e.g., endoluminally), there is a reduced risk at insertion compared to surgery. The procedure is also completely reversible, making this approach the ideal solution for patients who are desperate to reverse behavioral patterns that have lead to weight gain.

When inserted in the body, the gastrointestinal implant device mimics the duodenal bypass of the Roux-en-Y procedure. The implanted device reduces caloric absorption by delaying enzyme mixing with food and provides the feedback produced by the Roux-en-Y procedure by producing dumping syndrome when high sugar meals are ingested. The implant device is an improvement on the Roux-en-Y procedure because it is minimally invasive and reversible. In the treatment of the super-obese where aggressive weight loss is not achieved, the length of the implant device below the anchor can be further increased to drive the patient close to the point of malabsorption.

Placement of the gastrointestinal implant device effectively provides that ingested food does not digest in a normal manner and the gut hormones that are normally triggered are modified. These hormones result in several physiology changes that impact hunger and digestion. Gut hormones include peptide YY (PYY), cholecystokinin (CCK) and ghrelin.

As under digested food enters the ileum or distal part of the small intestine 112, a hormone called peptide YY or PYY is released. This hormone has been shown to have a direct effect on appetite, reducing it when released. Undigested food in the ileum indicates that too much food has been ingested. Thus, dependent on the length of the sleeve, the gastrointestinal device can promote deposition of undigested or partially digested food to the distal bowel. Therefore, the placement of a sleeve in the intestine promotes the delivery of undigested food to the ileum, which in turn promotes the release of PYY and reduces appetite in humans.

The hormone cholecystokinin (CCK) is released when food contacts the duodenum 104. CCK triggers the release of bile from the gallbladder. Therefore, placing a sleeve in the duodenum 104 reduces the release of CCK and thus reduces bile output resulting in reduction in the digestion of food.

Some ghrelin is released when food contacts the duodenum 104. Ghrelin has been shown to be a factor in the control of appetite. This device will reduce ghrelin output and thereby reduce appetite due to the bypass of the duodenum 104.

Type-2 diabetes is a disease of obesity that occurs when patients cannot adequately use the insulin they produce. Usually, it is not that the patient cannot make enough insulin, but rather that the patient's body cannot effectively use the insulin produced. A particularly dangerous result of Type-2 diabetes is that blood sugar spikes after a meal. This is called post-prandial hyperglycemia. This spike in blood glucose causes cardiovascular and microvascular damage. One class of drugs used to control post-prandial hyperglycemia is the alpha-glucosidase inhibitors. These work by reducing the breakdown and absorption of carbohydrates to sugars. The sleeve has a similar function because it reduces bile and delays the breakdown and absorption of the carbohydrates, which are normally readily absorbed in the duodenum, but are less likely to be absorbed in the jejunum and ileum. Therefore, type 2 diabetes can be controlled by placing a sleeve in the proximal intestine to delay the digestion of carbohydrates which reduces post-prandial hyperglycemia.

The gastrointestinal implant device can be used to reduce Type-2 diabetes symptoms by bypassing the duodenum 104. Following gastric bypass surgery, patients commonly experience complete reversal of Type-2 diabetes. While the exact mechanism of this remarkable effect is not understood, the clinical result is reported in a high percentage of cases. Reversal of Type-2 diabetes after gastric bypass is described in "Potential of Surgery for Curing Type-2 Diabetes Mellitus" by Rubino et al. incorporated herein by reference in its entirety. Since the gastrointestinal implant device provides equivalent blockage of duodenal processes, a similar effect is elicited but without the trauma of surgery. In patients who are not obese but suffer Type-2 diabetes, a modified gastrointestinal implant device is inserted. This gastrointestinal implant device provides the necessary effect to hinder pancreatic processes and receptors without blocking absorption.

In the embodiment of the gastrointestinal implant device for treating diabetes, placement of the anchor within the stomach and/or duodenum allows the pylorus 108 to operate normally. The length of the sleeve may be reduced to mimic the duodenum bypass. The sleeve extends to just below the ligament of Treitz 118 but may not extend further into the jejunum 106, thus allowing absorption to occur in the jejunum 106.

The gastrointestinal implant device can be placed temporarily in the duodenum 104 to allow tissues to heal. For example, the sleeve can be placed temporarily to promote healing of ulcers in the duodenum 104. Ulcers are lesions that form in tissues of the duodenum 104. If they bleed, they are typically cauterized with electrosurgery. For ulcers to heal, they must be protected from the acidic environment. Placement of a sleeve for a short time period, for example, for one to two weeks, promotes healing of ulcers in the duodenum 104 by eliminating the acidic environment and allows the tissues to heal.

Intestinal anastomoses are performed to remove sections of diseased bowel. The stapled or sewn connection is prone to leakage until it heals. The placement of the gastrointestinal implant device temporarily in the bowel can be used to promote healing of small bowel anastomoses by protecting the area from chyme and minimizing leaks.

The gastrointestinal implant device can be used to deliver drugs, hormones and other active agents directly to the intestine. To deliver the agents, the sleeve and/or anchor is either coated or impregnated with the agents. The agents can include anti-inflammatory agents to reduce irritation due to placement of the anchor within the body. The agents can optionally or in addition include anti-hunger hormones.

The two most common intestinal bowel diseases are Crohn's disease and Ulcerative Colitus. Crohn's disease may occur in any part of the digestive tract. Although the exact cause of the disease is unknown, it appears to be an abnormal immune response in the patient, which leads to chronic inflammation of the intestinal lining.

Crohn's disease is treated with drugs intended to reduce inflammation. These include aminosalicylates, corticosteroids, immune modifiers such as azathioprine and methotrexate and antibiotics including ampicillin and cipro. These drugs have negative effects when given systemically. Since the drug is really only needed locally, smaller amounts of drug can be used if delivered directly to the tissues. Thus, an implanted sleeve treated with such a drug advantageously treats the surrounding tissues.

The intestinal sleeve can be coated with polymers that are impregnated with these drugs. Coatings may include polyurethanes, silicones and hydrophilic polymers such as those available from Hydromer of Somerville, N.J. These coatings may be applied to the sleeve material by dipping or spraying techniques. If a porous sleeve material such as ePTFE is used, the drug-filled polymer may be driven into the pores using pressure applied to the sleeve, such as internal pressure inside the sleeve. This increases the amount of drug that is available.

The sleeve material can also be a polymer that permits the incorporation of the drug directly into the wall. Such polymers include Ethylene Vinyl Acetate (EVA) and polyurethane. A greater amount of the drug may be incorporated in this case compared to a coating since there is more material in the wall than simply in coatings, thereby providing longer release times. The drug is compounded into the polymer and then extruded as is normally done to form the tubing or sheet from which the sleeve is made.

The sleeve is deployed transesophageally into the duodenum 104 and proximal jejunum 106. When the sleeve comes in contact with the tissues, the drugs in the coating are released directly into the tissues. Also, the sleeve may act to block the contact of the food to the mucosa, thereby reducing irritation caused by the chyme. Once the drug has fully eluted from the material, the sleeve is removed and a new one is placed.

The control of appetite in the human is a complex function of hormonal interactions. Several hormones have been implicated in its control including Ghrelin, Peptide YY, Leptin, Glucagon-Like Peptide-1 (GLP-1), Cholecystokinin (CCK), insulin and others. These hormones are either released or suppressed by the presence of food in the duodenum. For example, PYY acts as an anti-hunger hormone as injections of PYY have been shown to decrease food intake in both rats and humans and decreases in leptin have been shown to stimulate hunger.

Sleeves that are located in the duodenum 104 where many of these hormones are released may be impregnated with these hormones. When implanted, the hormones elute from the sleeve into the surrounding tissue where they activate the various satiety mechanisms.

Figure 28:
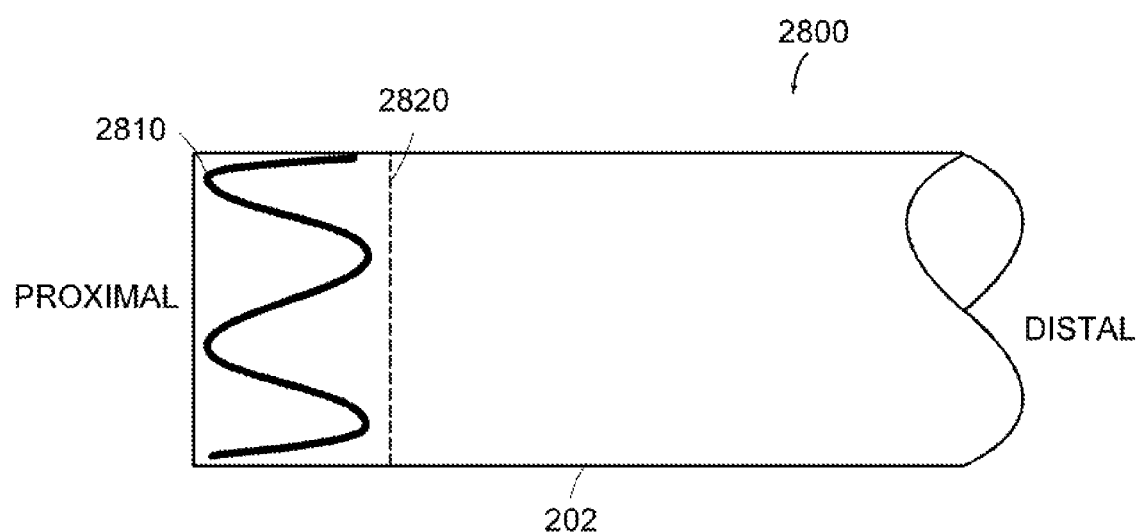
FIG. 28 is a perspective view of a gastrointestinal implant device with another embodiment of an anchoring device.
Figure 29:
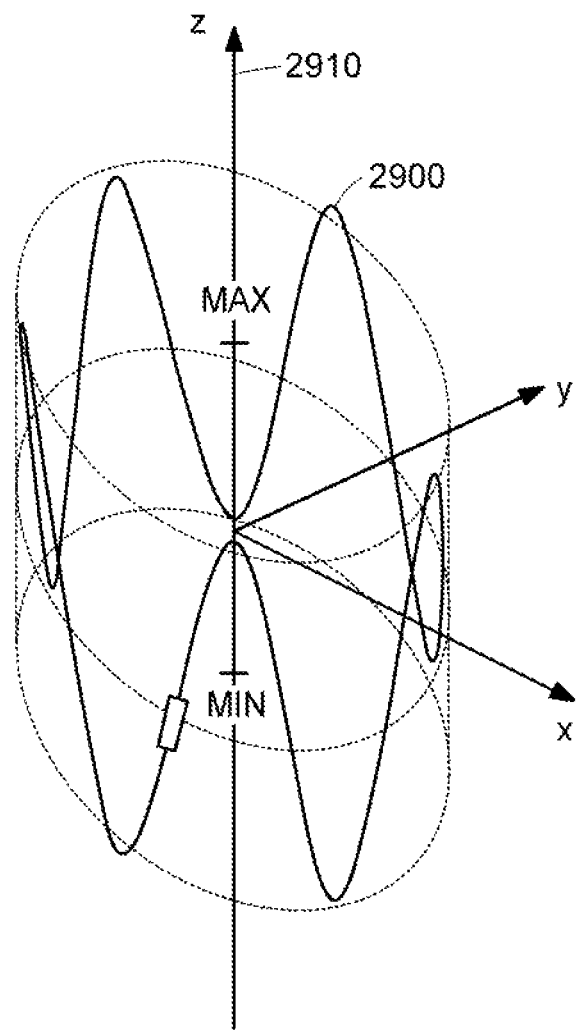
FIG. 29 is a more-detailed perspective view of the anchoring device of FIG. 28.
Figure 30:
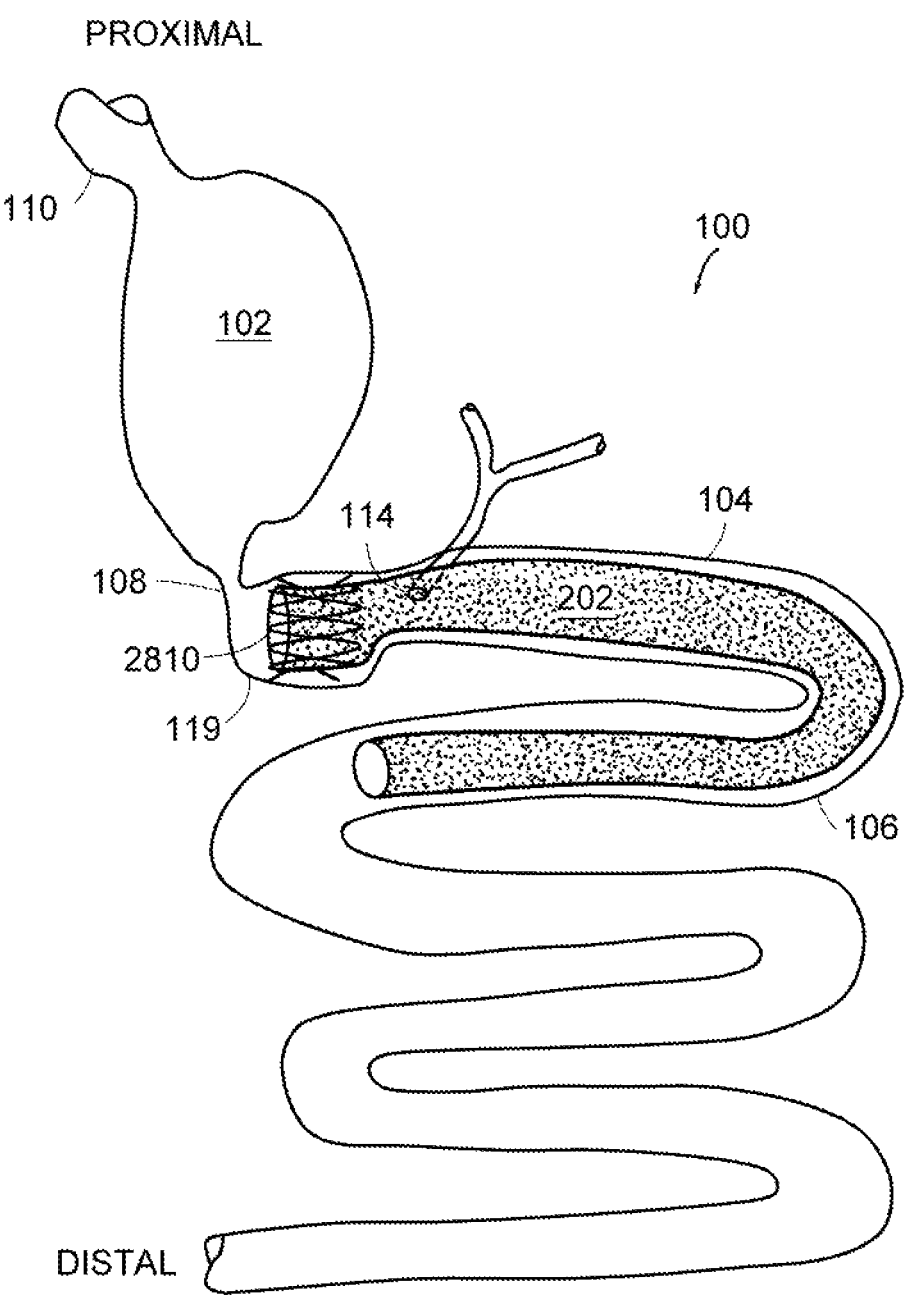
FIG. 30 is a is a sectional view of a body showing the gastrointestinal implant device of FIG. 28 implanted in the digestive system.

FIG. 28 is a perspective view of a gastrointestinal implant device with another embodiment of a collapsible self-expanding anchoring device. The gastrointestinal implant device 2800 includes a sleeve 202 and an anchoring device 2810 for anchoring the gastrointestinal implant 2800 device in the duodenum 104. The anchoring device 2800 includes a wave anchor 2810 coupled to a proximal portion of the sleeve 202. Referring to FIG. 29, the wave anchor 2810 includes a compliant, radial spring 2900 shaped into an annular wave pattern about a central axis 2910, providing an outward radial force, while allowing substantial flexure about its perimeter. Such flexure is advantageous as it allows for minimally-invasive delivery and ensures that the device will substantially conform to the surrounding anatomical structure when implanted. The annular wave element 2900 can be formed from one or more elongated resilient members and defines a lumen along its central axis formed between two open ends. When implanted, as shown in FIG. 30, the central axis of the anchor 2810 is substantially aligned with the central axis of the duodenum 104, allowing chyme to pass through the device 2800. Additionally, the compliant wave anchor 2810 minimizes trauma to the tissue by providing sufficient flexibility and compliance, while minimizing the likelihood of tissue erosion and providing a solid anchoring point to the tissue.

The compliant wave anchor 2810 can be manufactured from a resilient metal such as a heat-treated spring steel, stainless steel, or from an alloy such as NiTi alloy commonly referred to as Nitinol. Other alloys include nickel-cobalt-chromium-molybdenum alloys possessing a unique combination of ultrahigh tensile strength, such as MP35N. Additionally, the wave anchor 2810 can be formed from a polymer and/or a composite having similar properties. The wave anchor 2810 can be manufactured from a single strand, such as a wire, contoured into the desired shape. Alternatively, the wave anchor 2810 can be manufactured from multi-strands of the same or different materials similarly contoured to the desired shape. In some embodiments, the wave anchor 2810 can be cut into the wave shape from tubular stock of the desired material, such as Nitinol.

Figure 31:
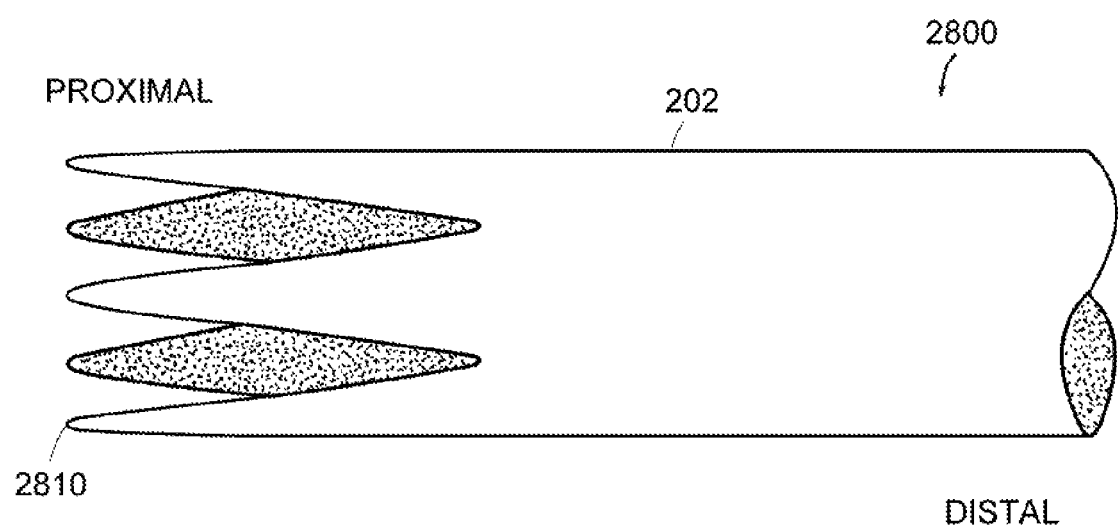
FIG. 31 is a perspective view of an alternative embodiment of the gastrointestinal implant device of FIG. 28.

The anchor 2810 can be removably attached within the body using any of the methods described herein for securing a anchor 208, including the use of barbs attached to, and/or formed on the anchor itself. When implanted, the anchor 2810 enables a sleeve 202, or barrier to be securely implanted within the duodenum 104, preferably providing a fluid seal at the proximal end. To enhance a fluid seal, the proximal end of the sleeve can be contoured to the wave anchor as shown in FIG. 31. For a device 2800 using a sleeve 202 contoured to the wave anchor 2810, proximal end appears tulip-shaped.

In an embodiment according to the invention, the anchor has a relaxed diameter of at least about 40 millimeters. The anchor preferably has a minimal relaxed diameter of at least about 45 millimeters. The anchor, when implanted, preferably has a diameter of about 30 to 35 millimeters.

Figures 32A, 32B:
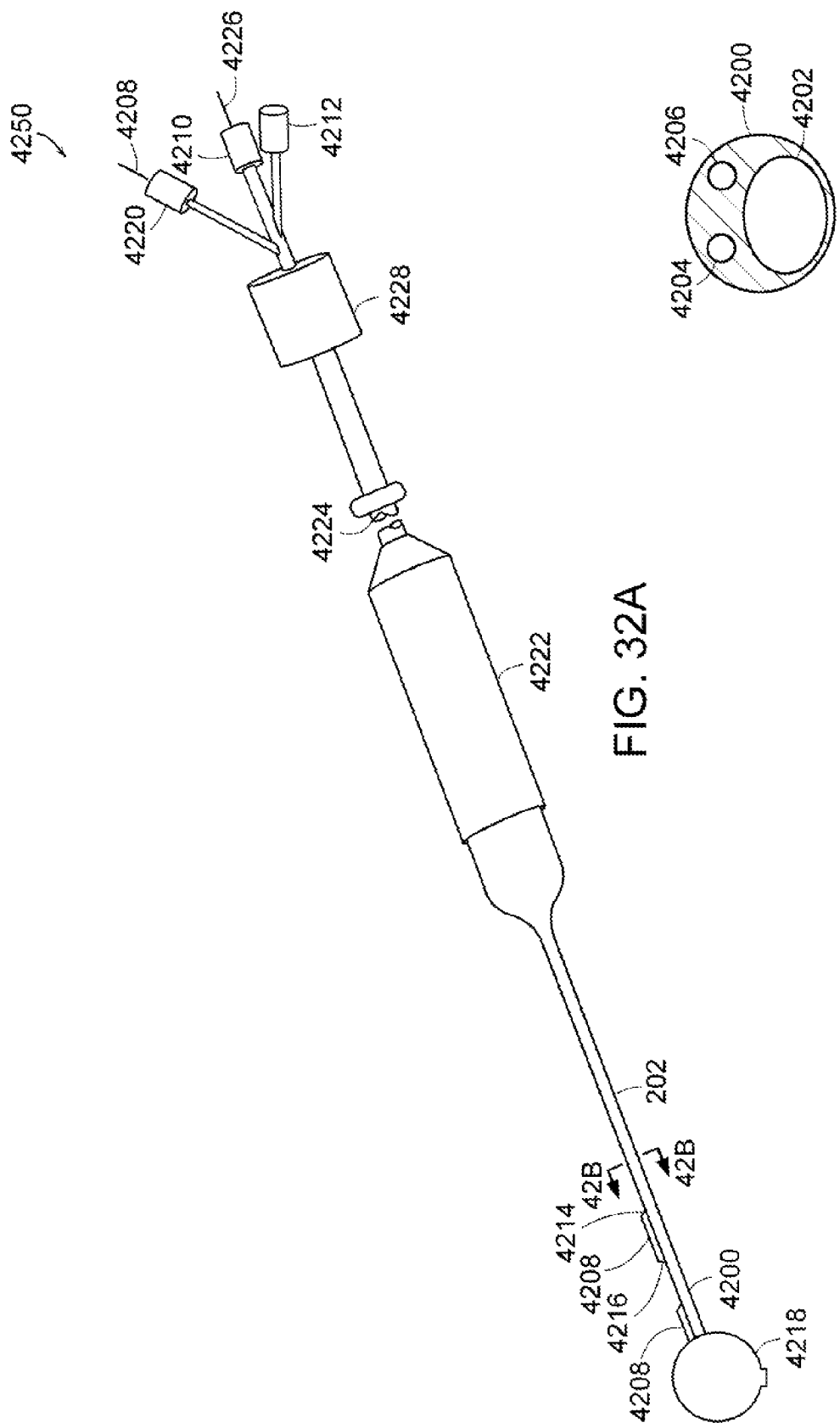
FIG. 32A is a perspective view of a portion of a catheter system for delivery of a gastrointestinal implant device.
FIG. 32B is a cross-sectional view of the catheter shaft taken along line 42B-42B of FIG. 32A.

FIG. 32A is a perspective view of a portion of a low profile catheter system 4250 for delivery of a gastrointestinal implant device. The low profile catheter has a detachable generally spherical shaped element 4218 coupled to the distal end of an inner shaft 4200 to aid the delivery of the catheter through the alimentary canal into the intestines. After the gastrointestinal implant device has been delivered, the spherical shaped element (ball) 4218 is detached and the zero profile catheter is removed through the gastrointestinal implant device. The normal peristalsis of the bowel is used to move the released ball through the intestines.

The catheter system 4250 includes an outer sheath 4222 for storing the collapsible anchor portion of the gastrointestinal implant device in collapsed form. Collapsible anchoring devices have already been described in conjunction with FIGS. 7, 23 and 28-31. The sleeve 202 is secured temporarily outside an inner sheath 4200 allowing for proper positioning of the gastrointestinal implant device and then for release.

FIG. 32B is a cross-sectional view of the inner shaft 4200 of the catheter system as taken along line 42B-42B of FIG. 32A. In one embodiment, the inner shaft 4200 is a three-lumen extrusion of Pebax 7233 with an outer diameter of 0.080 inch and round inner lumens 4202, 4204, 4206 having respective diameters of 0.040, 0.020, and 0.020 inches. This material is selected to maintain a low profile, a small minimum bend radius; that is less than 0.5 inch without kinking, good column strength when fortified with an inner guide wire stylet, and a low coefficient of friction in a material with good thermoplastic and bonding properties.

A first lumen 4202 is used to pass a guide wire or mandrel 4226 through the catheter shaft to increase the rigidity of the catheter shaft during introduction of the catheter into the intestines. The first lumen 4202 is also used to inject fluid to lift the sleeve material 202 away from the inner shaft 4200 after the gastrointestinal device has been delivered to the intestine. A second lumen 4204 is used to pass a sleeve retention wire 4208 to the distal end of the gastrointestinal implant device. The sleeve retention wire is used to hold the distal end of the sleeve 202 to the outside of the inner shaft 4200. A third lumen 4206 is used to inject fluid at the tip of the catheter to lift the distal end of the sleeve 202 off the inner shaft 4200 prior to removal of the catheter system 4250 from the body.

Returning to FIG. 32A, the guide wire 4226 is passed through fitting 4210 connected to the first lumen 4202. The sleeve 202 is located concentrically over the catheter inner shaft 4200. It is held at its distal end to the inner shaft 4200 with the sleeve retention wire 4208. The sleeve retention wire 4208 holds the sleeve 202 in place during delivery.

Proximal fitting 4220 is connected to the second lumen and proximal fitting 4212 is connected to the third lumen 4206. During delivery of the gastrointestinal implant device, the first lumen 4202 is filled with a 0.035 inch Teflon coated guide wire 4226 that provides column strength for the appropriate amount of pushability without compromising the flexibility of the catheter inner shaft 4200. A 0.015 inch diameter Teflon-coated steel wire is placed in the second lumen 4204 to serve as the distal sleeve retention wire. The second lumen 4204 has 2 skive holes 4214, 4216 near the distal end of the catheter shaft 4200. The distal sleeve retention wire 4208 exits the second lumen 4204 through a proximal skive hole 4214 feeds through the sleeve material 202, which is wrapped tightly around the distal outer diameter of the catheter shaft, and re-enters the second lumen 4204 through a distal skive hole 4216. This creates a dead bolt style lock holding the sleeve 202 to the shaft 4200 until ready to be released similar to the dead bolt style lock described in conjunction with the two lumen catheter shaft shown in FIGS. 14A and 14B.

The distal end of the shaft terminates with a spherical shaped element 4218 that is either solid, or inflatable to form an atraumatic tip. In the embodiment shown, the spherical shaped element is a solid ball, similar to the ball described in conjunction with FIG. 17. In the embodiment shown, the diameter of the ball is about 0.5 inch (12.7 mm), however the range of diameters is about 0.25 inch (6.4 mm) to about 0.75 inch (19.2 mm). An embodiment of an inflatable spherical shaped element is described later in conjunction with FIGS. 40A-40B. The ball 4218 at the end of the catheter shaft is held onto the shaft 4200 with the sleeve retention wire 4208 maintaining tension on the ball 4302 which will be described later in conjunction with FIG. 36.

The collapsed anchor assembly is located in outer sheath 4222. The ball 4218 at the end of the catheter is released to withdraw the catheter. The release mechanism pulls the sleeve retention wire to release the ball end and release the end of the sleeve. The anchor assembly is then released from the outer sheath as previously described.

The catheter can be used any time access to the intestinal tract is desired. For example, the catheter can be used to pass an endoscope into the intestine. This catheter device can be used to rapidly run the intestines, place a guide wire and then use the placed guide wire as a track for an endoscope.

Figure 33:
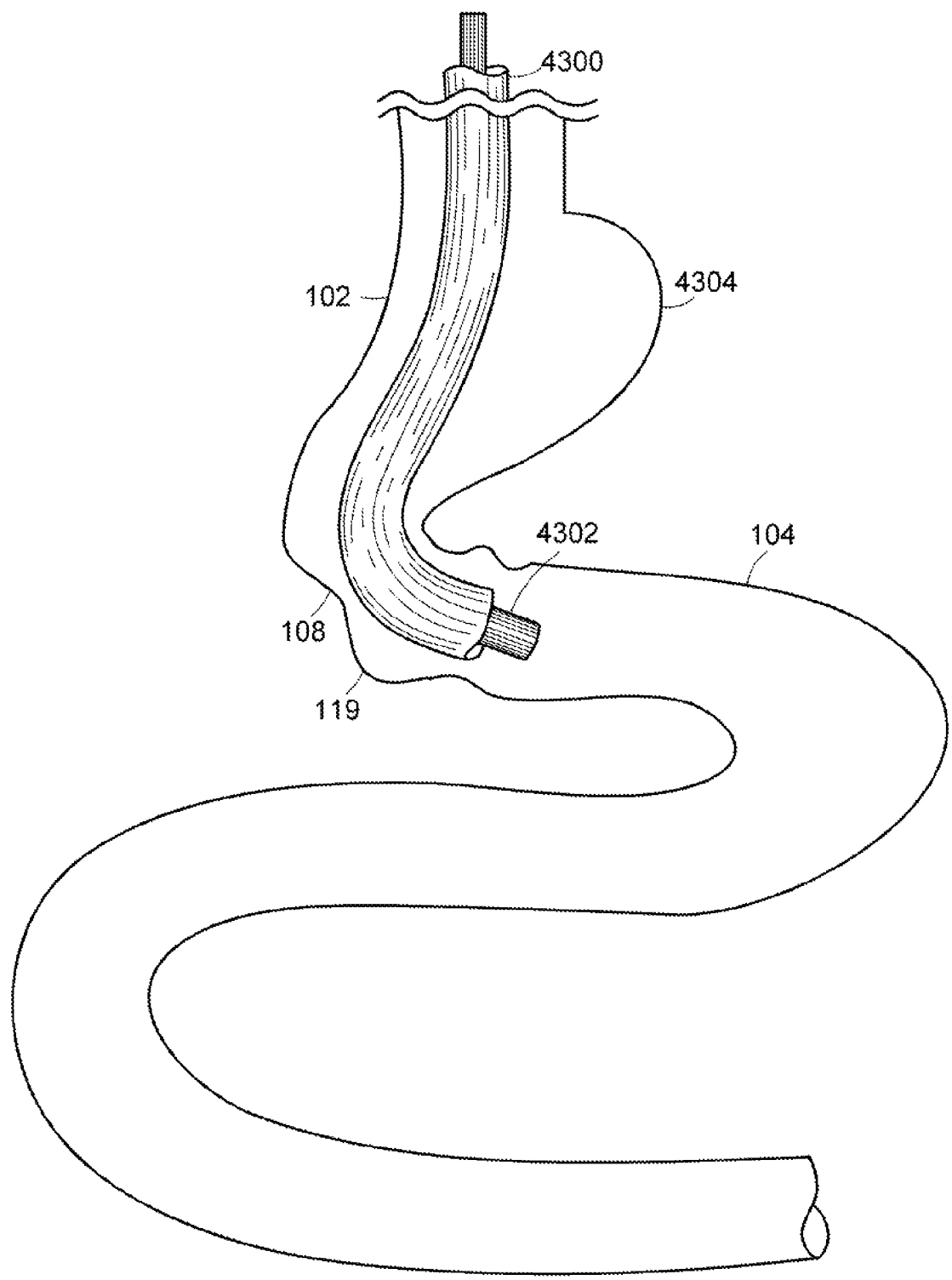
FIG. 33 is a sectional view of a portion of the digestive tract in a body illustrating the position of a gastroscope/guide tube assembly.
Figure 34:
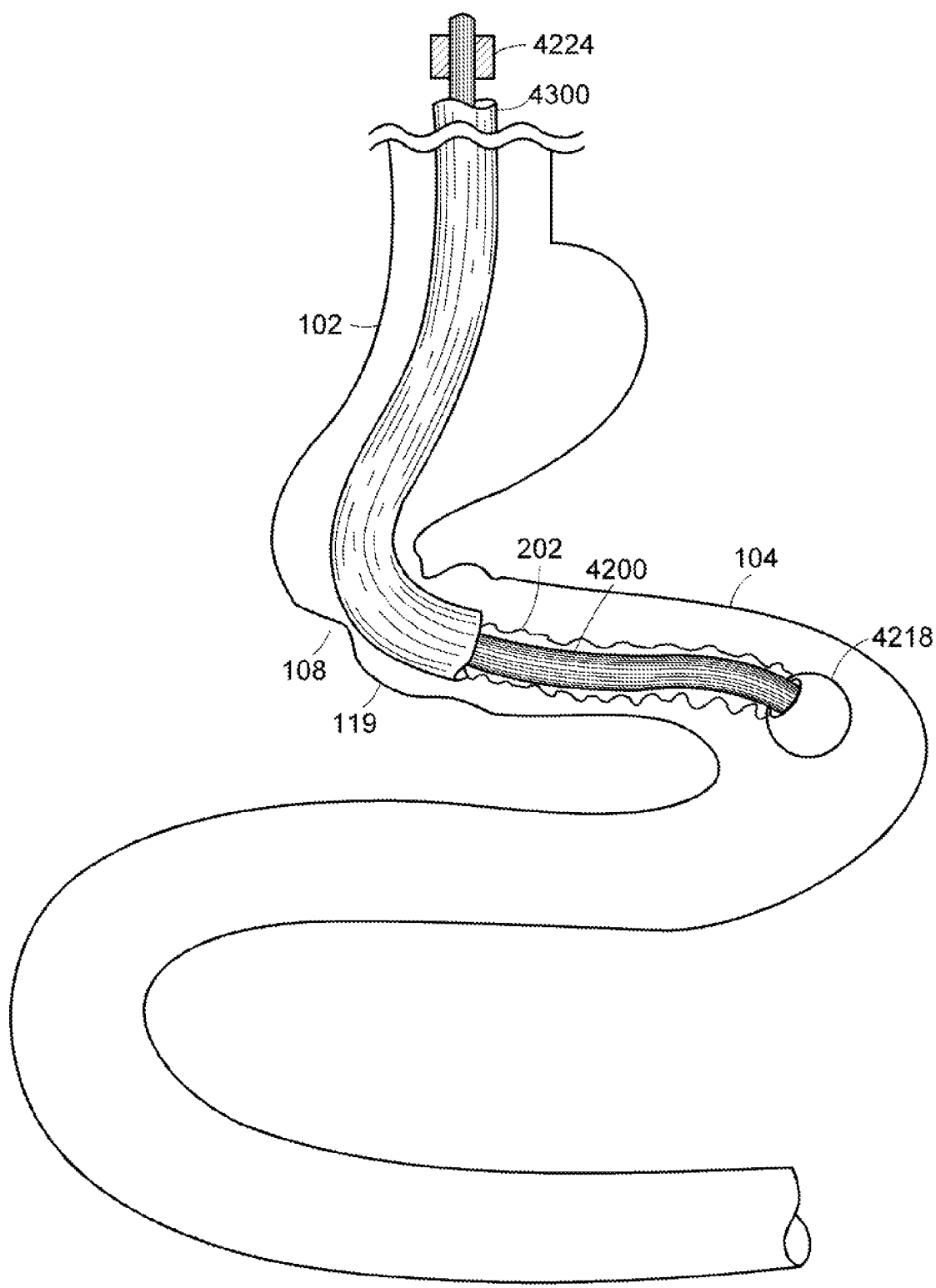
FIG. 34 is a sectional view of a portion of the digestive tract in a body illustrating the distal end of the catheter extending from the distal end of the guide tube 4300.
Figure 35:
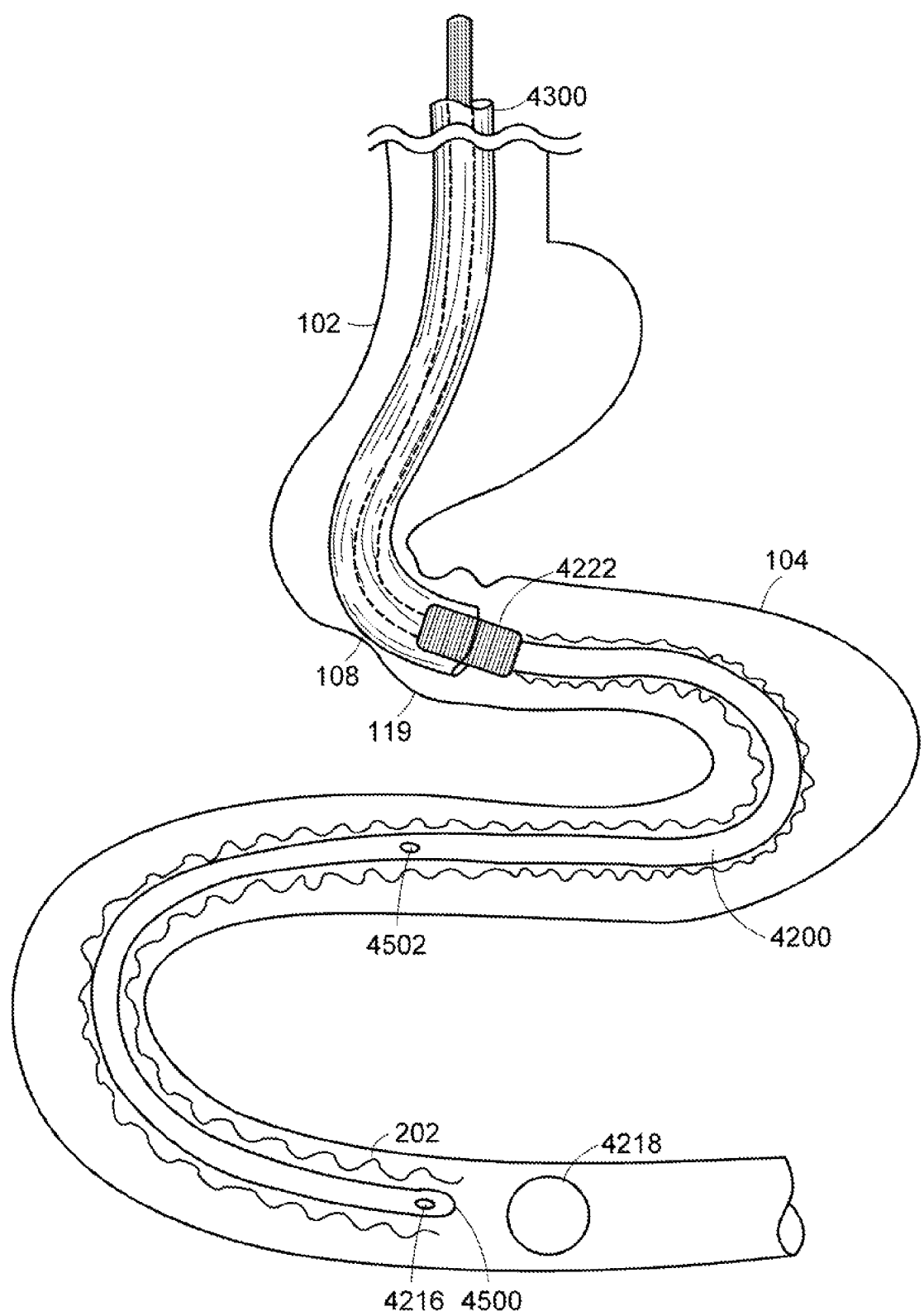
FIG. 35 is a sectional view of a portion of the digestive tract in a body after the gastrointestinal implant device of FIG. 28 has been delivered.

FIGS. 33-35 illustrate the steps for delivery of the gastrointestinal implant device using the low profile catheter described in conjunction with FIGS. 32A-32B. FIG. 33 is a sectional view of a portion of the digestive tract in a body illustrating the position of a gastroscope/guide tube assembly.

The small bowel is accessed endoluminally by passing a semi-rigid tube into the stomach and into the pylorus 108 and proximal duodenum, inflating the bowel with a fluid, preferably water, and then passing a thin, flexible catheter with a large, atraumatic ball tip through the bowel.

A guide tube 4300 is placed over the end of a gastroscope 4302. The guide tube/gastroscope assembly is then placed through the patient's mouth, down the esophagus and into the stomach 102. The assembly is then passed into the pylorus 108 and the duodenum 104.

The guide tube 4300 has an inner diameter of approximately 0.63 inch (16 mm) and an outer diameter of approximately 0.70 inch (18 mm). It is approximately 30 inches (76.2 cm) in length and is made of a flexible polymer such as urethane with a flat wire wrap to provide kink resistance and pushability. The distal end of the guide tube 4300 can have a short, flexible end to minimize trauma to the pylorus 108.

Once in place, fluid is introduced through the channel of the gastroscope 4300 to inflate the intestine distally. Saline or water are preferred but air or carbon dioxide ($CO_2$) can also be used. About 500-1000 cc of fluid is introduced for delivery of a 4 foot length of sleeve. Shorter sleeves require less fluid because the length of intestine to distend is less. Likewise, longer sleeves require more fluid. After the fluid is introduced, the gastroscope is removed from the guide tube.

If desired, the gastroscope 4203 can be removed from the guide tube 4300 and a balloon catheter can be introduced to deliver the fluid. The balloon catheter is delivered to the pylorus and inflated to roughly 0.394-0.591 inches (10-15 mm) to seal the intestine. A balloon catheter has already been described in conjunction with FIG. 18.

FIG. 34 is a sectional view of a portion of the digestive tract in a body illustrating the distal portion of the catheter assembly extending from the distal portion of the guide tube 4300. The catheter assembly 4250 is advanced through the guide tube 4200 after the gastroscope 4302 has been removed from the guide tube. The ball 4218 at the end of the catheter assembly 4250 provides an atraumatic, leading tip to the catheter such that the catheter follows the contour of the intestines.

FIG. 35 is a sectional view of a portion of the digestive tract in a body after the gastrointestinal implant device of FIG. 28 has been delivered. The anchor of the gastrointestinal implant device is located inside the delivery tube 4222, which is located through the pylorus 108. A marker on the proximal end of the catheter 4200 aligns with a corresponding marker on the guide tube 4300 when the catheter is fully inserted. Once the gastrointestinal device is in place, the sleeve retention wire 4208 in the catheter 4302 which holds the sleeve 202 in place and also holds the ball 4218 to the distal tip of the catheter can be removed as discussed in conjunction with the catheter system shown in FIGS. 16A-16C. As the sleeve retention wire is pulled back in a distal direction, both the ball 4400 and the distal end of the sleeve 4500 are released. Fluid is then introduced through the third lumen 4206 in the catheter to open the sleeve 202 and expand the sleeve away from the catheter shaft 4200. Water or saline are preferred fluids although air or $CO_2$ can be used. Approximately 100-200 cc is injected. The fluid exits the catheter at a mid point skive hole 4502 and travels in both a distal and proximal direction. Approximately 20 cc of fluid is then injected through the second lumen 4204 and exits the distal skive hole 4216. This fluid lifts the distal end of the sleeve 202 off the inner catheter shaft 4200.

The guide tube 4300 is then removed and the gastroscope re-introduced into the stomach and through the pylorus 108 to view the duodenum. The proximal anchor is then deployed by pulling back on the delivery tube 4222, which is connected to the proximal end of the catheter. After the anchor is deployed, the catheter system 4250 is withdrawn from the patient. The catheter 4302 has no edges that could catch on the sleeve 202 as it is pulled back through the pylorus 108 and the stomach 102 and the esophagus because the ball is left behind. This zero profile catheter design is important since it is typically very difficult to withdraw devices from the gastro-intestinal tract while leaving catheters or other devices behind.

A method for accessing the small bowel by passing a catheter through the mouth has been described in conjunction with FIGS. 33-35. The low profile catheter can also be used for accessing the small bowel through an incision in the stomach. Instead of delivering the catheter through the top of the stomach as shown in FIG. 33, the catheter is delivered through the stomach, for example, through an incision at position 4304 in FIG. 33. The bowel is filled with a fluid, preferably water, and then the thin, flexible catheter with a large, atraumatic ball tip through the bowel is passed through the bowel as described in conjunction with FIG. 33-35.

Figure 36:
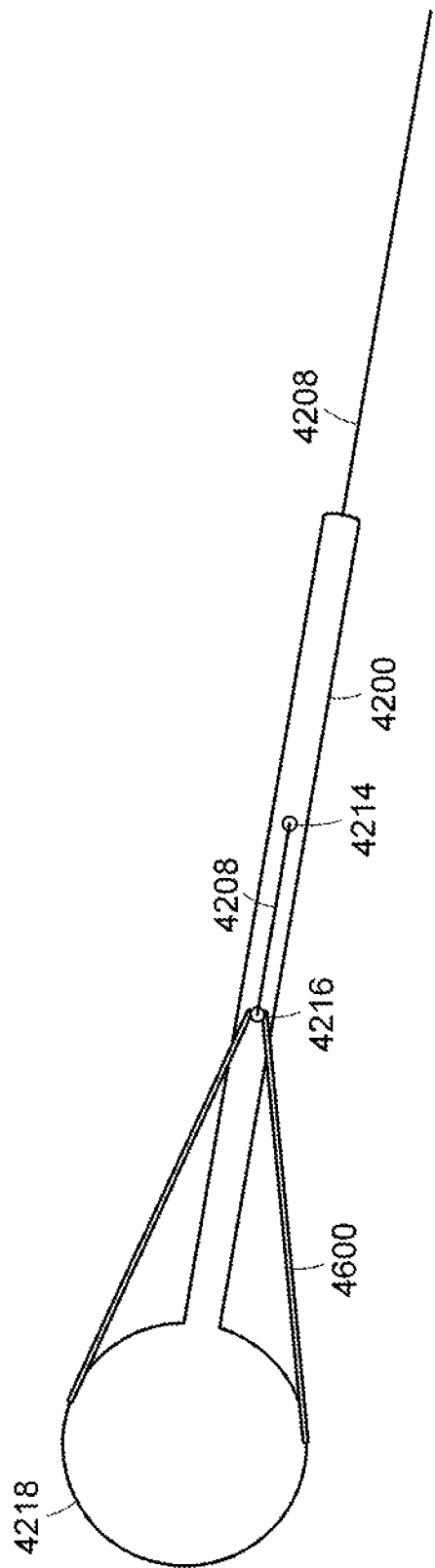
FIG. 36 is a plan view of the distal end of the catheter system illustrating a releasable ball tip mechanism.
Figure 37:
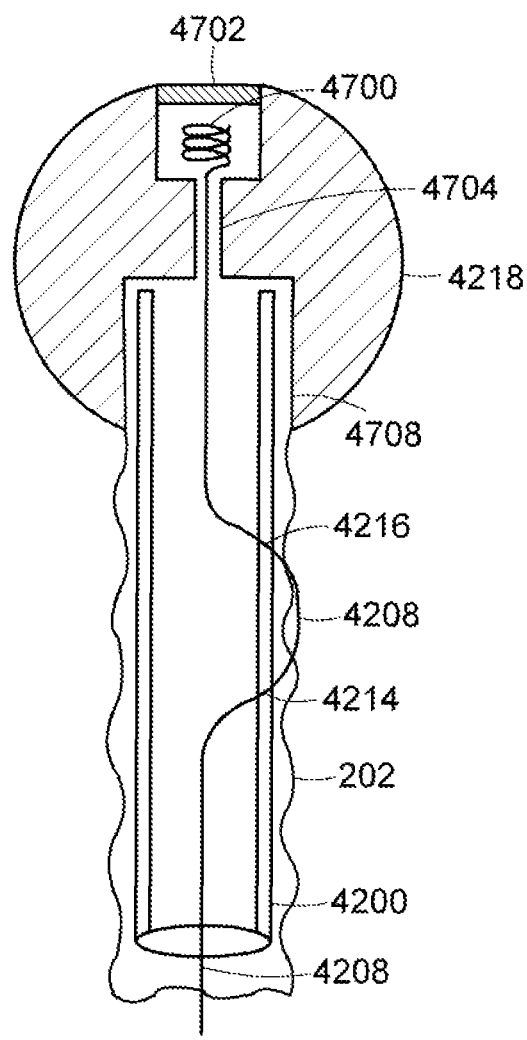
FIG. 37 is a plan view of the distal end of the catheter illustrating an alternative embodiment of a releasable ball tip mechanism.
Figure 38:
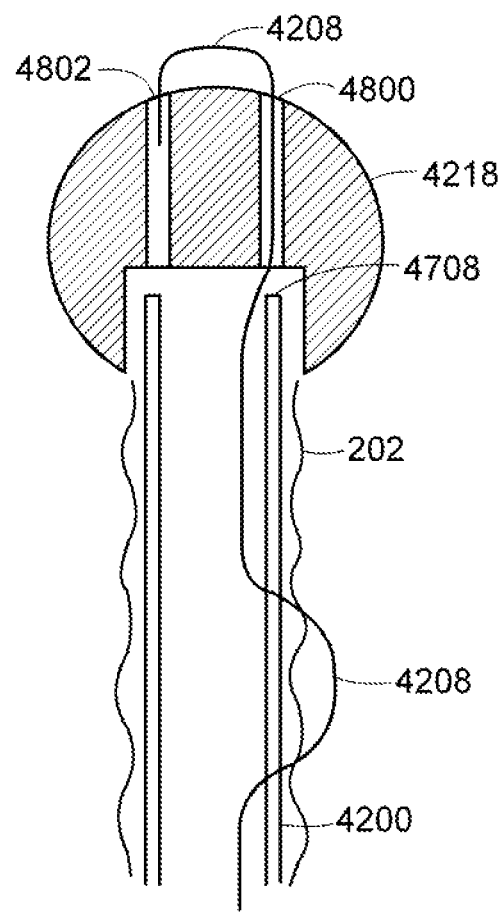
FIG. 38 is a plan view of the distal end of the catheter illustrating yet another embodiment of a releasable ball tip mechanism.

FIGS. 36-38 illustrate embodiments for attaching a releasable spherical shaped element to the distal end of the catheter. FIG. 36 is a plan view of the distal end of the catheter system illustrating a releasable ball tip mechanism. As discussed in conjunction with the catheter system shown in FIG. 32, a sleeve retention wire 4208 travels through second lumen 4204 in the catheter shaft 4200 exits the second lumen 4204 through proximal skive hold 4218 and re-enters the second lumen through distal skive hole 4216.

The ends of a wire, or thread 4600 are attached to the ball 4218 and the thread 4600 is looped through sleeve retention wire 4208 to hold the ball 4218 at the distal end of the inner shaft 4200 of the catheter. The ball 4218 is released by pulling back on sleeve retention wire 4208 with fitting 4200 (FIG. 32A) until thread 4600 is no longer held by sleeve retention wire 4208. The ball 4218 then falls off the distal end of the inner shaft of the catheter 4200 and exits the body through normal peristalsis through the intestines.

FIG. 37 is a plan view of the distal end of the catheter illustrating an alternative embodiment of a releasable ball tip mechanism. The inner shaft 4200 fits in recess 4706 in the ball 4218. The sleeve retention wire 4208 exits the inner shaft 4200 through proximal skive hole 4214, pierces the sleeve 202 and re-enters the inner shaft 4200 through distal proximal skive hole 4216. The distal end of the sleeve retention wire 4208 is formed into a coil shape 4700 and sits in a pocket 4702 in the ball 4218. The pocket 4702 is connected to the recess 4702 through hole 4704, which is of a smaller diameter than the recess 4702 and the pocket 4700. The distal end of the sleeve retention wire 4208 is annealed so that the sleeve retention wire 4208 can be pulled back in a proximal direction and will straighten out to allow the wire to pass through hole 4704.

FIG. 38 is yet another embodiment of a releasable ball tip mechanism. The inner shaft 4200 fits in recess 4706 in the ball 4218. The sleeve retention wire 4208 exits the inner shaft 4200 through proximal skive hole 4214, pierces the sleeve 202 and re-enters the inner shaft 4200 through distal proximal skive hole 4216.

The ball 4218 includes two holes 4800, 4802 extending from the recess 4706 to the exterior surface of the ball 4218. The distal end of the sleeve retention wire 4208 passes through hole 166 and is looped back into hole 167. As the sleeve retention wire 4208 is pulled proximally, the wire 4218 is pulled back through hole 4802 and then through hold 4800 and the ball 4218 is released from the distal end of the catheter.

Figure 39:
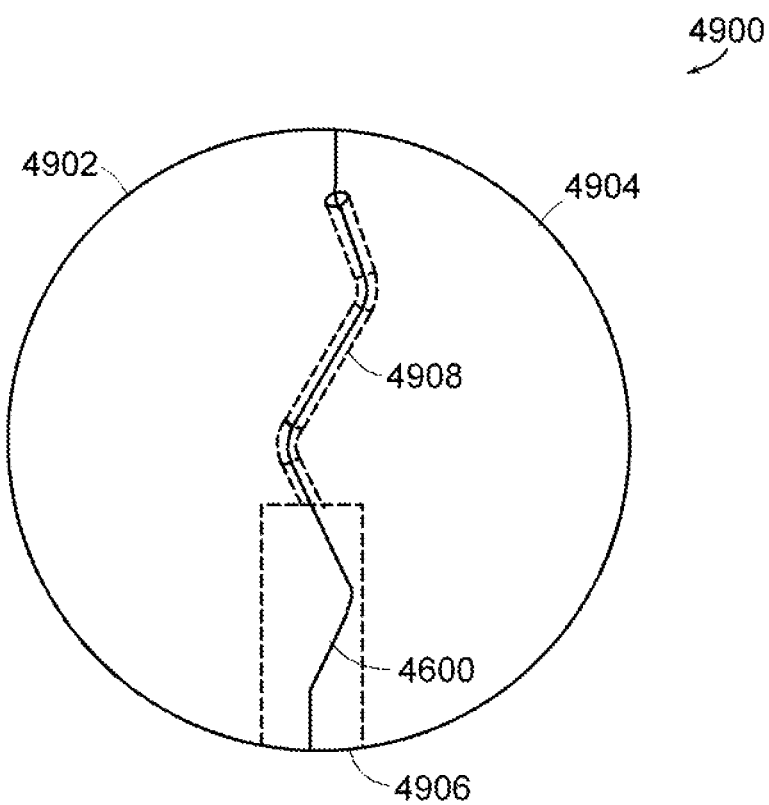
FIG. 39 is a cross sectional view of an alternative embodiment of a solid spherical shaped element.

FIG. 39 is a cross sectional view of an alternative embodiment of a solid spherical shaped element. A ball 4900 is fabricated in two halves, 4902 and 4904. The sleeve retention wire 4006 fits into an S shaped track 4908. The S shape of the track 4908 creates sufficient friction to hold the ball on the end of the catheter during delivery of the gastrointestinal implant device. The sleeve retention wire 4600 fits snugly in the channel 4908 but can be pulled proximally to release the sleeve retention wire 4600 from the ball 4900. The catheter shaft fits in the recess 4906.

Figure 40A:
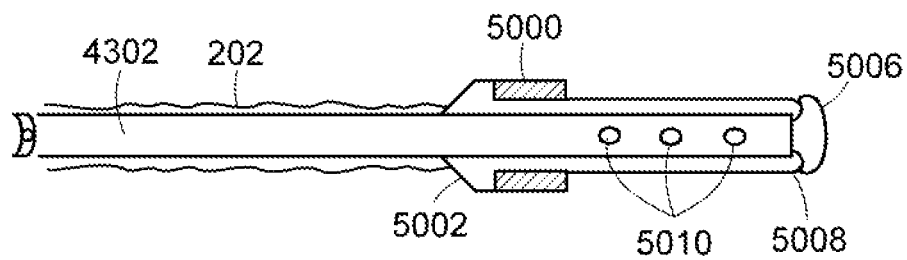
FIG. 40A is a plan view of the distal end of the catheter with an inflatable spherical shaped element.
Figure 40B:
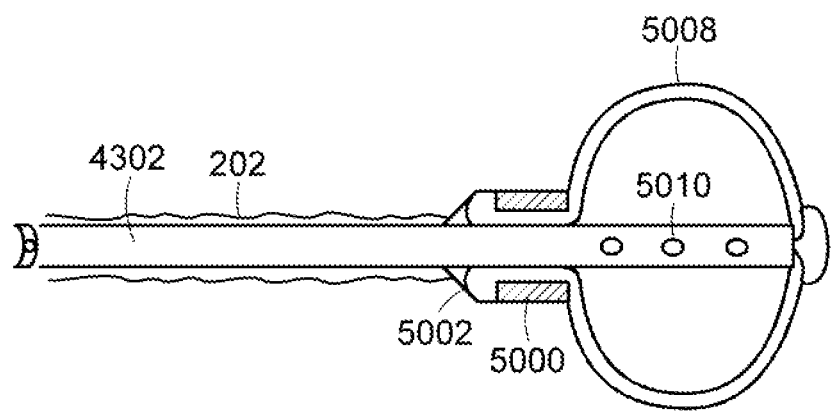
FIG. 40B is a plan view of the distal end of the catheter after the inflatable spherical shaped element has been inflated.

A low profile balloon can be used instead of the ball 4218 at the distal end of the catheter. FIGS. 40A-40B is a plan view of the distal end of the catheter shown in FIG. 34 with a low profile balloon. In the embodiment shown, a low profile balloon replaces the ball at the distal end of the catheter shown in FIG. 34. FIG. 40A is a plan view of the distal end of the catheter with an inflatable spherical shaped element. FIG. 40B is a plan view of the distal end of the catheter after the inflatable spherical shaped element has been inflated;

Referring to FIG. 40A, a silicone, TPE, or latex sleeve 202 is attached to the distal end of the catheter shaft 4302. Filling holes 5010 connect with the inner lumen of the catheter to provide a passage for inflation of an inflatable spherical shaped element (balloon) 5008. The balloon 5008 is attached to the shaft 4302 with a metal band 5000 that has a tapered proximal transition 5002 to minimize edges that could catch on the sleeve 202 after delivery of the sleeve 202. The metal band 5000 is about 0.003-0.005 inches (0.076-0.127 mm) thick. The balloon 5008 can be thin wall molded, tubular polyurethane or silicone. The balloon is stored along the distal catheter shaft 4302 with the distal end pushed into the lumen of the catheter shaft and attached to the catheter shaft 4302 with a plug 5006 to keep the balloon from expanding beyond the tip of the catheter.

FIG. 40B illustrates the distal end of the catheter 4302 after the balloon 5002 has been expanded into a spherical shape. The balloon is expanded by fluid, which flows through the catheter shaft and enters the balloon 5008 through the fluid passage holes from the catheter shaft. The plug 5006 at the end of the catheter shaft ensures that the balloon acts like the ball shown in the embodiment in FIG. 40 by limiting expansion of the balloon beyond the tip of the catheter and the plug also provides some lateral strength to the balloon. By replacing the ball with a balloon at the distal end of the catheter, the distal tip is more stable for axial compression. Also, the catheter will not deflect with side loading.

Figure 41:
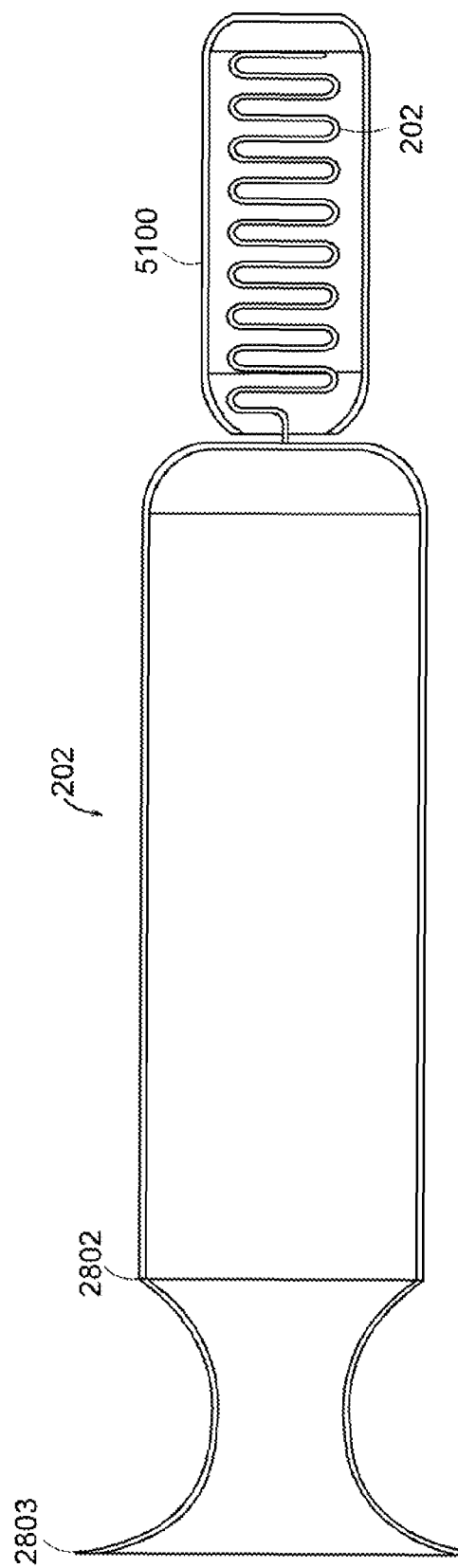
FIG. 41 is a plan view of an alternative delivery system for delivering a gastrointestinal implant device.

The further one tries to pass a device into the intestine, the more difficult it is since friction and tortuosity increase. FIG. 41 is a plan view of an alternative delivery system for delivering a gastrointestinal implant device. The delivery system enables delivery of a long sleeve into the intestine and includes a distal pill with folded sleeve material inside. Peristalsis carries the pill distal in the intestine, causing the sleeve material to unfurl.

The delivery system is not limited to the delivery of a distal section of the sleeve for this embodiment of the gastrointestinal implant device. As described in conjunction with FIG. 28, the gastrointestinal device includes an anchor 2810 and a sleeve 202. The proximal section of the sleeve 202 is fully deployed and some amount of the distal section of sleeve 202 is packed into a pill 5100.

The gastrointestinal implant device is delivered as previously described into the proximal intestines. Once deployed in the intestines, peristalsis from the natural activity of the intestine pulls the pill 5100 distally through the intestine. As the pill is pulled distally, the distal section of the sleeve 202 pulls out of the pill and deploys straight in the intestine. Peristalsis pulls the pill through the remainder of the intestines and the pill finally exits the body.

A one-foot length of sleeve material can be packed into a pill with length of 1 inch (25.4 mm) and diameter of 0.47 inch (12 mm). Therefore, if one only wishes to pass the catheter 2 feet into the intestine for delivery of the gastrointestinal device, the pill 5100 enables a 3 foot sleeve to be delivered with the additional 1 foot distal section of the 3-foot sleeve delivered in the pill 5100.

Figure 42:
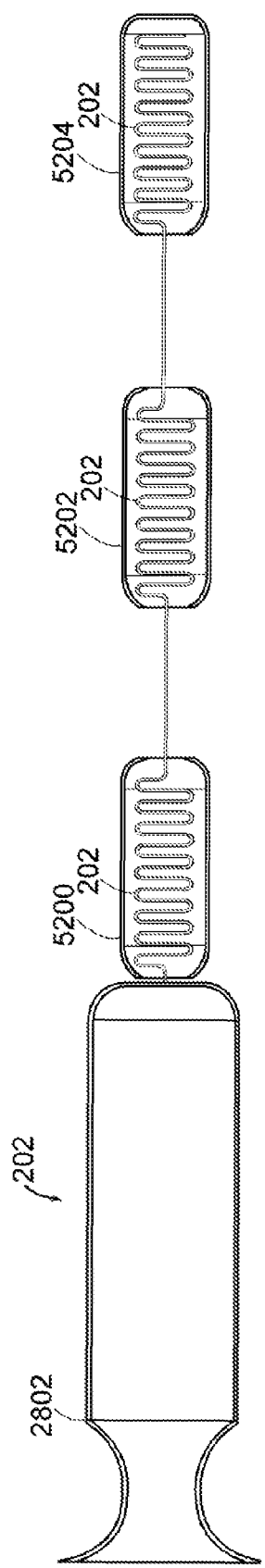
FIG. 42 is a plan view of another embodiment of the delivery mechanism shown in FIG. 41.

FIG. 42 is a plan view of another embodiment of the delivery mechanism shown in FIG. 41. The delivery mechanism enables delivery of a long sleeve into the intestine and includes encapsulated sleeve materials formed into pill shapes. Each pill dissolves in the body at different rates enabling the sleeve to be pulled distally by peristalsis as it unfolds once the pill covering dissolves.

The delivery mechanism is shown for delivery of the gastrointestinal implant device described in conjunction with FIG. 28. The first section of the sleeve 202 is fully deployed after the gastrointestinal implant device has been delivered into the proximal intestine as previously described. A plurality of distal sections of the sleeve 202 are coated to form a plurality of dissolvable pills 5200, 5202, 5204. The coatings applied to form each respective pill 5200, 5202, 5204 are made of a dissolvable material, with each coating tailored to dissolve at different times depending on the polymer make up and the environment. Each pill 5200, 5202, 5204 is carried distally by peristalsis. The coating on the first pill 5200 is selected to dissolve first. After the coating on the first pill 5200 has dissolved, the second and third pills 5202 and 5204 pull the compacted sleeve 202 distally. The coating on the second pill 5202 dissolves next, as the third pill 5204 pulls the sleeve more distally. Finally, the coating on the third pill 5204 dissolves and the sleeve 202 is fully deployed. The plurality of dissolvable pills enables the ultimate delivery of many feet of sleeve material with the simpler delivery of only an initial 1-2 foot section of the sleeve into the proximal intestine. As described in conjunction with the embodiment shown in FIG. 41, a one-foot length of sleeve material can be packed into a pill with length of 1 inch (25.4 mm) and diameter of 0.47 inch (12 mm).

A number of biodegradable materials may be used for the coatings on the pills including polyethylene glycols (PEG), polylactic acids (PLA) and polycaprolactones (PCL). These materials are made in formable resins or in liquids that can be converted to solids through various types of chemical and photochemical reactions. These materials break down into chemicals that are safe to internal tissues. These resins are made biodegradable by formulating a base molecule with a hydrolytically unstable link within the base chain.

For example, PEG is made biodegradable by incorporating lactic acid into the base chain. One end of the lactide molecule forms a link that will break down rapidly in the presence of water. One means of controlling the rate of degradation is by varying the number of lactide elements within the base chain. The greater the number, the faster the chain will break down. Additionally, the percent solids or density of the resulting solid is varied to alter degradation rates. Denser materials take longer to break down. Also, hydrolytically unstable bonds break down faster in elevated pH environments. Such an environment occurs naturally within the small intestines, on the outside of the sleeve where bile and bicarbonates are deposited.

Figure 43C:
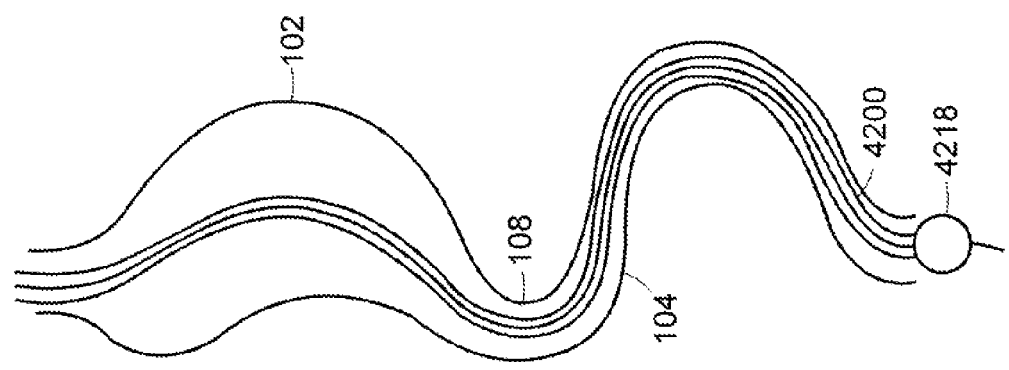
FIGS. 43A-43C illustrate a method for delivering an alternate embodiment of the catheter system 4250 having a central lumen for placement over a guide wire.
Figure 43B:
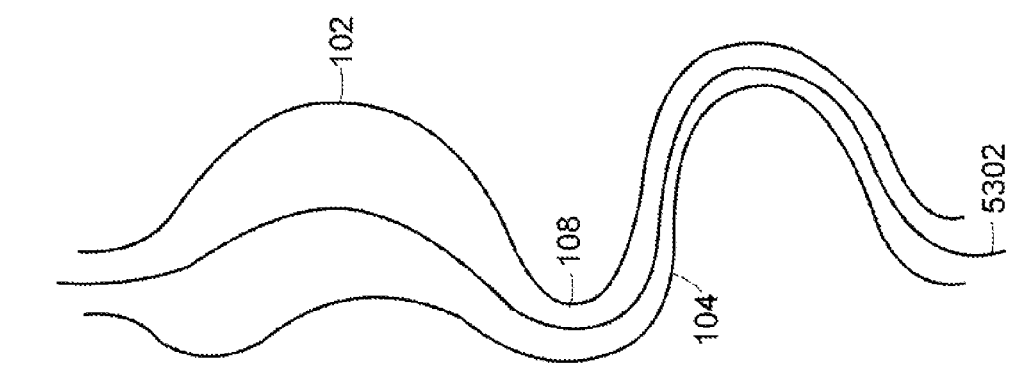
Figure 43A:
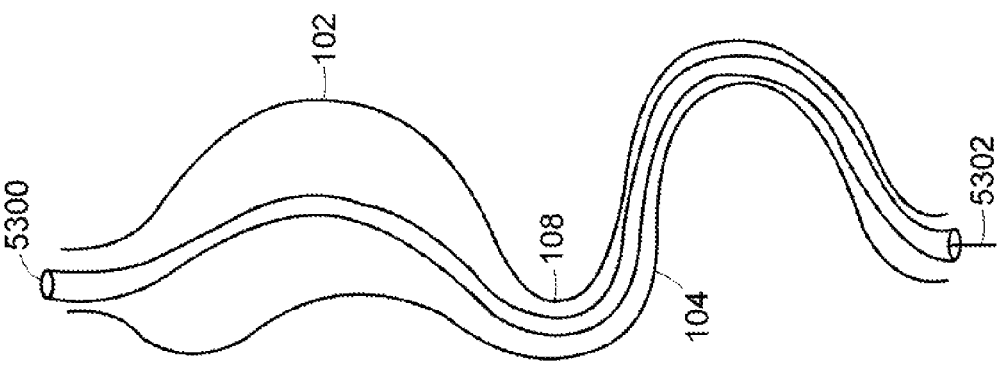

FIGS. 43A-43C illustrate a method for delivering an alternate embodiment of the catheter system 4250 having a central lumen for placement over a guide wire. FIG. 43A is a sectional view of a portion of the digestive tract in a body illustrating an enteroscope 5300 extending through the stomach, through the pylorus 104 to the duodenum 104. A guide wire 5302 is then passed through the enteroscope 5300. After the guide wire has been passed through the enteroscope 5300 is removed. FIG. 43B is a sectional view of a portion of the digestive tract in a body illustrating the guide wire 5302 extending through the stomach 102 and the duodenum 104 after the enteroscope 5300 has been removed. The catheter system follows a guide wire 5302 through the esophagus, the stomach 102, and the pylorus portion 108 of the stomach 102 to the duodenum 104. FIG. 43C is a sectional view of a portion of the digestive tract in a body illustrating the catheter extending through the stomach 102 and duodenum 104 over the guide wire 5300. After the gastrointestinal implant device has been delivered, the catheter 4200 is pulled back through the stomach. After the catheter has been removed, the guide wire 5302 is pulled back through the intestines and the stomach 102.

Figure 44:
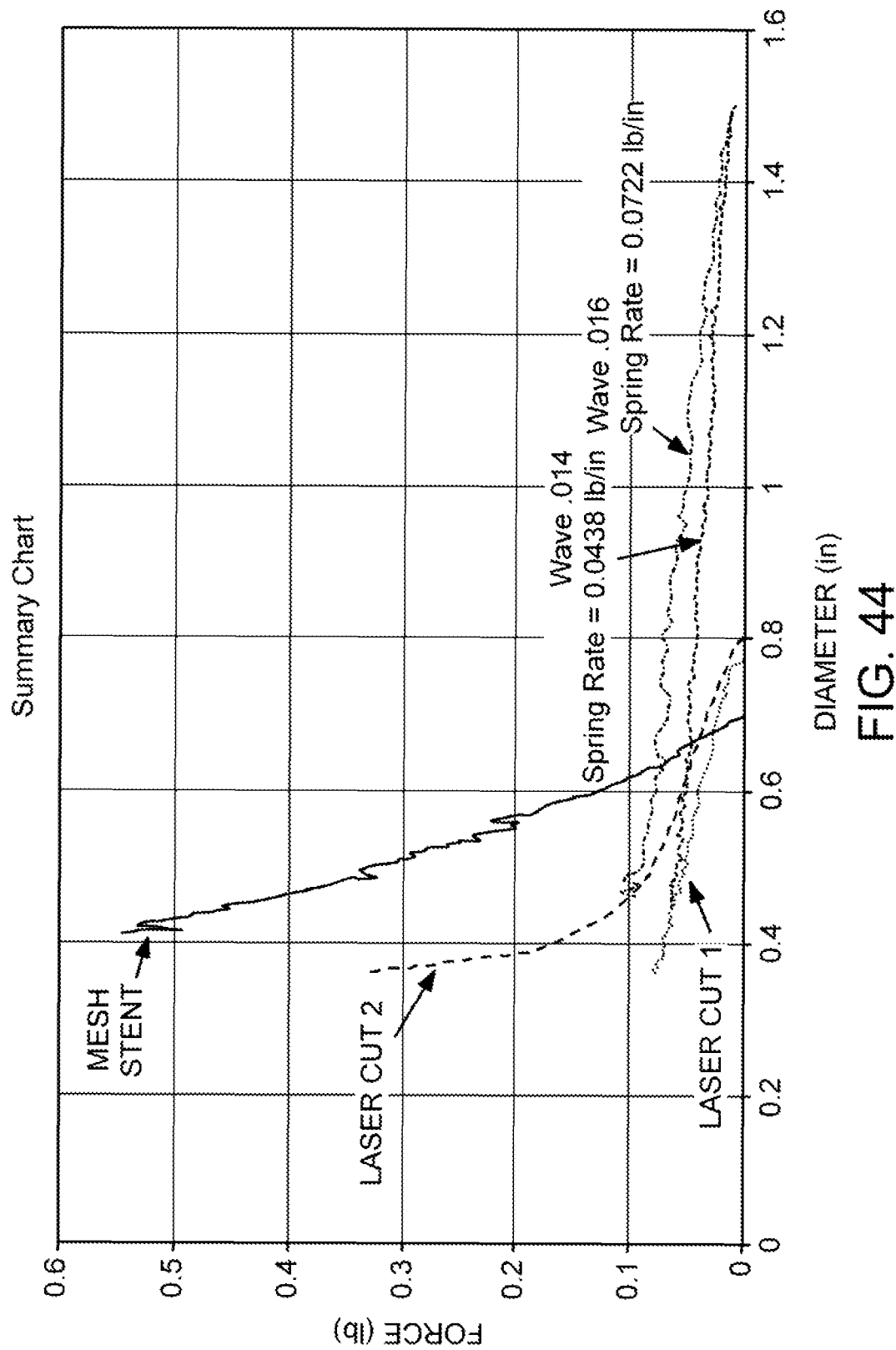
FIG. 44 is a graph of representative compliance curves for different embodiments of the invention.

An advantage of the wave design is the ability to form an anchor having a very flat compliance curve over a very long range of diameters. In general, referring now to FIG. 44, exemplary compliance curves show the radial force exerted by different devices as they are radially compressed. This means that the force against the tissue is substantially constant, even as the intestine contracts. Such a compliant device is less traumatic to the surrounding tissues. Exemplary spring rates of the above-described wave anchors are an order of magnitude less than mesh-type stents. Additionally, the resulting spring rates of the wave anchors are about half that of a typical Nitinol stent made from tubing. Further, the range of motion of commercial stents is less than about 0.5 inches whereas the wave anchors can operate in a range of up to about 1.5 inches with a substantially flat compliance curve. Exemplary test results are provided in Table 1 for known stent and for a number of other devices including wave anchors.

TABLE 1

Test Results

|  | Mesh-type Stent | Wave- 0.014 | Wave- 0.016 | Laser-cut 1 | Laser-cut 2 |
|---|---|---|---|---|---|
| Spring Rate (lbs./inch): | 1.714 | 0.0438 | 0.0722 | 0.168 (long) 0.240 (short) | 0.253 |
| Approx. Range (inches): | 0.3 | 1.0 | 1.0 | 0.5 | 0.35 |

While this invention has been particularly shown and described with references to preferred embodiments thereof, it will be understood by those skilled in the art that various changes in form and details may be made therein without departing from the scope of the invention encompassed by the appended claims.

What is claimed is:

1. A gastrointestinal implant device comprising:
   a flexible sleeve configured to carry chyme from a proximal end of the sleeve to a distal end of the sleeve and adapted to extend into the duodenum; and
   a collapsible self-expanding anchor coupled to the proximal end of the sleeve and adapted to be retained entirely within the duodenal bulb, the anchor having a relaxed diameter of at least about 40 millimeters.

2. The gastrointestinal implant device of claim 1, wherein the anchor is attached to the surrounding anatomy with a mechanical fastener.

3. The gastrointestinal implant device of claim 2, wherein the mechanical fastener is a suture.

4. The gastrointestinal implant device of claim 2, wherein the mechanical fastener is a surgical staple.

5. The gastrointestinal implant device of claim 2, wherein the mechanical fastener is a barb.

6. The gastrointestinal implant device of claim 5, wherein the barb is bi-directional.

7. The gastrointestinal implant device of claim 1, wherein the anchor is attached to the surrounding anatomy with a chemical fastener.

8. The gastrointestinal implant device of claim 7, wherein the chemical fastener is a surgical adhesive.

9. The gastrointestinal implant device of claim 1, wherein the sleeve comprises an anti-buckling mechanism extending along a length of the sleeve.

10. The gastrointestinal implant device of claim 1, wherein the sleeve is impregnated with a drug that reduces hunger.

11. The gastrointestinal implant device of claim 10, wherein the drug that reduces hunger is selected from the group consisting of Leptin, Glucagon-Like Peptide-1 (GLP-1), Cholecystokinin (CCK), peptide YY (PYY), insulin, and ghrelin.

12. The gastrointestinal implant device of claim 1, wherein the sleeve is impregnated with a drug that reduces inflammation.

13. The gastrointestinal implant device of claim 12, wherein the drug that reduces inflammation is selected from the group consisting of aminosalicylates, corticosteroids, immune modifiers, and antibiotics.

14. The gastrointestinal implant device of claim 1, wherein a plurality of distal sections of the sleeve are coated to form a plurality of dissolvable pills.

15. The gastrointestinal implant device of claim 14, wherein the dissolvable pills are configured to dissolve at different times.

16. The gastrointestinal implant device of claim 14, wherein the dissolvable pills have a biodegradable coating.

17. The gastrointestinal implant device of claim 16, wherein the biodegradable coating comprises polyethylene glycol.

18. The gastrointestinal implant device of claim 17, wherein the biodegradable coating comprises polylactic acid.

19. The gastrointestinal implant device of claim 17, wherein the biodegradable coating comprises polycaprolactone.

* * * * *